United States Patent
Hurley et al.

(10) Patent No.: US 10,179,056 B2
(45) Date of Patent: Jan. 15, 2019

(54) TRANSFEMORAL PROSTHETIC SOCKET WITH A TEXTILE-BASED COVER AND INTRA-FRAME FORCE APPLICATORS

(71) Applicant: LIM Innovations, Inc., San Francisco, CA (US)

(72) Inventors: Garrett Ray Hurley, San Francisco, CA (US); Juan Jacobo Cespedes, San Francisco, CA (US); Jesse Robert Williams, San Francisco, CA (US); Preston Fung, South San Francisco, CA (US); Monica Ha, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 0 days.

(21) Appl. No.: 15/360,583

(22) Filed: Nov. 23, 2016

(65) Prior Publication Data

US 2017/0143518 A1 May 25, 2017

Related U.S. Application Data

(60) Provisional application No. 62/259,931, filed on Nov. 25, 2015, provisional application No. 62/287,702, (Continued)

(51) Int. Cl.
*A61F 2/80* (2006.01)
*A61F 2/78* (2006.01)
(Continued)

(52) U.S. Cl.
CPC .............. *A61F 2/80* (2013.01); *A61F 2/5046* (2013.01); *A61F 2/60* (2013.01); *A61F 2/76* (2013.01);
(Continued)

(58) Field of Classification Search
CPC .. A61F 2/60; A61F 2/78; A61F 2/7812; A61F 2/80; A61F 2002/5016;
(Continued)

(56) References Cited

U.S. PATENT DOCUMENTS 1,066,605 A * 7/1913 Hanger ................. A61F 2/60
623/33
1,144,681 A 6/1915 Apgar
(Continued)

FOREIGN PATENT DOCUMENTS

DE 319623 3/1920
EP 204407 12/1986
(Continued)

OTHER PUBLICATIONS

Allard USA, "Cut-4-Custom: Custom TLSO in Less Than an Hour," O&P Edge Magazine, downloaded from the internet: <URL: http://www.oandp.com/articles/news_2010-07-01_24_asp>, 2 pages, Jul. 2010.

(Continued)

*Primary Examiner* — Thomas J Sweet
*Assistant Examiner* — Christie Bahena
(74) *Attorney, Agent, or Firm* — Gordon & Jacobson, P.C.

(57) ABSTRACT

An intra-frame positioning sling may be disposed internally within a prosthetic socket frame. The sling may include one or more proximal suspension portions adapted to suspend from a proximal aspect of the frame and a tensioning system. The sling may include a first longitudinal side with one or more proximal suspension portions and an opposite longitudinal side that includes the residual limb interfacing or force application portion of the sling. When the tensioning system is tensioned, the sling is pulled toward the first longitudinal side of the prosthetic socket frame. A set of two (Continued)

positioning slings may be rigged in a transfemoral prosthetic socket frame; one sling applies force on a medial side of a hosted residual limb, and the other sling applies force on the lateral side.

3 Claims, 31 Drawing Sheets

Related U.S. Application Data filed on Jan. 27, 2016, provisional application No. 62/305,477, filed on Mar. 8, 2016.

(51) Int. Cl.
    *A61F 2/50* (2006.01)
    *A61F 2/60* (2006.01)
    *A61F 2/76* (2006.01)

(52) U.S. Cl.
    CPC .............. *A61F 2/78* (2013.01); *A61F 2/7812* (2013.01); *A61F 2/7843* (2013.01); *A61F 2002/503* (2013.01); *A61F 2002/509* (2013.01); *A61F 2002/5012* (2013.01); *A61F 2002/5018* (2013.01); *A61F 2002/5021* (2013.01); *A61F 2002/5027* (2013.01); *A61F 2002/5032* (2013.01); *A61F 2002/5052* (2013.01); *A61F 2002/5053* (2013.01); *A61F 2002/607* (2013.01); *A61F 2002/608* (2013.01); *A61F 2002/7862* (2013.01); *A61F 2002/7875* (2013.01); *A61F 2002/802* (2013.01)

(58) Field of Classification Search
    CPC ...... A61F 2002/5023; A61F 2002/5021; A61F 2002/5026; A61F 2002/5027; A61F 2002/503; A61F 2002/509; A61F 2002/5083; A61F 2002/607; A61F 2002/608; A61F 2002/7818; A61F 2002/7837; A61F 2002/7862; A61F 2002/7887; A61F 2002/802; A61F 5/01; A61F 5/0102; A61F 5/0195; A61F 5/04
    See application file for complete search history.

(56) References Cited

U.S. PATENT DOCUMENTS

| | | |
|---|---|---|
| 1,893,853 A | 1/1933 | Tullis |
| 2,025,835 A | 12/1935 | Trautman |
| 2,229,728 A | 1/1941 | Eddels |
| 2,634,424 A | 4/1953 | O'Gorman |
| 2,759,271 A | 8/1956 | Von Duyke |
| 2,908,016 A | 10/1959 | Botko |
| 2,949,674 A | 8/1960 | Wexler |
| 3,678,587 A | 7/1972 | Madden |
| 4,161,042 A | 7/1979 | Cottingham et al. |
| 4,225,982 A | 10/1980 | Cochrane et al. |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,116,382 A | 5/1992 | Steinkamp et al. |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,387,245 A | 2/1995 | Fay et al. |
| 5,431,624 A | 7/1995 | Saxton et al. |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,651,792 A | 7/1997 | Telikicherla |
| 5,652,053 A | 7/1997 | Liegeois |
| 5,718,925 A | 2/1998 | Kristinsson et al. |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Slemker |
| 5,944,679 A | 8/1999 | DeToro |
| 6,033,440 A | 3/2000 | Schall et al. |
| 6,051,026 A | 4/2000 | Biedermann |
| 6,206,932 B1 | 3/2001 | Johnson |
| 6,228,124 B1 | 5/2001 | Slemker et al. |
| 6,231,618 B1 | 5/2001 | Schall et al. |
| D453,591 S | 2/2002 | Garden |
| 6,368,357 B1 | 4/2002 | Schon et al. |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,576,022 B2 | 6/2003 | Meyer et al. |
| 6,669,736 B2 | 12/2003 | Slemker et al. |
| 6,700,563 B1 | 3/2004 | Koizumi |
| 6,761,743 B1 | 7/2004 | Johnson |
| 6,767,332 B1 | 7/2004 | Pardue |
| 6,942,703 B2 | 9/2005 | Carstens |
| 6,974,484 B2 | 12/2005 | Caspers |
| 7,090,700 B2 | 8/2006 | Curtis |
| 7,105,122 B2 | 9/2006 | Karason |
| 7,172,714 B2 | 2/2007 | Jacobson |
| 7,240,414 B2 | 7/2007 | Taylor, Sr. |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,591,857 B2 | 9/2009 | Slemker et al. |
| 7,658,720 B2 | 2/2010 | Johnson, III |
| 7,753,866 B2 | 7/2010 | Jackovitch |
| 7,762,973 B2 | 7/2010 | Einarsson et al. |
| 7,980,921 B2 | 7/2011 | Saravanos |
| 7,985,192 B2 | 7/2011 | Sheehan et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,142,517 B2 | 3/2012 | Horie |
| 8,303,527 B2 | 11/2012 | Joseph |
| 8,317,873 B2 * | 11/2012 | Doddroe ............... A61F 2/7812 623/36 |
| 8,323,353 B1 | 12/2012 | Alley et al. |
| 8,382,852 B2 | 2/2013 | Laghi |
| 8,403,993 B2 | 3/2013 | Aram et al. |
| 8,465,445 B2 | 6/2013 | George |
| 8,470,050 B2 | 6/2013 | Dillingham |
| 8,535,389 B2 | 9/2013 | McKinney |
| 8,576,250 B2 | 11/2013 | Sabiston et al. |
| 8,894,719 B2 | 11/2014 | Egilsson et al. |
| D723,163 S | 2/2015 | Gottlieb |
| 8,978,224 B2 | 3/2015 | Hurley et al. |
| 9,044,349 B2 | 6/2015 | Hurley et al. |
| 9,155,636 B1 | 10/2015 | Fikes |
| 9,265,629 B2 | 2/2016 | Kelley et al. |
| 9,345,590 B2 | 5/2016 | Arabian et al. |
| 9,468,542 B2 | 10/2016 | Hurley et al. |
| 9,468,543 B2 | 10/2016 | Hurley et al. |
| 9,474,633 B2 | 10/2016 | Williams et al. |
| 9,549,828 B2 | 1/2017 | Hurley et al. |

(56) References Cited

U.S. PATENT DOCUMENTS

| | | | |
|---|---|---|---|
| D778,452 S | 2/2017 | Cespedes et al. | |
| 9,974,668 B2* | 5/2018 | Halldorsson | A61F 2/7812 |
| 2001/0005798 A1* | 6/2001 | Caspers | A61F 2/5046 |
| | | | 623/34 |
| 2002/0099450 A1 | 7/2002 | Dean, Jr. et al. | |
| 2003/0181990 A1 | 9/2003 | Phillips | |
| 2004/0158332 A1 | 8/2004 | Carstens | |
| 2004/0204771 A1 | 10/2004 | Swanson, Sr. | |
| 2004/0260402 A1 | 12/2004 | Baldini et al. | |
| 2006/0009860 A1 | 1/2006 | Price, Jr. | |
| 2006/0020348 A1 | 1/2006 | Slemker et al. | |
| 2006/0020349 A1 | 1/2006 | Slemker | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2007/0298075 A1 | 12/2007 | Borgia et al. | |
| 2008/0188788 A1* | 8/2008 | Serola | A61B 17/1325 |
| | | | 602/75 |
| 2008/0269914 A1 | 10/2008 | Coppens et al. | |
| 2009/0036999 A1 | 2/2009 | Egilsson et al. | |
| 2009/0076625 A1 | 3/2009 | Groves et al. | |
| 2009/0105844 A1 | 4/2009 | Ortiz | |
| 2009/0240344 A1 | 9/2009 | Colvin et al. | |
| 2009/0299490 A1 | 12/2009 | Summit | |
| 2010/0016772 A1 | 1/2010 | DeToro et al. | |
| 2010/0036300 A1 | 2/2010 | Sheehan et al. | |
| 2010/0036505 A1 | 2/2010 | Hassler | |
| 2010/0082116 A1 | 4/2010 | Johnson et al. | |
| 2010/0160722 A1 | 6/2010 | Kuyava et al. | |
| 2010/0274364 A1 | 10/2010 | Pacanowsky et al. | |
| 2011/0029096 A1 | 2/2011 | Laghi | |
| 2011/0071647 A1 | 3/2011 | Mahon | |
| 2011/0114635 A1 | 5/2011 | Sheehan et al. | |
| 2011/0160871 A1 | 6/2011 | Boone et al. | |
| 2011/0232837 A9 | 9/2011 | Ottleben | |
| 2011/0320010 A1 | 12/2011 | Vo | |
| 2012/0022667 A1 | 1/2012 | Accinni et al. | |
| 2012/0041567 A1 | 2/2012 | Cornell | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0165956 A1 | 6/2012 | Li | |
| 2012/0191218 A1 | 7/2012 | McCarthy | |
| 2012/0215324 A1 | 8/2012 | King | |
| 2012/0253475 A1 | 10/2012 | Kelley et al. | |
| 2012/0271210 A1* | 10/2012 | Galea | A61F 2/7812 |
| | | | 602/7 |
| 2012/0271214 A1 | 10/2012 | Blanck | |
| 2012/0271433 A1 | 10/2012 | Galea et al. | |
| 2012/0293411 A1 | 11/2012 | Leithinger | |
| 2013/0123940 A1 | 5/2013 | Hurley et al. | |
| 2013/0192071 A1 | 8/2013 | Esposito et al. | |
| 2013/0197318 A1 | 8/2013 | Herr et al. | |
| 2013/0245785 A1 | 9/2013 | Accini et al. | |
| 2013/0282141 A1 | 10/2013 | Herr et al. | |
| 2014/0005801 A1 | 1/2014 | Van der Watt et al. | |
| 2014/0031953 A1 | 1/2014 | Mackenzie | |
| 2014/0121783 A1 | 5/2014 | Alley | |
| 2014/0149082 A1 | 5/2014 | Sanders et al. | |
| 2014/0180185 A1 | 6/2014 | Zachariasen | |
| 2014/0277584 A1 | 9/2014 | Hurley et al. | |
| 2014/0277585 A1 | 9/2014 | Kelley et al. | |
| 2014/0379097 A1 | 12/2014 | Hurley et al. | |
| 2015/0168943 A1 | 6/2015 | Hurley et al. | |
| 2015/0190252 A1 | 7/2015 | Hurley et al. | |
| 2015/0265434 A1 | 9/2015 | Hurley et al. | |
| 2015/0320576 A1* | 11/2015 | Riedel | A61F 2/7812 |
| | | | 623/32 |
| 2015/0352775 A1 | 12/2015 | Geshlider et al. | |
| 2016/0000587 A1 | 1/2016 | Hurley et al. | |
| 2016/0022466 A1 | 1/2016 | Pedtke et al. | |
| 2016/0058584 A1 | 3/2016 | Cespedes et al. | |
| 2016/0143752 A1 | 5/2016 | Hurley et al. | |
| 2016/0235560 A1 | 8/2016 | Cespedes et al. | |
| 2016/0334780 A1 | 11/2016 | Dair et al. | |
| 2017/0027718 A1 | 2/2017 | Williams et al. | |
| 2017/0027720 A1 | 2/2017 | Pedtke et al. | |
| 2017/0079811 A1 | 3/2017 | Kelley et al. | |

FOREIGN PATENT DOCUMENTS

| | | |
|---|---|---|
| EP | 1433447 | 6/2004 |
| GB | 127451 | 6/1919 |
| GB | 2080114 | 2/1982 |
| WO | 1991016019 | 10/1991 |
| WO | 1998012994 | 4/1998 |
| WO | 2000003665 | 1/2000 |
| WO | 2000030572 | 6/2000 |
| WO | 2007035875 | 3/2007 |
| WO | 2008116025 | 9/2008 |
| WO | 2009093020 | 7/2009 |
| WO | 2012021823 | 2/2012 |
| WO | 2014004709 | 1/2014 |
| WO | 2014068269 | 5/2014 |

OTHER PUBLICATIONS

Alley, "The high-fidelity interface: Skeletal stabilization through alternating soft tissue compression and release," Myoelectric Symposium, Aug. 14-19, 2011 (3 pages).

Andrysek, "Lower-limb prosthetic technologies in the developing world: a review of literature from 1994-2010," Prosthetics and orthotics international, 34(4):378-398, Dec. 1, 2010.

Burgess et al., "The Management of Lower-Extremity Amputation: Surgery: Immediate Postsurgical Prosthetic Fitting: Patient Care," Superintendent of Documents, U.S. Government Printing Office, Washington D.C., publication prepared or the Prosthetic and Sensory Aids Service Dept of Medicine and Surgery, Veterans Administration, Aug. 1969 (129 pages).

Comfil (thermoformable composite technique). Fillauer Fabrication Manuel. Jun. 15, 2012.

Compton et al., "New plastics for forming directly on the patient*," Prosthetics and orthotics international, 2(1):43-47, Apr. 1978.

Conn, "Materials Science: A look At Some of the Substances on the Market for Device Fabrication," O&P Almanac, pp. 28-31, Jun. 2012.

Fairley, "From Academia to the Developing World," downloaded from <http://www.oandp.com/articles/2011-05_03.asp>, The O&P Edge, 5 pages, May 2011.

Fairley, "M.A.S. Socket: A Transfemoral Revolution," downloaded from <http://www.oandp.com/articles/2004-06_03.asp>, The O&P Edge, 3 pages, Jun. 2004.

Fairley, "Socket can be fabricated, modified, fitted-in one hour," downloaded from <http://www.oandp.com/articles/2007-06_09.asp>, The O&P Edge, 3 pages, Jun. 2007.

Fillauer LLC and Centri® "Comfil® Thermo Formable Composite Technique" Fillauer Fabrication Manuel, 14 pages, Jun. 15, 2012.

Gard, "Overview of Lower Limb Prosthetics Research," WRAMC and the VA Orthopedic & Prosthetic Workshop, Arlington, VA, 49 slides, Nov. 17, 2003.

Geil, "Consistency, precision, and accuracy of optical and electro-magnetic shape-capturing systems for digital measurement of residual-limb anthropometrics of persons with transtibial amputation," J Rehabil Res Dev., 44 (4):515-524, May 20, 2007.

Gerschutz et al., "Mechanical Evaluation of Direct Manufactured Prosthetic Sockets," American Academy of Orthotists & Prosthetists, 38th Academy Annual Meeting and Scientific Symposium, USA, <URL: http://oandp.org/publications/iop/2012/2012-19.pdf>, 1 pages, Mar. 21, 2012.

Gleave, "A plastic socket and stump casting technique for above-knee prostheses," J Bone Joint Surg Br., 47:100-103, Feb. 1965.

Greenwald et al., "Volume Management: Smart Variable Geometry Socket (SVGS) Technology for Lower-Limb Prostheses," JPO: Journal of Prosthetics and Orthotics, 15(3):107-112, Jul. 1, 2003.

Hanger Inc., "ComfortFlex Socket System," downloaded from http://www.hanger.com/prosthetics/services/Technology/Pages/ComfortFlex.aspx, 2 pages, archived Sep. 17, 2012.

(56) References Cited

OTHER PUBLICATIONS

Hanger Prosthetics & Orthotics [online] "ComfortFlex Socket System," downloaded from the internet: <URL: http://www.hanger.com/prosthetics/services/Technology/Pages/ComfortFlex.aspx> on Nov. 28, 2012, 2 pages.
Hong et al., "Dynamic moisture vapor transfer through textiles part I: clothing hygrometry and the influence of fiber hype," Textile Research Journal, 58(12):697-706, Dec. 1, 1988 [abstract only].
Hwang [designer], "Blooming Winner-Spark!" Spark Galleries, 3 pages, 2012.
Instamorph, "Moldable Plastic: Instructions" downloaded from URL: <http://www.instamorph.com/instructions>, 2 pages, archived Dec. 24, 2011.
Instamorph: "Remoldable prosthetics"; Apr. 2013, <www.instamorph.com/ideas/outdoors-and-ergonomics/remoldable-prosthetics>.
Jana, "Designing a cheaer, simpler prosthetic arm," ZDNet [online], <URL: http://www.zdnet.com/article/designing-a-cheaper-simpler-prosthetic-arm/> 3 pages, Nov. 14, 2011.
Koike et al., "The TC double socket above-knee prosthesis," Prosthet Orthot Int., 5(3):129-134, Dec. 1981.
Krouskop et al., "Computer-aided design of a prosthetic socket for an above-knee amputee," J Rehabil Res Dev., (24):31-38, 1987.
Manucharian, "An investigation of comfort level trend differences between the hands-on patellar tendon bearing and hands-off hydrocast transtibial prosthetic sockets," J Prosthet Orthot., 23(3):124-140, Jul. 1, 2011.
Ottobock, "Initial and interim prostheses" Prosthetics Lower Extremities 2008, downloaded from the internet: <URL: http://www.ottobockus.com/cps/rde/xbcr/ob_us_en/08cat_4_pdf> on Feb. 2013, pp. 24-26.
Ottobock, "PU Resin Kit Polytol®" downloaded from the internet: <URL: http://www.ottobock.com/cps/rde/xchg/ob_com_en/hs.xsl/17414.html> on Dec. 17, 2012, 2 pages.

Quigley, "Prosthetics Management: Overview, Methods and Materials," Chapter 4, Atlas of Limb Prosthetics: Surgical, Prosthetic, and Rehabilitation Principles, (Second Edition), 19 pages, 1992.
Sanders et al., "Residual limb volume change: Systematic review of measurement and management," J Rehabil Res Dev., 48(8):949-986, 2011.
Sathishkumar et al., "A cost-effective, adjustable, femoral socket, temporary prosthesis for immediate rehabilitation of above-knee amputation," Int J Rehabil Res., 27(1):71-74, Mar. 1, 2004 [abstract only].
SBIR, "Pro-Active Dynamic Accommodating Socket" Solicitation Topic Code: OSD08-H18, 2 pages, Solicitation Year: 2008.
Smith, "Silver Linings for O&P Devices" The Academy Today, 1(4):A-8-A-9, Oct. 2005.
Spaeth, "Laser imaging and computer-aided design and computer-aided manufacture in prosthetics and orthotics," Phys Med Rehabil Clin N Am., 17(1):245-263, Feb. 28, 2006 [abstract only].
Turner, "Fit for Everyone," Yanko Design [online], <URL:http://www.yankodesign.com/2013/07/17/fit-for-everyone/>, 7 pages, Jul. 17, 2013.
Wilson et al., "Recent advances in above-knee prosthetics," Artif. Limbs., 12(2):1-27, Jan. 1, 1968.
Wilson Jr., "A material for direct forming of prosthetic sockets," Artif. Limbs., 14(1):53-56, Jan. 1, 1970.
Wu et al., "Technical note: CIR sand casting system for trans-tibial socket," Prosthet Orthot Int., 27(2):146-152, Aug. 2003.
Zhang, "Ethylene-vinyl acetate copolymer based on a continuous phase of dual/polycaprolactone blend of the porous material prepared," Yangzhou University, Materials Science, Master's Thesis, [USPTO translation of relevant portions of Zhang article], 131 pages, 2010.

\* cited by examiner

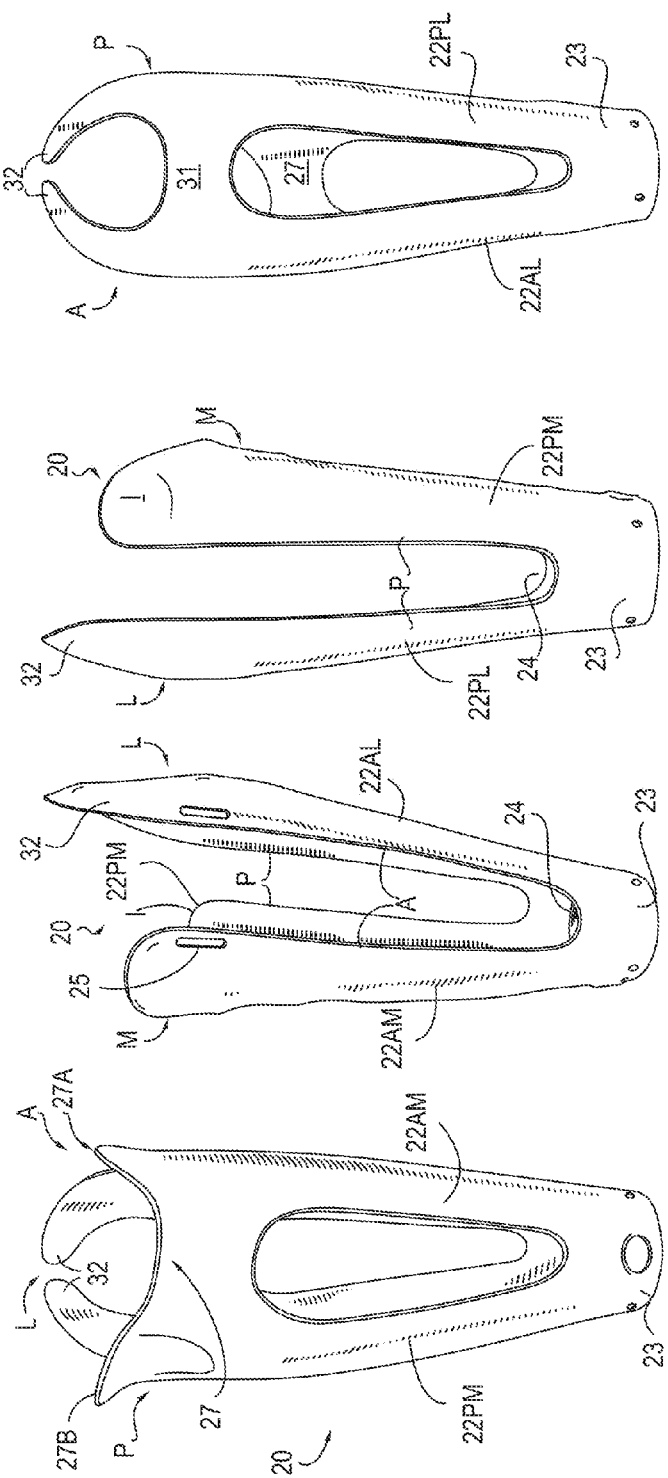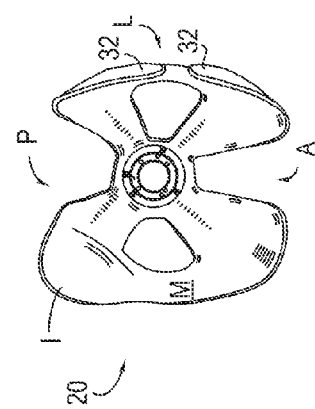

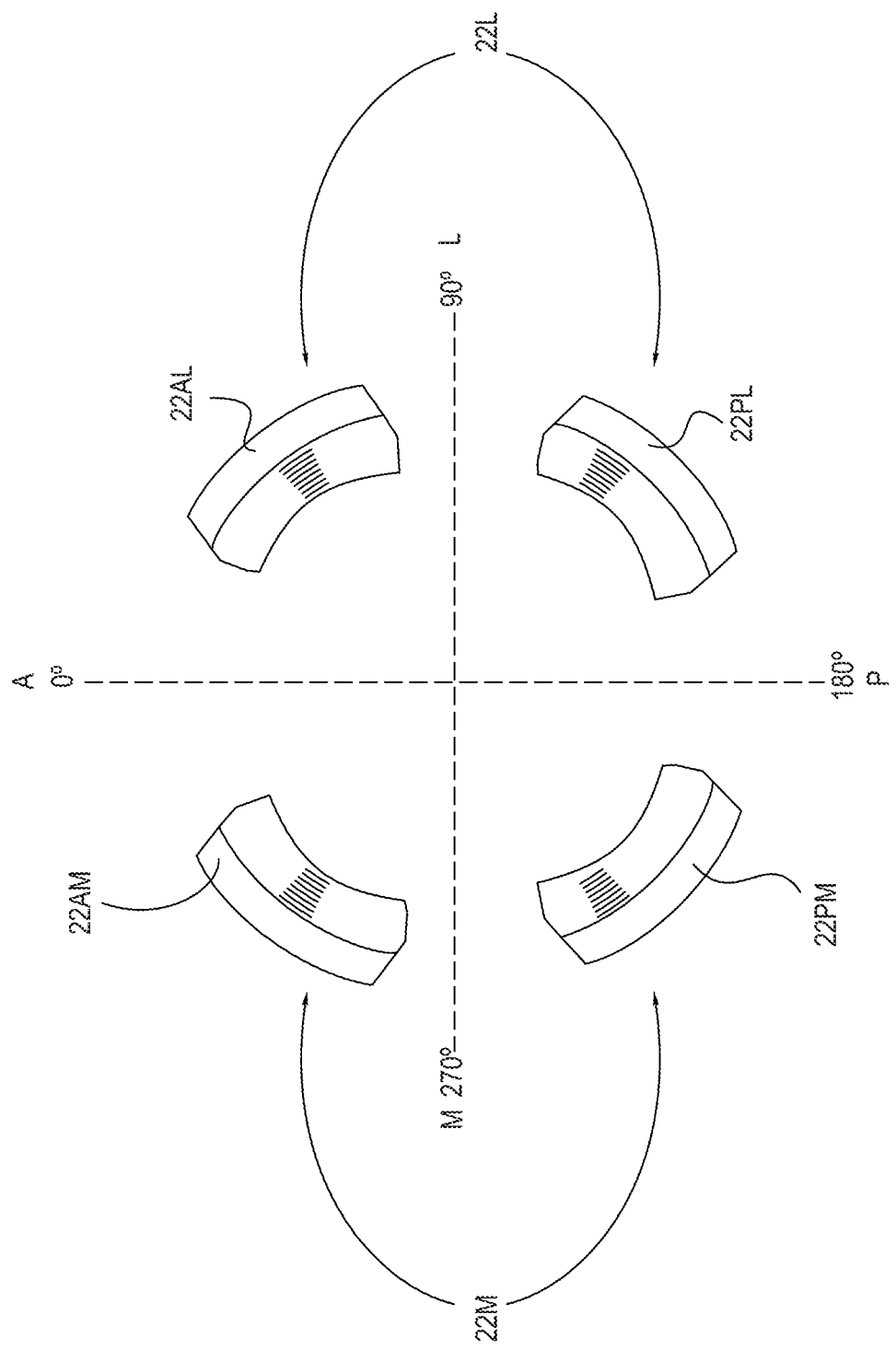

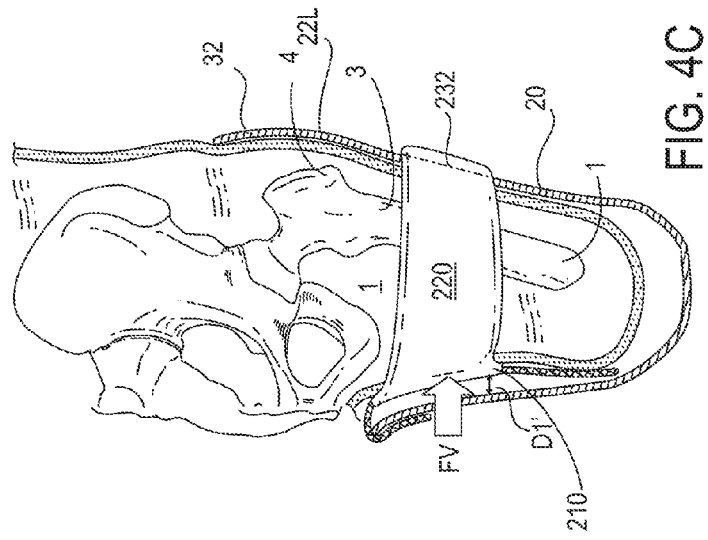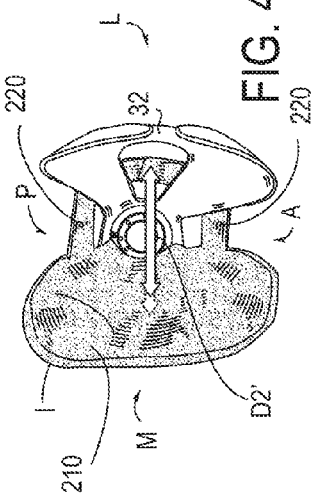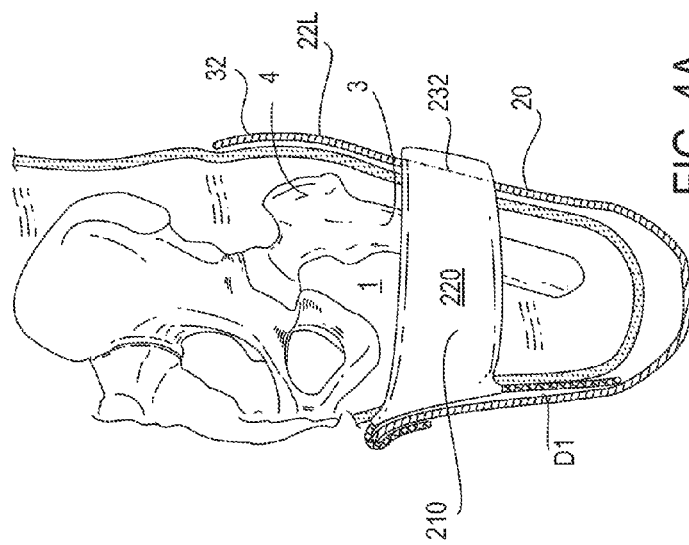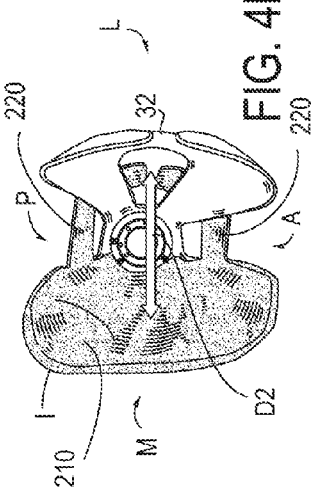
FIG. 4A
FIG. 4B
FIG. 4C
FIG. 4D

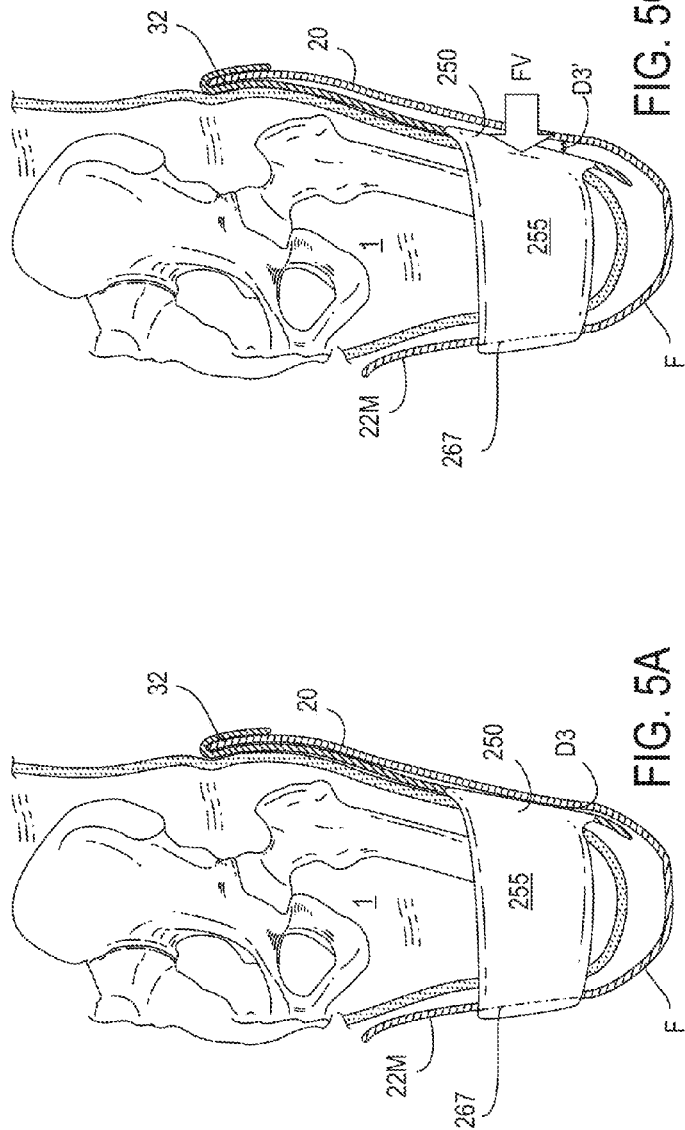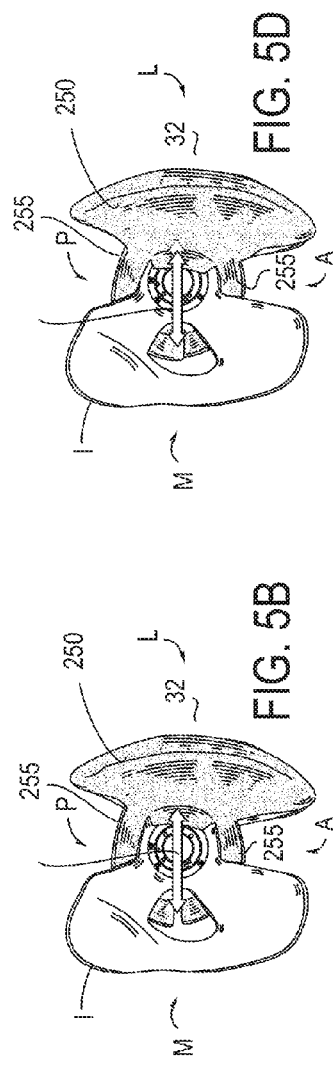

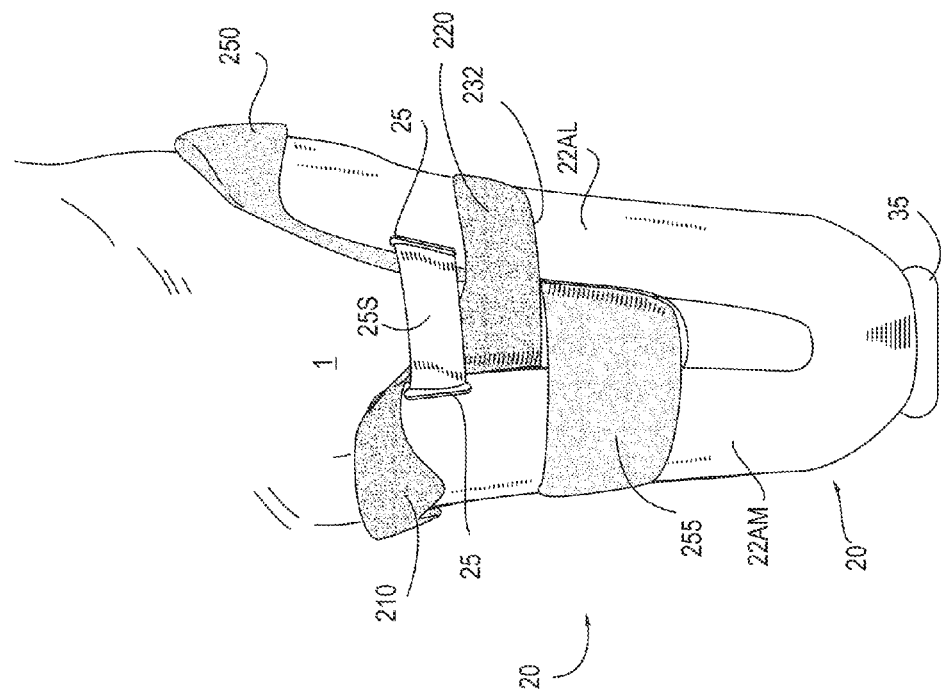
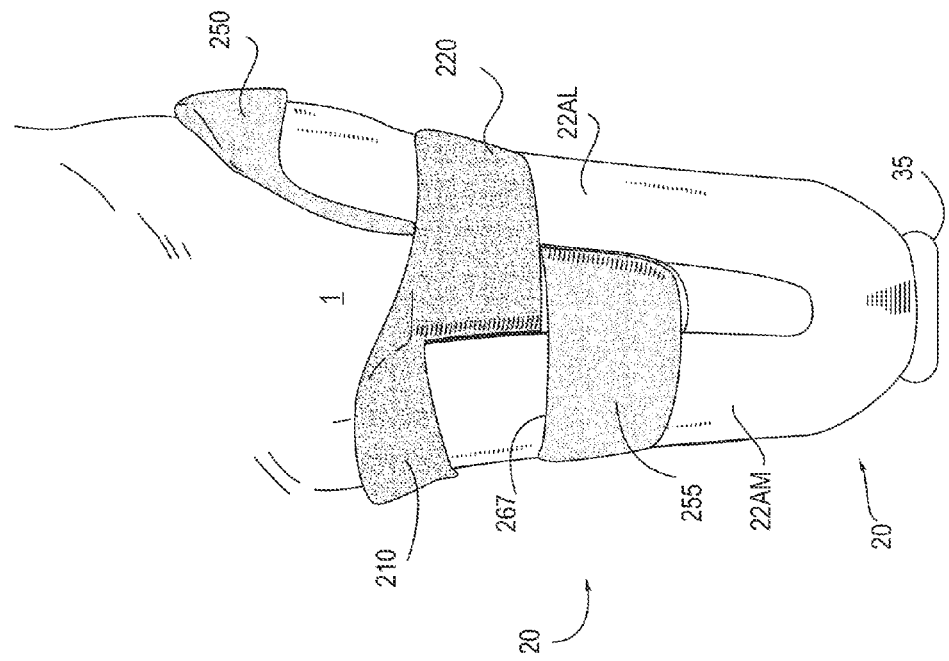

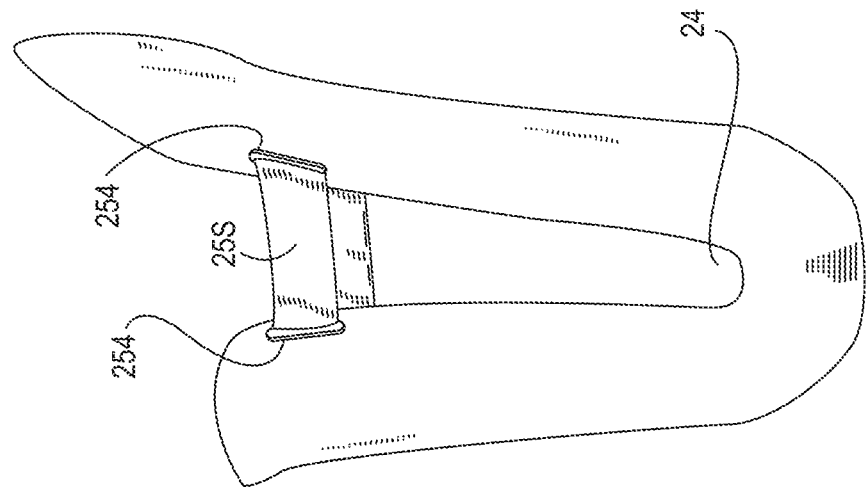
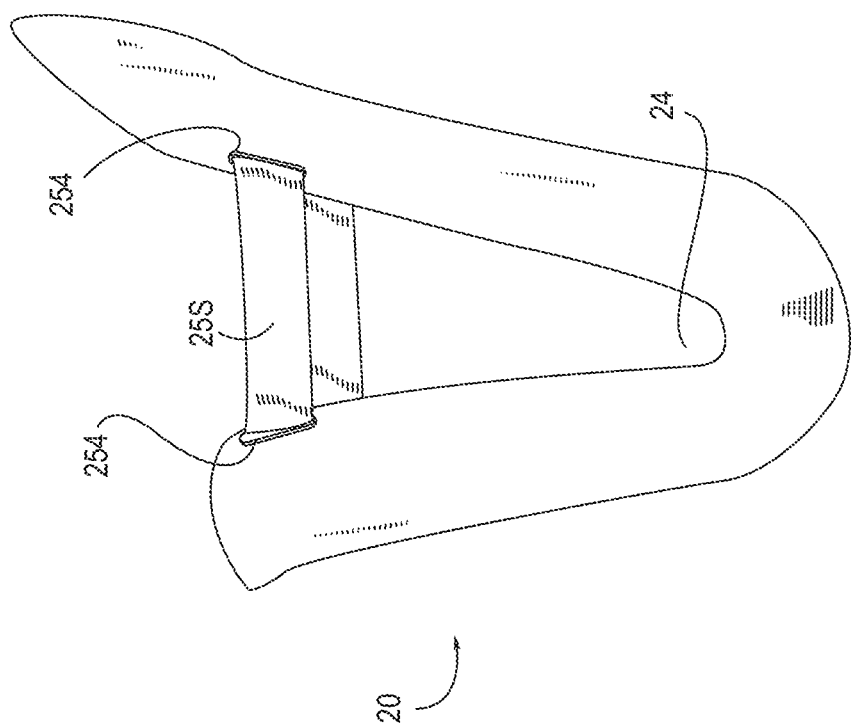

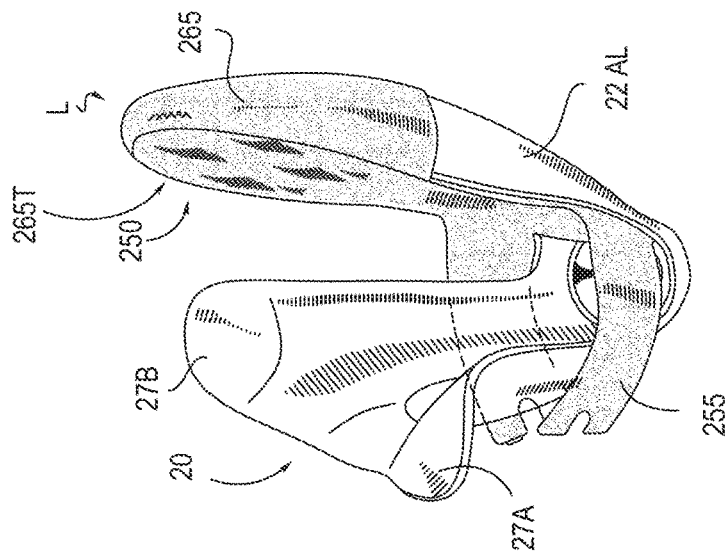
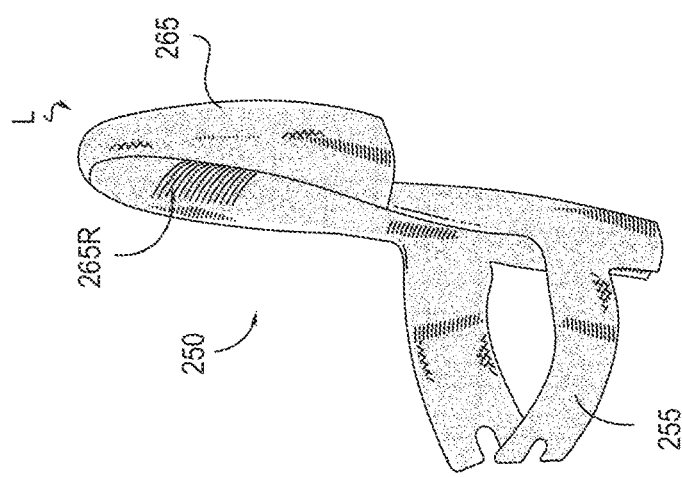
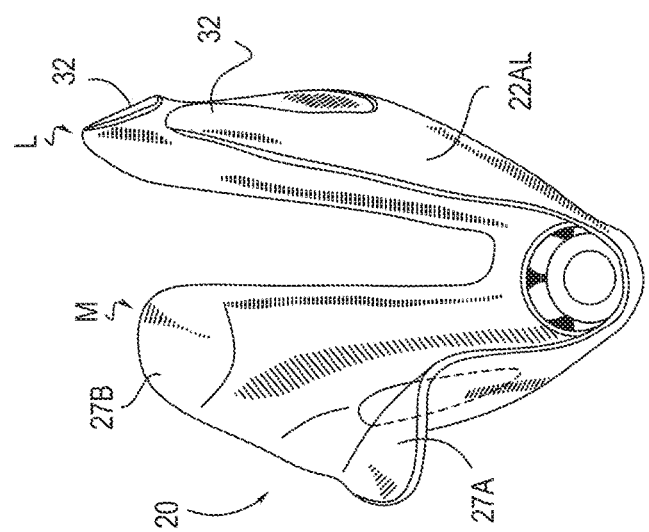
FIG. 8C
FIG. 8B
FIG. 8A

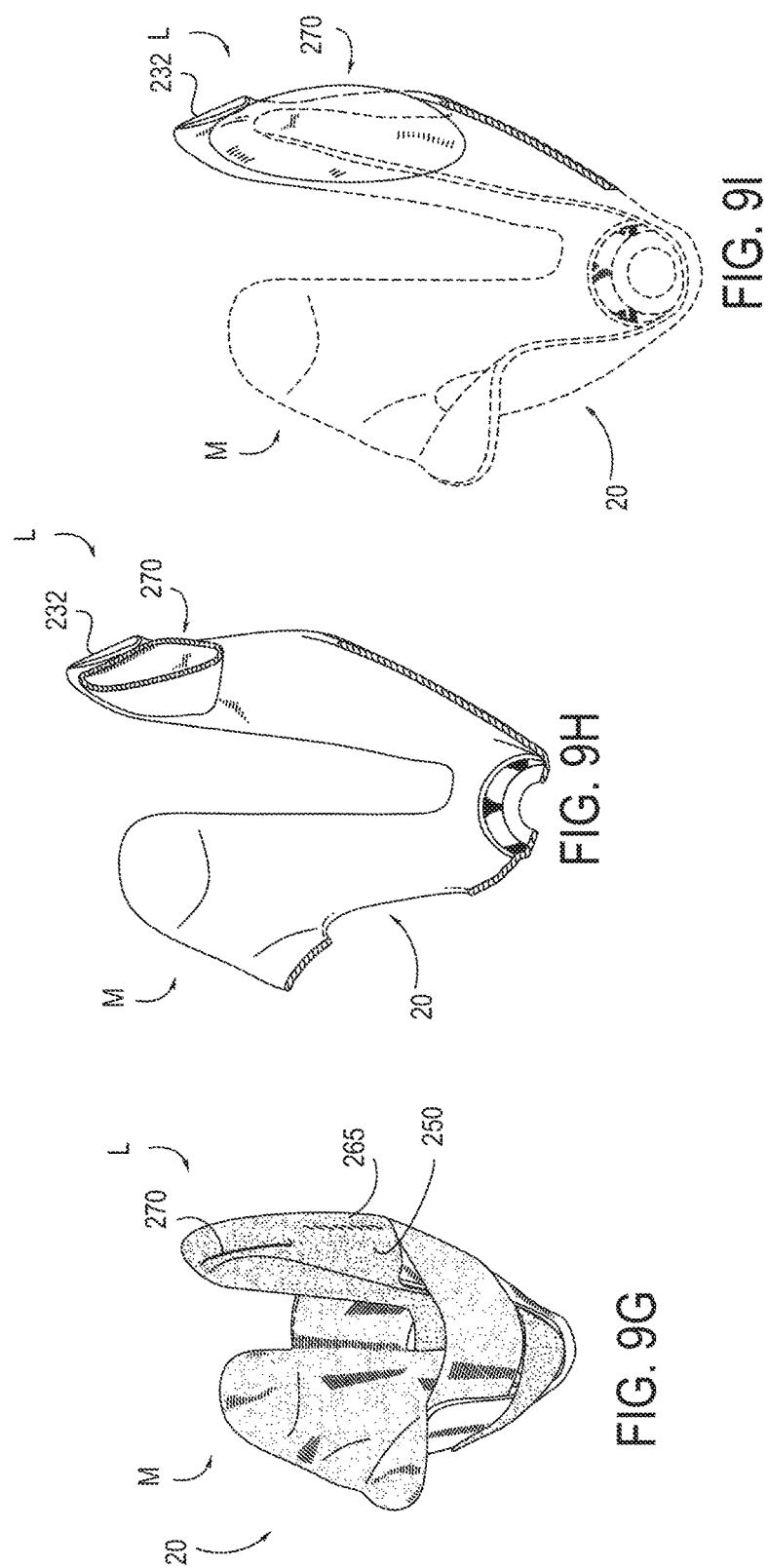

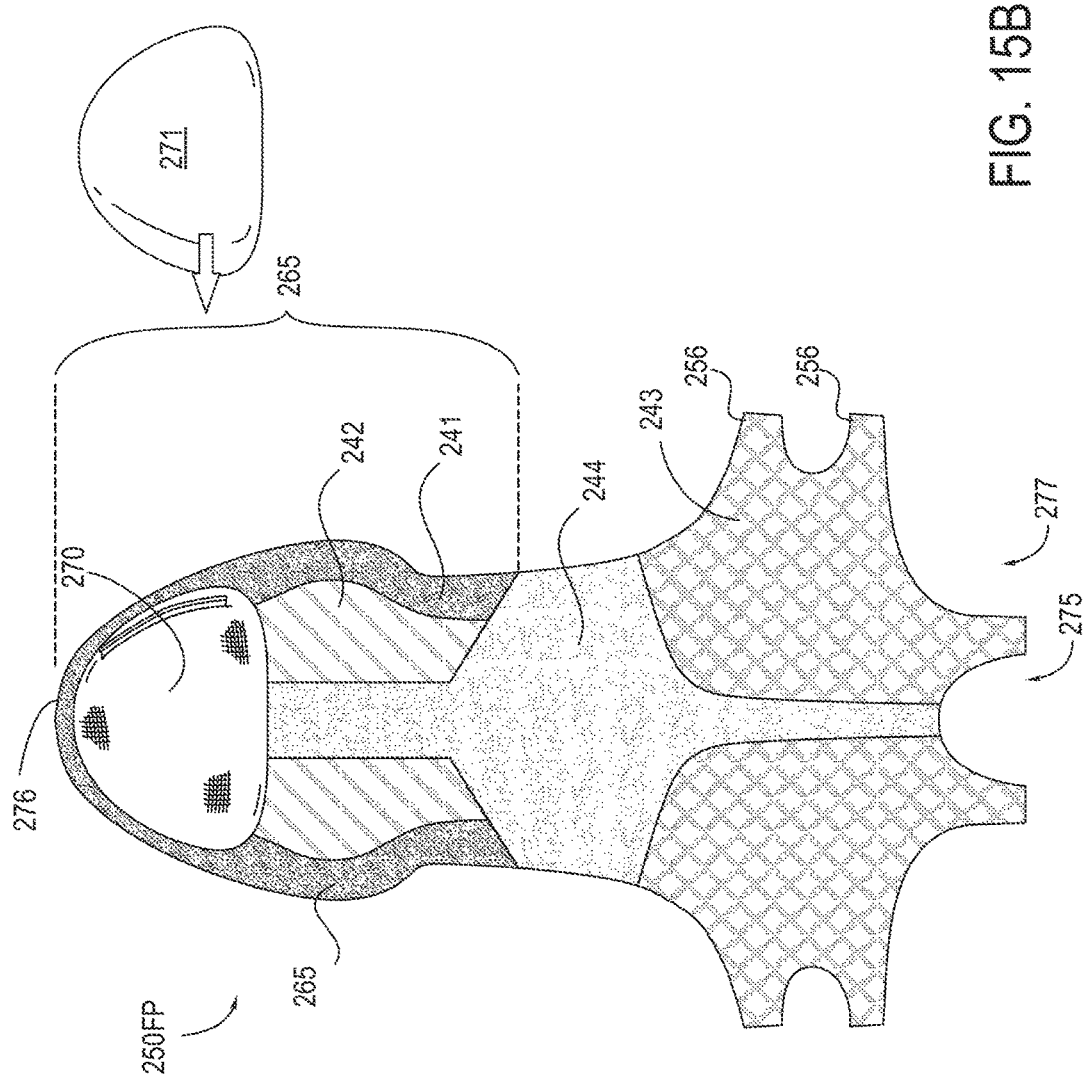

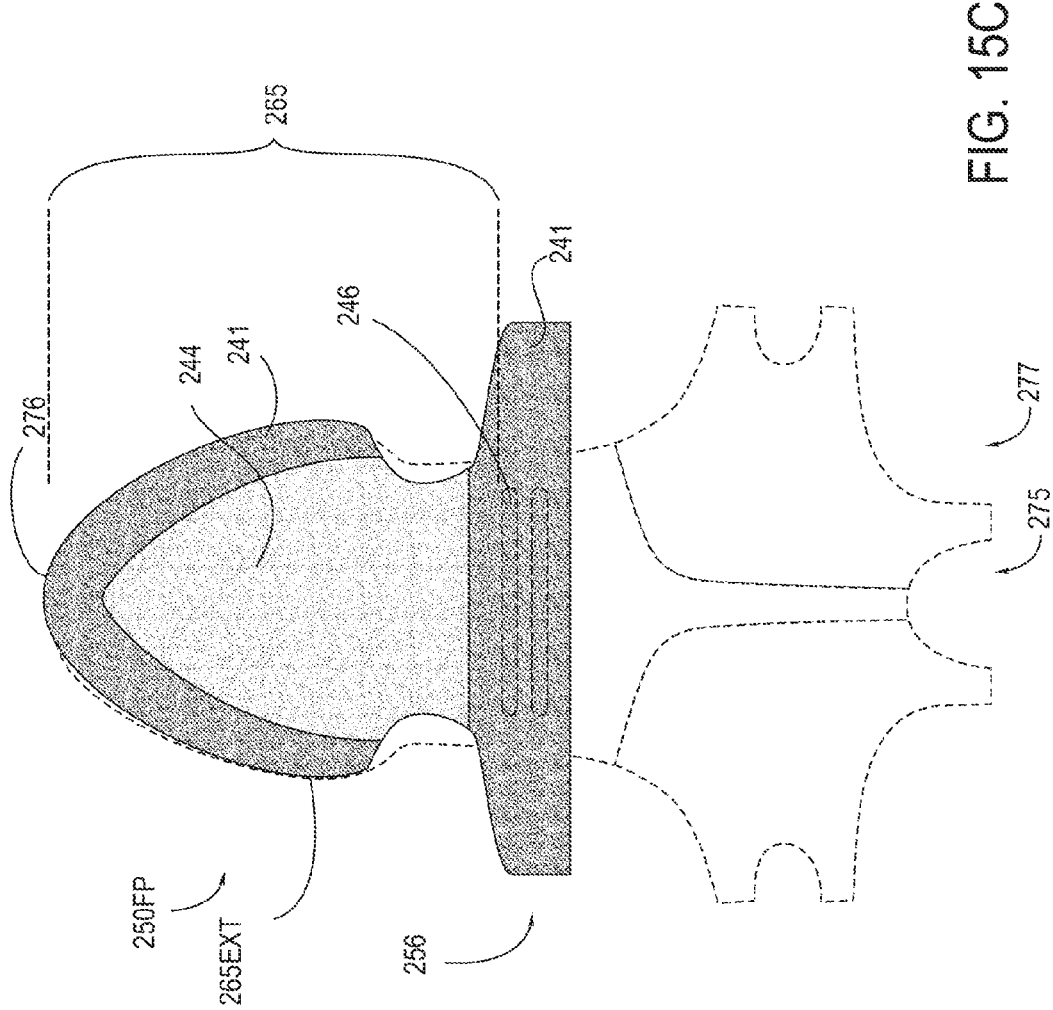

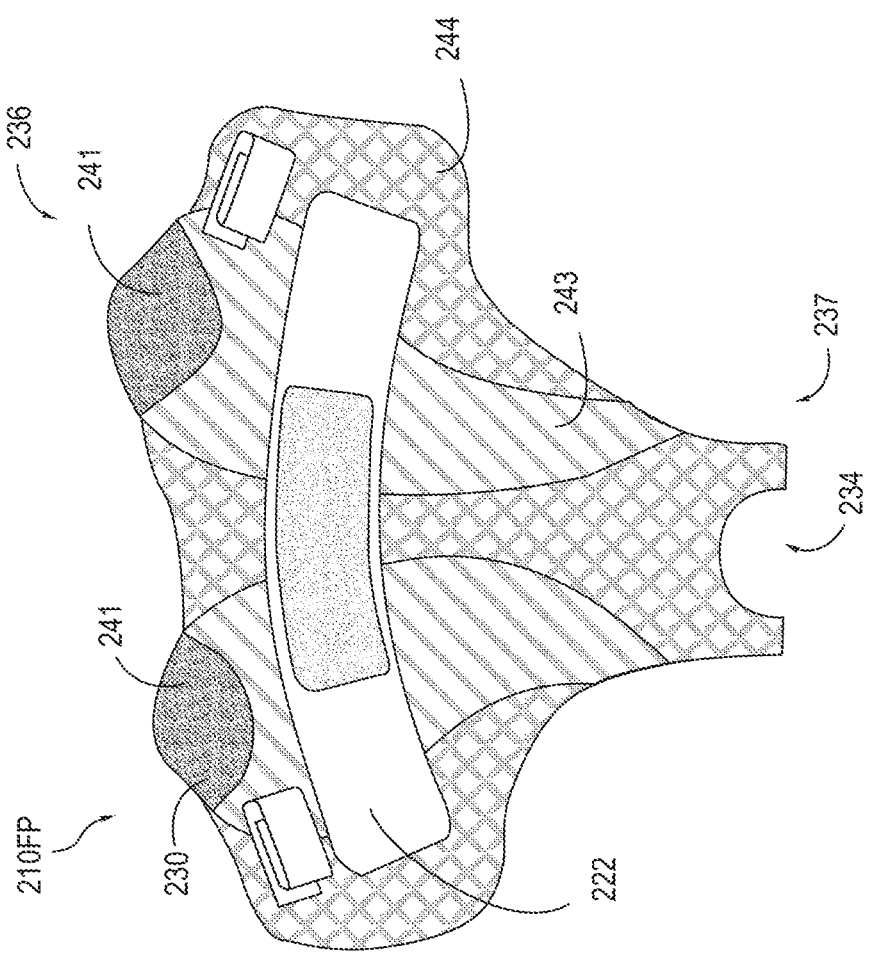

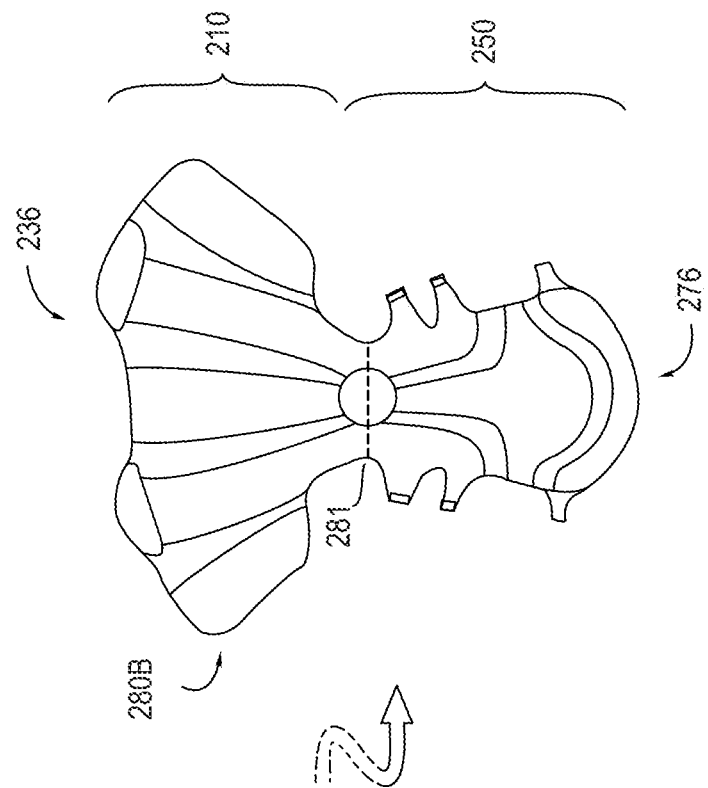
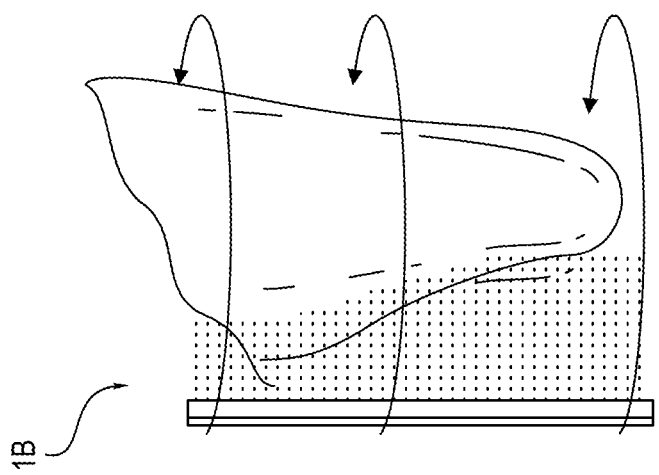
FIG. 17B

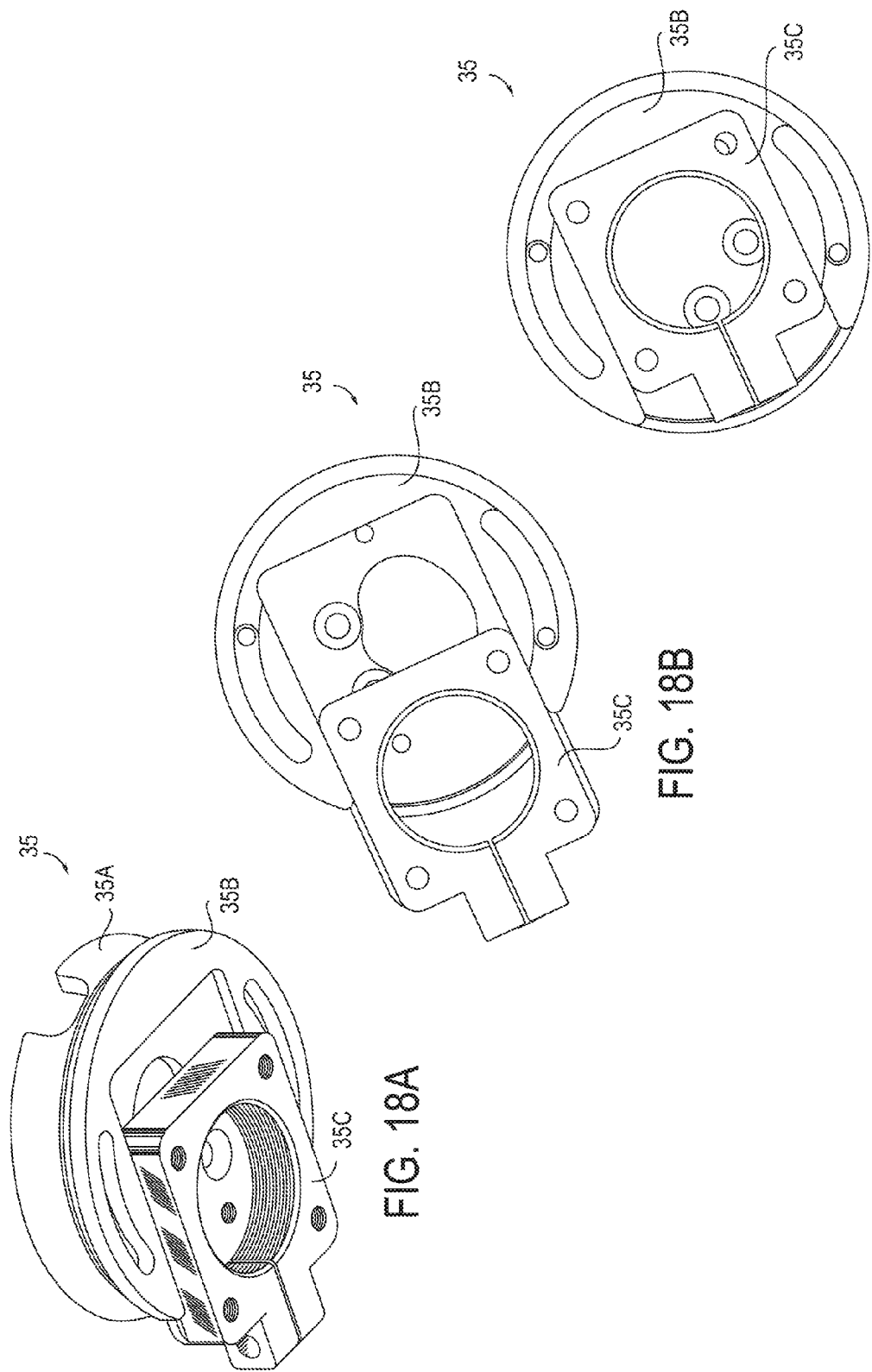

TRANSFEMORAL PROSTHETIC SOCKET WITH A TEXTILE-BASED COVER AND INTRA-FRAME FORCE APPLICATORS

CROSS-REFERENCE TO RELATED APPLICATIONS

This patent application claims priority to U.S. Provisional Patent Application Ser. Nos. 62/259,931 of Hurley et al., entitled "Prosthetic Socket with Positioning Sling," filed on Nov. 25, 2015; 62/287,702 of Hurley et al., entitled "Prosthetic Socket with Positioning Sling," filed on Jan. 27, 2016; and 62/305,477 of Hurley et al., entitled "Prosthetic Sockets with Textile-based Cover and Intra-frame Force Applicators," filed on Mar. 8, 2016. The full disclosures of all of the above-referenced patent applications are hereby incorporated by reference herein.

INCORPORATION BY REFERENCE

All publications and patent applications identified in this specification are herein incorporated by reference to the same extent as if each such individual publication or patent application were specifically and individually indicated to be so incorporated by reference.

TECHNICAL FIELD

This disclosure relates to medical devices and methods. More particularly, the disclosure relates to a prosthetic socket frame and a sling suspended internally within the frame to interface with, and apply force against, the residual limb.

BACKGROUND

Prosthetic limbs for the lower extremities typically include a residual limb socket, an alignment system, and distal prosthetic components to complete the limb. The prosthetic socket is the portion of the prosthesis designed to fit on the residual limb, grasp it securely, and provide the functional connection to the distal components. If the prosthetic socket does not fit properly, it will inevitably be uncomfortable for the patient, even to a level of intolerability. Even the most advanced prosthetic limb components distal to the socket will not serve the patient well, if the socket fits poorly. Ultimately, the prosthetic socket needs to enable the patient to efficiently translate her or his functional intention into functional actuality, by way of the prosthetic limb components distal to the prosthetic socket.

Aside from the universal issues of fit, comfort, and functionality, the amputee population is diverse in many ways, and there is thus a demand in the market for diversity in the types of prosthetic sockets. Diversity in the population of patients follows from conventional demographic variables, such as body weight, age, K-level, and individual levels of activity and personal preferences. It is also common for amputee patients to have more than one prosthetic socket, as well as more than one set of distal prosthetic components, which they use according to the specifics of activity in which they are engaged. The Infinite Socket™ system of LIM Innovations, Inc. (San Francisco, Calif.) is an example of a transfemoral (TF) prosthetic socket that is able to fit many patients, due to its modular assembly, its numerous adjustable features, and its use of thermoplastic fiber composite materials that permit a thermal reforming of components to optimize fit.

No matter how advanced the design, components, or materials, any prosthetic socket still involves a tradeoff between (a) versatility/adjustability and (b) increased complexity, weight, and bulk. A complement to a prosthetic socket with such options as possessed by the Infinite Socket™ system could thus be a socket with a narrower range of adjustable hardware options, but with an overall leaner profile that could be attractive to many patients, as, for example, those who engage in high performance activity.

Protecting the distal end of the residual limb from having to bear the load of the body weight of the patient is a particular challenge in the fitting of a prosthetic socket. The distal end of an amputated bone lacks the condyle of an intact bone, which, when intact, enables durable and functional load bearing. Thus, it is desirable for a prosthetic socket to spare the distal end of the residual limb from such load bearing by distributing the load elsewhere. In one approach, compression of the socket around the residual limb is helpful, in that it can distribute load away from the distal end of the residual limb and across a larger surface area of the residual limb through points of contact with the socket. In another approach, load can be distributed toward the most proximal region of the socket, where an appropriately contoured brim element can absorb load, transferring it away from the residual limb itself and onto the pelvis.

Still, protecting the distal end of the residual limb from having to bear the load of the body weight of the patient, even if done well, may not fully enable the functional optimization that might be desirably provided by a prosthetic socket. The residual limb is not a monolithic structure; the bones are not firmly locked within muscle like concrete, and the muscles themselves have a degree of movement independence from each other. Compression of the residual limb by a prosthetic socket may create a firmness of the limb as a whole, but it does not transform the residual limb into a monolithic structure. Further, excessive compression is not tolerated well for prolonged periods by patients, and it can bring a host of undesired effects. In addition to challenges associated with load distribution, the residual limb is missing its former distal portion, which normally acts to provide biomechanically intelligent leverage through that portion of the limb, and to stabilize the position of the upper portion of the limb as it connects to the body through the hip.

Despite the very significant advances made by the Infinite Socket™ system, additional improvements in prosthetic sockets are still being sought. It would be ideal, for example to have a prosthetic socket with improved ability to distribute forces placed on the residual limb as it is hosted within the socket in a biomechanically appropriate and normalizing manner. At least some of these objectives will be met by the embodiments described below.

SUMMARY

The present disclosure describes innovative residual limb fabric-based positioning slings, which are used in prosthetic socket frames, particularly transfemoral (TF) prosthetic socket frames. While these positioning slings are used with a prosthetic socket frame, they exert their positional action by way of the application of forces within the interior of the frame. Whatever forces the prosthetic socket may be exerting on a hosted residual limb, the forces exerted by positional slings are not exerted by way of the frame, but rather by way of forces generated within the frame. Various embodiments are directed to positioning slings, sets of slings, and methods of positioning and stabilizing a residual limb within a prosthetic socket by way of the slings.

In one aspect of the present disclosure, an intra-frame force applicator operates within the interior of a prosthetic socket frame. In one embodiment, an intra-frame force applicator takes the form of a fabric based positioning sling for a prosthetic socket. Such a positioning sling includes a fabric or textile body that includes a residual limb interfacing or force application portion adapted to be disposed within a prosthetic socket frame, one or more proximal suspension portions adapted to suspend from a proximal aspect of a prosthetic socket frame, and a tensioning system applicable to the sling as a whole. When disposed within a prosthetic socket frame, the fabric body of a sling is arranged as a longitudinally aligned tube, including an open proximal end and a closed distal end. The sling has a first longitudinal side having one or more proximal suspension portions and a second longitudinal side, opposite the first longitudinal side, the second longitudinal side having the residual limb interfacing portion of the sling. When the tensioning system is tensioned, the sling is arranged and configured to be pulled toward the first longitudinal side of the prosthetic socket frame.

The prosthetic socket generally includes a first longitudinal side corresponding to the first longitudinal side of the sling and a second longitudinal side corresponding to the second longitudinal side of the sling, the first and second longitudinal aspects being circumferentially opposite each other. Typically, positional slings are arranged across opposite longitudinal sides of a socket, for example, a sling can be arranged across lateral and medial sides of a prosthetic socket, or across anterior and posterior aspects of a prosthetic socket. For orientation and clarification of terminology that will be used below, a sling embodiment will be identified as either a medial sling, a lateral sling, an anterior sling, or a posterior sling, according its second longitudinal side (i.e., the limb interfacing or force application portion of the sling, or the side of the residual limb that is supported by the sling). Notably, however, by tensioning, the sling is drawn toward the first longitudinal side of the frame. Embodiments of these intra-frame positioning slings may be rigged within either a transfemoral (TF) prosthetic socket frame or a transtibial (TT) prosthetic socket frame.

In some embodiments, the fabric body of the intra-frame positioning sling further includes a distal anchoring portion adapted to be secured to a distal site within a cavity of the prosthetic socket frame, and a tensioning system.

Typical embodiments of a prosthetic socket frame (into which a positioning sling is arranged) have a central cavity with a distal interior end, and in some of the embodiments of a positioning sling, the second longitudinal side of the positioning sling, when disposed within the prosthetic socket frame, is free floating or unattached to the frame.

In some embodiments, the tensioning system is configured to control an application of generally circumferentially distributed and centripetally directed compressive force by the sling on the residual limb. In particular examples of these embodiments, the tensioning system is, at the same time, configured to control an application of horizontal force on the sling toward the first longitudinal side of the prosthetic socket frame.

In some embodiments, the residual limb interfacing portion of the sling fabric piece includes two or more regions that vary with regard to elasticity, as for example, being any of elastic or inelastic. If elastic, a region may be any of elastic throughout 360 degrees, without an elasticity bias, or the elasticity may be directionally biased. In one example of a biased elasticity, the sling fabric may be elastic horizontally and substantially inelastic vertically, these directions per orientation of the fabric when the sling is rigged in a prosthetic socket. When being worn by a patient, in some embodiments of a positional sling, the regions of the sling that vary in elastic properties create or effect corresponding regions of varying pressure on the residual limb.

By way of example, the composition of fabric of slings may include natural fibers or synthetic fibers, or any combination thereof. An example of a suitable synthetic fiber includes polyester-polyurethane copolymers, referred to by brand names such as Spandex, Lycra, or Elastane. In typical sling embodiments, a polyester-polyurethane copolymer is the dominant fabric within the sling, which can be produced in a wide variety of weaves and with varying degrees of elasticity. The dominant fiber may also be used as a substrate that can be layered upon with other materials.

In some embodiments, the fabric includes layered sections or features. For example, in addition to regions that vary in aspects of elasticity, the fabric of slings may include any of layer of thermoplastic, a layer of thermoplastic with embedded fiber (i.e., a thermoplastic-fiber composite), and/or a layer of adhesive, such as a heat-activatable adhesive. Inclusion or integration of a thermoplastic layer has the effect of structuralizing an otherwise freely draping fabric. In one example, a fabric may include an inner layer having thermoplastic-fiber composition and heat activated adhesive backing and an outer fabric layer. A thermoplastic or thermoplastic-fiber composition is advantageously strong and durable, has a low surface friction, and is adaptable to varied types of construction, easy to handle and trim, comfortable against the body, and amenable to seamless transitioning to fabric regions of other composition. More particularly, a thermoplastic or thermoplastic-fiber composition is amenable to custom molding, and in particular, to post-production custom molding to optimize fitting to a patient or to optimize fitting to a structural frame.

Molded thermoplastic fabric portions can be mass-produced as units of varying size and shape in a modular approach, and can be integrated into a sling pattern and construction with stitch flanges and/or integrated with prosthetic socket frame hardware. In this context, molded thermoplastic fabric portions can be used to seamlessly transition pressure distribution between the structural frame and fabric portions of a positional sling. This approach to integrating molded thermoplastic pieces with fabric also allows for that portion of the fabric to be custom-made or custom-altered, yet maintain an engineered structure to affix the fabric sling to the structural frame.

In some embodiments of the intra-frame positioning sling for a prosthetic socket, the residual limb-interfacing portion of the sling fabric piece includes one or more pockets configured to accommodate a shim. And in particular embodiments, the one or more pockets has a shim disposed therein. Such arrangements, as with the variable elastic regions noted above, can create or effect corresponding regions of varying pressure on the residual limb.

In some embodiments, the tensioning system is arranged such that is anchorable to the first longitudinal side of the prosthetic socket frame and includes attachment features that draw parallel portions of the fabric piece together along the first longitudinal side of the prosthetic socket frame. Such embodiments further include at least one tensionable circumferentially continuous path that extends around the second longitudinal side of the sling, this tensionable path being disposed internally within all structural aspects of the second longitudinal side of the prosthetic socket frame.

Some embodiments may also include one or more sensors disposed on the prosthetic socket hosting the intra-frame positioning sling, or on the fabric body of the sling, or positioned at a site the interfaces between the socket frame and the sling, such sensors including, merely by way of example, any one or more of a pressure sensor, a tension sensor, a motion sensor, a global positioning sensor, or a Hall effect sensor. In such embodiments, one or more sensors may be positioned in a longitudinal force transfer path within the prosthetic socket, wherein the one or more sensors is configured to transmit sensing signals to a data receiver.

In another aspect, a set of two intra-frame positioning slings for a prosthetic socket may include a set of two slings, a medial sling and a lateral sling. These embodiments may be particularly appropriate for a transfemoral (TF) prosthetic socket. Each of the two slings may include a fabric piece including a residual limb interfacing portion adapted to be disposed within a prosthetic socket frame, one or more proximal suspension portions adapted to suspend from a proximal aspect of a prosthetic socket frame, and a tensioning system. When disposed within a prosthetic socket frame, each positioning sling is arranged as a longitudinally aligned tube including an open proximal end and a closed distal end.

The medial sling of this embodiment includes a lateral side having the one or more proximal suspension portions and a medial side having the residual limb interfacing portion of the medial sling, free floating within the prosthetic socket cavity; and when the tensioning system is tensioned, the medial sling is pulled toward the lateral side of the prosthetic socket frame.

The lateral sling of this embodiment includes a medial side having the one or more proximal suspension portions and a lateral side having the residual limb interfacing portion of the medial sling, free floating within the prosthetic socket cavity; and when the tensioning system is tensioned, the lateral sling is pulled toward the medial side of the prosthetic socket frame.

In some embodiments, the tensioning system of the medial sling and the tensioning system of the lateral sling are operable independently of each other. And in some embodiments, the set of two intra-frame positioning slings, the medial sling and the lateral sling are cooperatively operable to balance lateral-ward and medial-ward forces to support the residual limb centrally within the prosthetic socket frame.

In some embodiments, the lateral sling is tensionable toward the medial side of the prosthetic socket at two longitudinally positioned sites, a proximal site and a distal site, and the medial sling is tensionable toward the lateral side of the prosthetic socket at a longitudinally central site, between the proximal and distal sites of the lateral sling.

In some embodiments, the two longitudinally positioned tensioning sites of the lateral sling and the longitudinally central site of the medial sling provide a 3-point residual limb stabilizing arrangement within the prosthetic socket frame.

In another aspect of the disclosure, a method of stabilizing or positioning a residual limb of a patient within a transfemoral (TF) prosthetic socket is described. The method may include resisting a horizontal vector applied to a longitudinal side of the residual limb within the prosthetic socket frame, the horizontal vector being generated by the patient, whether the patient is engaging in activity, standing or resting. Resisting the horizontal vector includes applying one or more counteractive horizontal vectors on one or more longitudinal sides of the residual limb from within the prosthetic socket frame by way of tensioning one or more positioning slings disposed within the prosthetic socket frame.

In some embodiments, in which the residual limb is a residual thigh, applying a counteracting one or more horizontal vectors includes applying any of a laterally directed horizontal force vector against the residual thigh and applying a medially directed horizontal force vector against the residual thigh.

In some embodiments, applying a medially directed horizontal force vector to a lateral side of the residual thigh occurs at one or more sites along the medial side of the residual thigh.

In some embodiments of this mehod, applying a laterally directed horizontal force vector to a medial side of the residual thigh occurs at a site along the medial side of the residual thigh.

In some embodiments, applying a laterally directed horizontal force vector to a medial side of the residual thigh occurs at a midpoint on the residual thigh, and applying a medially directed horizontal force vector to a lateral side of the residual thigh occurs at any of a proximal aspect or a distal aspect of the residual thigh.

In some embodiments, when the prosthetic socket includes a lateral sling and a medial sling, and when tensioning both the lateral sling and the medial sling, a set of three horizontal vectors is applied against the residual thigh, the three horizontal vectors including a laterally directed force vector created by the medial sling, and two medially directed force vectors created by the lateral sling.

In yet another aspect, a method directed to stabilizing or positioning a residual limb of a patient within a transfemoral (TF) prosthetic socket may involve applying a laterally directed horizontal force vector to a longitudinal side of the residual limb within the prosthetic socket frame, and applying two medially directed horizontal vectors to a longitudinal side of the residual limb within the prosthetic socket frame.

In some embodiments, stabilizing a residual limb of a patient within the TF prosthetic socket includes applying a laterally directed horizontal force vector to a longitudinal side of the residual limb within the prosthetic socket frame created by way of tensioning a medial sling rigged within the TF prosthetic socket, and applying two medially directed horizontal vectors to a longitudinal side of the residual limb within the prosthetic socket frame created by way of tensioning a lateral sling rigged within the TF prosthetic socket.

In another embodiment, applying a laterally directed horizontal force vector to a longitudinal side of the residual limb within the prosthetic socket frame created by way of applying leverage against a residual femur within the residual limb, and applying two medially directed horizontal vectors to a longitudinal side of the residual limb within the prosthetic socket frame created by way of applying leverage against the residual femur within the residual limb.

In yet another aspect of the disclosure, a sling system for supporting a residual limb within a frame of a prosthetic socket may include a first sling and a second sling. The first sling may include a first end attached to a proximal end of a first side of the frame of the prosthetic socket, where the first sling extends down the first side, forms a curved portion near a distal end of the frame, and extends partway up an opposite second side of the frame to a second end of the first sling. The second sling may include a first end attached to a proximal end of the second side of the frame, where the second sling extends down the second side, forms a curved portion near the distal end of the frame, and extends partway up the first side of the frame to a second end of the second sling. In some embodiments, the second end of the first sling and the second end of the second sling are configured to float relative to the frame of the prosthetic socket when the first end of the first sling and the first end of the second sling are attached to the frame.

In yet another aspect of the disclosure, a sling system for supporting a residual limb within a prosthetic socket cavity defined by a prosthetic socket frame may include a first sling and a second sling. The first sling may include a first suspension portion suspended from a proximal end of a first side of the prosthetic socket frame and a first tensioning portion comprising two arms that extend in both directions around an interior aspect of the prosthetic socket cavity, the two arms of the first sling meeting each other at a first anchoring site on the second side of the frame, opposite the first side of the frame, where the first anchoring site includes a first tensionable coupling mechanism. The second sling may include a second suspension portion suspended from a proximal end of the second side of the prosthetic socket frame and a second tensioning portion comprising two arms that extend in both directions around an interior aspect of the prosthetic socket cavity, the two arms of the second sling meeting each other at a second anchoring site on the first side of the frame, where the second anchoring site may include a second tensionable coupling mechanism.

In some embodiments, when the first sling is tensioned by first tensionable coupling mechanism, the first sling is drawn toward the second side of the prosthetic socket cavity. In some embodiment, when the second sling is tensioned by second tensionable coupling mechanism, the second sling is drawn toward the first side of the prosthetic socket cavity.

These and other aspects and embodiments are described in further detail below, in reference to the attached drawing figures.

BRIEF DESCRIPTION OF DRAWINGS

FIGS. 1A-1D are side views of a transfemoral (TF) prosthetic socket frame, according to one embodiment, where FIG. 1A is a medial view, FIG. 1B is a posterior view FIG. 1C is an anterior view, and FIG. 1D is a lateral view;

FIG. 1E is a top view of the prosthetic socket frame of FIGS. 1A-1D;

FIG. 1F is a posterior perspective view, FIG. 1G is an anterior-lateral perspective view, and FIG. 1H is a posterior-lateral perspective view;

FIG. 1K is a schematic top view of an embodiment of a TF prosthetic socket frame that clarifies strut positioning with respect to anterior-posterior and lateral-medial reference terminology;

FIG. 4A is a cross-sectional view of a residual thigh as in FIG. 3B, further showing a tensioning system element of a medial sling anchored on a lateral anchoring site around an external aspect of the hosting TF prosthetic socket frame, the tensioning mechanism in an un-tensioned state, according to one embodiment;

FIG. 4B is a top view of the TF prosthetic socket arrangement seen in FIG. 4A (absent the residual thigh 1);

FIG. 4C is a cross-sectional view of a residual thigh as shown FIG. 4A, with the tensioning mechanism now in a tensioned state;

FIG. 4D shows a top view of the arrangement see in FIG. 4C absent the residual thigh;

FIG. 5A is a cross-sectional view of a residual thigh as in FIG. 3B, further showing a tensioning system element of a lateral sling anchored on a lateral anchoring site of the hosting TF prosthetic socket frame, the tensioning mechanism in an un-tensioned state;

FIG. 5B is a top view of the arrangement seen in FIG. 5A.

FIG. 5C is a view of a residual thigh as shown FIG. 5A, in with the tensioning mechanism now in a tensioned state;

FIG. 5D is a top view of the arrangement see in FIG. 5C;

FIG. 7A is an anterior side view of a TF prosthetic socket, focusing in particular on the externally visible portions of the tensioning systems of both the medial and lateral slings, according to one embodiment;

FIG. 7B is an anterior side view of a TF prosthetic socket that includes a tensioning or constraining strap that is inserted through slots in the proximal portion of adjacent lateral and medial struts, according to one embodiment;

FIG. 7C is an anterior view of an embodiment of a TF prosthetic socket frame, without medial or lateral slings, showing only the constraining strap disposed between neighboring pairs of lateral and medial struts, the struts positioned relatively wide apart across an intervening cleft, according to one embodiment;

FIG. 7D shows an embodiment of a TF prosthetic socket similar to that of FIG. 7C, in which the neighboring lateral and medial struts are positioned relatively close together across an intervening cleft;

FIG. 8A shows a medial view of an embodiment of a TF prosthetic socket frame;

FIG. 8B shows a medial view of an embodiment of a lateral sling, as seen in an orientation like that of the TF prosthetic socket of FIG. 8A, according to one embodiment;

FIG. 8C shows the lateral sling of FIG. 8B rigged into the TF prosthetic socket of FIG. 8A, according to one embodiment;

FIG. 9G is a medial view of a TF prosthetic socket frame with a lateral sling rigged therein, the lateral sling having a pad or shim insertion pocket on the internal side of its proximal portion, according to one embodiment;

FIG. 9H shows a cutaway view of the proximal half of a TF prosthetic socket frame, showing, in particular, the position of the pad or shim insertion pocket with respect to the frame, as shown in FIG. 9G;

FIG. 9I shows a ghosted view of a complete TF prosthetic socket frame, showing, in particular, the position of the pad or shim insertion pocket with respect to the frame, as shown in FIG. 9G;

FIG. 15B shows an internal view of an embodiment of flat pattern for a lateral sling as in FIG. 15A, but further showing a shim pocket on the internal surface of the proximal portion of the pattern;

FIG. 15C shows an external view of an embodiment of a flat pattern for a lateral sling, focusing particularly on a proximal suspension pocket portion and horizontally disposed tensioning straps;

FIG. 16B shows an external view of an embodiment of a flat pattern for a medial sling as in FIG. 16A, but further showing a horizontally disposed tensioning strap;

FIG. 17B shows a conical residual limb (left panel of FIG. 17B) and a conjoined (medial plus lateral) sling flat pattern accordingly configured to accommodate the conical limb (right panel of FIG. 17A);

FIGS. 18A-18C show a distal base alignment assembly suitable for application to a TF prosthetic socket frame as provided herein. FIG. 18A shows a bottom perspective view of a distal base;

FIG. 18B shows a bottom face view of a distal base and alignment assembly in an extended alignment position; and FIG. 18C shows a bottom face view of a distal base and alignment assembly in a neutral alignment position.

DETAILED DESCRIPTION

Overview of Intra-Frame Positional Slings

Figure 1H:
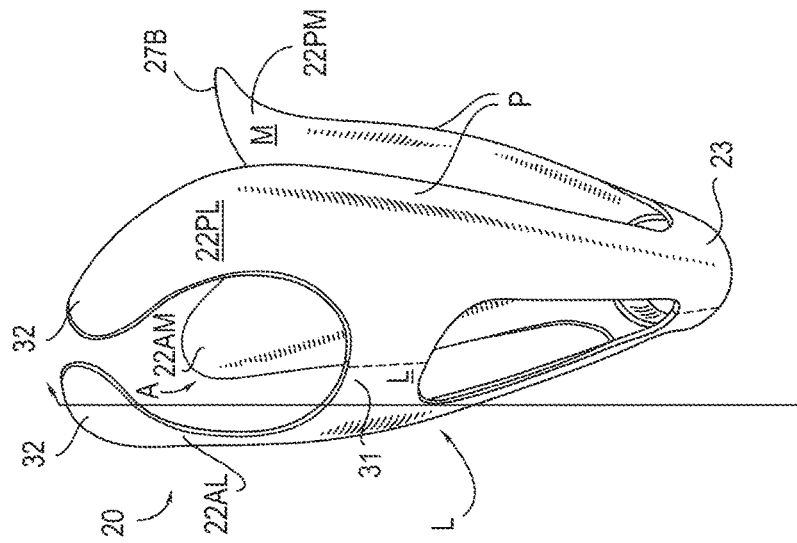
FIGS. 1F-1H are perspective views of a TF prosthetic socket frame, according to one embodiment, where
Figure 1G:
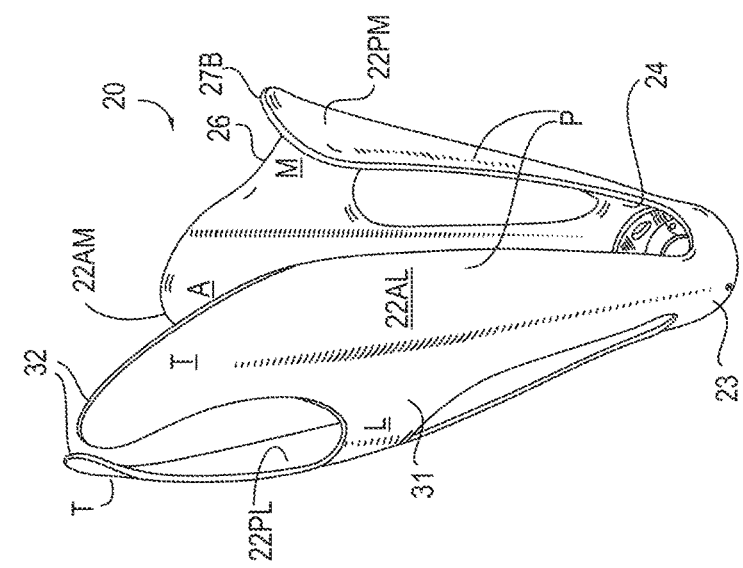
Figure 1F:
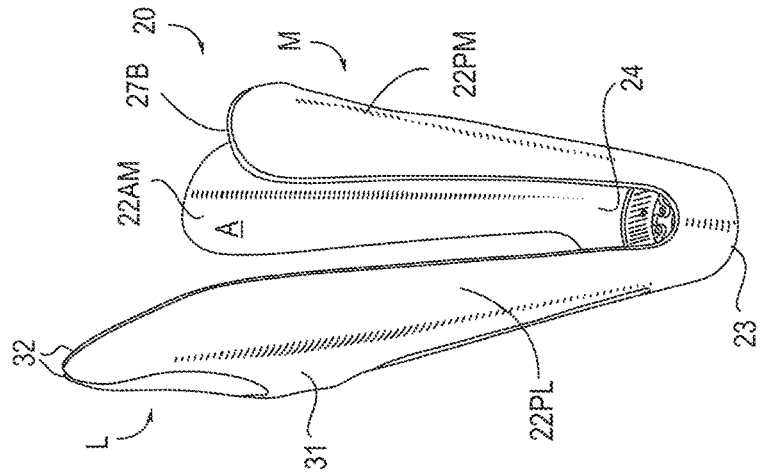
Figure 1J:
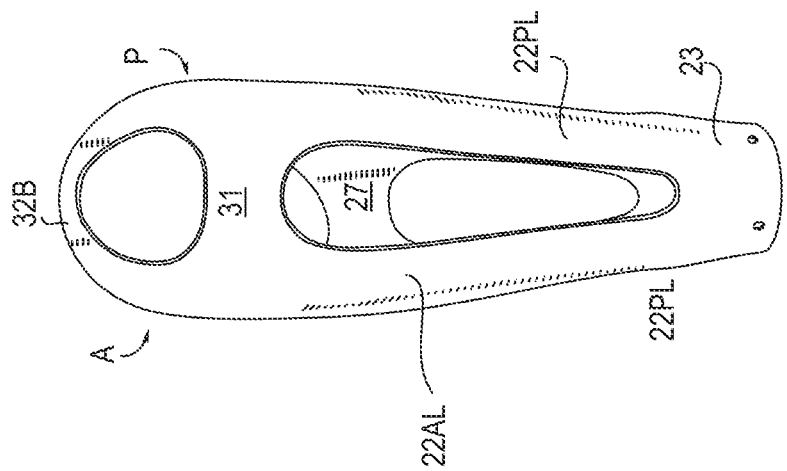
FIGS. 1I and 1J are medial and lateral views, respectively, of a TF prosthetic socket frame in which trochanteric extensions of lateral struts are proximally conjoined, according to an alternative embodiment.

Various embodiments of intra-frame force applicators for prosthetic sockets are described in this application, typically embodied as positional slings, which are suitable for suspending within a prosthetic socket. Typical intra-frame positional sling embodiments are actuatable, being responsive to circumferential tensioning or horizontally applied force vectors. Any reference to an embodiment of a "sling" or "a set of slings" herein, refers to such an intra-frame positional sling. "Intra-frame" refers to the positioning of these sling embodiments within the cavity of a structural frame of a prosthetic socket. "Positional" refers to aspects of sling functionality that are directed toward positioning the residual limb within the socket frame. More generally, slings may be considered "intra-frame force applicators," a term that refers to the fact that force is being delivered from within the frame.

Intra-frame force applicators are typically anchored by an external prosthetic socket frame, but their exerted forces are separate from any force that the frame, itself, may be transmitting to the residual limb. While positional slings exert their positioning forces (generally horizontal vectors and circumferential compression) from within a prosthetic socket frame, they do have an aspect that is external to the frame, and visible externally. These external aspects, such as external portions of a suspension pocket, function as a prosthetic socket cover.

Slings may be further understood as biomechanical stabilizing devices for a residual limb, and, more particularly, devices for stabilizing the residual bone within the residual limb. Slings may function by way of resisting forces, such as abductive force, to which the residual limb is vulnerable, particularly during ambulation. Sling embodiments may also function as force application devices, applying forces on the residual limb to counter the destabilizing forces that develop during ambulation.

It may be helpful to consider aspects of the biomechanics of range of motion of a joint, and apply these concepts functionally to the role of positioning slings within a prosthetic socket frame. In the body, there is a hard stop to the range of motion when bone contacts bone, as for example, in passive elbow extension, when the olecranon process contacts the olecranon fossa. Typically, however, prior to encountering a hard stop to a range of motion, there are earlier end points, as may be generated by soft tissue opposition or stretch, or joint capsule stretch, and the associated sensations. These earlier end points are useful, in that they moderate movement within the full range of motion, stabilizing movement in a central area where most function occurs, and protecting the hard stop elements from overuse and injury. These nuances of the range of motion in a joint, particularly the end points of the range, can be functionally analogized to the range of movement or position of the residual limb within a prosthetic socket. The prosthetic socket frame provides a hard stop; softer stops are provided by oppositional forces and the resilient stretch of the tensioning elements and fabric of the positioning slings.

Sling embodiments are anchored on structural features of a prosthetic socket frame, but compressive or vectorial forces can be exerted by sling embodiments on a hosted residual limb separately, controllably, and independently of forces that may be exerted by the prosthetic socket frame, itself. This independence of action that sling embodiments are able to exert is related to them being arranged internally, within the socket.

Sling embodiments are configured to accommodate or host a residual limb of a patient, and are typically arranged and aligned longitudinally, within a prosthetic socket frame. The longitudinal alignment is supported by the alignment of sites on the sling adapted to attach to sites on the supporting prosthetic socket frame. As a whole, sling embodiments, as provided herein, represent the interfacing aspect of a prosthetic socket system against the surface of the residual limb or, more specifically, against a prosthetic gel liner that the patient may be wearing. Embodiments of prosthetic sockets with intra-frame positional slings rigged therein may be configured for both transfemoral (TF) amputated limbs, at any level, and for below knee, trans-tibial (TT) amputated limbs, at any level. Embodiments may further be configured and applied to supporting patients with other types of amputations, including knee disarticulation, ankle disarticulation, hip disarticulation, and all upper extremity amputations such as trans-radial, trans-humeral, wrist disarticulations, elbow disarticulations, and shoulder disarticulations.

Positional sling embodiments are typically arranged with an asymmetric orientation or bias with reference to a cross sectional coronal view of the hosted prosthetic limb and the hosting socket. Typically, a positional sling embodiment is anchored to one longitudinal side of a prosthetic socket frame and unattached on the (180-degree) opposite longitudinal side of the prosthetic socket frame. For example a positional sling embodiment may be unattached on a medial side of a prosthetic socket frame and anchored on a lateral side of the prosthetic socket frame. Positional sling embodiments may be oriented similarly with any 360-degree orientation, such as being unattached on lateral longitudinal side of a prosthetic socket frame and anchored on a medial side of the prosthetic socket frame. In another example, a sling embodiment may be unattached on an anterior longitudinal side of a prosthetic socket frame and anchored on a posterior longitudinal side of the prosthetic socket frame. In yet another example, a sling embodiment may be unattached on a posterior longitudinal side of a prosthetic socket frame and anchored on an anterior longitudinal side of the prosthetic socket frame.

As described herein, a medial positioning sling is one that exerts pressure on the medial size of a residual limb. This means that it is anchored on the lateral side of a prosthetic socket, and pulls the residual limb in a lateral direction.

As described herein, a lateral positioning sling is one that exerts pressure on the lateral size of a residual limb. This means that it is anchored on the medial side of a prosthetic socket, and pulls the residual limb in a medial direction.

Embodiments of systems or sets of prosthetic socket intra-frame positional slings may include one or more slings. By way of example, a prosthetic socket frame embodiment may be rigged with a single sling; that single sling may be anchored on a posterior longitudinal side of the frame and be unattached on the opposite anterior longitudinal side of the frame. In another example, a system or set of prosthetic socket slings may include two slings, a first sling and a second sling: the first sling being anchored on a lateral longitudinal side of the socket frame and unattached on the medial longitudinal side of the socket frame, while the second sling is anchored on a medial longitudinal side of the socket frame and unattached on the lateral longitudinal side of the socket frame. In typical sling set embodiments that include two slings, the two slings are independently operable by tensioning features, but are arranged so as to cooperate in their positioning of the residual limb within the prosthetic socket frame.

Sling embodiments typically have or include a fabric or textile composition. These sling compositions, being fabric based, are generally compliant and conformally wrap around a residual limb. However, there may be heterogeneity in various aspects of the sling composition, and which play out in a regional manner within the surface area of a sling, and which then have regional effect on a residual limb hosted therein. For example, regions of sling embodiments may vary in elasticity properties. Some regions may be highly elastic; other regions may be substantially inelastic. Elastic regions may be equally elastic in all directions across a surface area. Elastic regions may also have a biased elasticity, for example, as arranged in a sling, the fabric composition may be such that it is elastic in a horizontal direction, but substantially inelastic in a vertical direction.

In some sling embodiments, one woven elastic fabric composition is a dominant feature of the surface area. Even with a dominant fabric composition, some regions may include other fabric compositions, or other fabric layers may be applied to the dominant surface composition. In other sling embodiments, two or more fabric compositions may be in play to the degree that no single sling fabric composition dominates the surface area.

In some sling embodiments, regional variations in elasticity may be accounted for in terms of the weave and composition of a single elastic fabric composition. In other embodiments, regional variations in elasticity of the sling embodiment, as a whole, may be imparted to the sling by distinct, separate regions within the sling surface area, or, by layers of material, fabric or otherwise that are applied to a sling fabric substrate.

If the fabric composition of a sling were homogenous throughout its surface area, the application of compressive force throughout the interfacing area where the sling contacts the residual limb would be substantially uniform across the interface. However in some sling embodiments, as described above, the composition of the sling fabric across its surface area is heterogeneous, and at least some of that heterogeneity can have an effect on local application of compressive force visited on particular regionals of the residual limb. Indeed, the regional heterogeneity in sling fabric composition can be designed to create heterogeneity in compressive pressure as applied to regions of the residual limb. For example, if a region within the surface area of a sling embodiment that is substantially inelastic is proximate an surface area region that is highly elastic, the compressive force applied to a region of the residual limb that is aligned against the inelastic region of the sling will be greater than the pressure applied to a region aligned against the highly elastic region of the sling.

Sling embodiments may include further features that create local regions that differ with regard to internal pressure brought to bear corresponding regions of the residual limb. In one example of a regional feature that effects local pressure involves pockets within the fabric of the sling embodiment, into which hard, shaped insert pieces may be inserted. Although regions within the fabric of a sling embodiment may differ with regard to elasticity, the overall flexibility of regions differing in elasticity is substantially the same, and accordingly, the conformability of such regions against the residual limb is also substantially the same.

Embodiments of slings also may include pockets that accommodate insertion shims that broadly flat but with a central portion that is thicker than tapered peripheral edges. These insertion pieces are less flexible or compliant than the fabric of the sling into which they are inserted. The presence of hard, generally flat, peripherally tapered insertion shims within the sling cross sectional area disrupts the broad background of substantially identical conformability of the sling surface area, and depresses the region of the residual limb against which they are aligned below the surface of the surrounding, fabric-covered region of the limb. Insertion shims thus can create regions of higher inwardly directed compressive force. As with the differentially compressive regions provided by differential elasticity, the localized application of compressive force created by insertion shims can be applied, by design, to regions of the residual limb where such increased compressive force is desired, and which can provide biomechanical advantages in the fitting and functionality of the prosthetic socket as a whole.

Some embodiments of the positional slings provided herein are "custom-fitted" to a patient, i.e., there is a high degree of fidelity between the dimensions and contours of the sling and the dimensions and contours of the patient's residual limb. Slings that are custom-fitted to a patient, per embodiments of the invention, may be arrived at by at least two approaches that play out in the context of sling flat patterns. Flat patterns, per embodiments of the invention, may be unitary or include sub-patterns that are assembled together to create a whole sling pattern.

In a first approach, the sling is entirely custom made (made specifically for an individual patient, based on a digital profile of the relevant body portion). In a second approach, the flat pattern of the sling (including any sling sub-component patterns) is available in the form of a highly diverse inventory. The inventory may include an actual physical inventory, or it may exist in a virtual or digital sense, or a just-in-time physical inventory sense, wherein flat patterns or component patterns can be matched to the three dimensional dimensions and contours of a patient's residual limb.

Both custom-fitting approaches typically involve acquisition of a digital profile of the residual limb, followed by application of algorithms that translate the digital profile into dimensional variations within a basic common flat pattern design. In the instance of custom-fitting a sling to a residual limb that takes advantage of either a physical or virtual inventory, algorithms translate the residual limb digital profile into choices available within the inventory. In the instance of custom-making a sling, algorithms direct data from the residual limb profile into driving particular dimensional choices that are applied to a common flat pattern that includes these particular dimensions within a range of options.

TF Frame and Positional Sling Embodiments

Turning now to aspects of the invention with a focus: the TF prosthetic embodiments described herein include a TF prosthetic socket structural frame, embodiments of a set of positioning slings configured to be rigged within a TF prosthetic socket, and an embodiment of a prosthetic socket system that includes a TF prosthetic socket embodiment fully rigged with an embodiment of a set of positioning slings. Distances and differences in configuration of TF prosthetic frames and slings disposed therein are not necessarily drawn to scale. In some instances, relationships between frame and sling may be exaggerated in a pictorial sense compared to the actuality; the purpose of this is simply to facilitate communication of the nature of the invention.

Embodiments of a transfemoral (TF) prosthetic socket 20, as provided herein, include a socket frame, to be described in detail now, and a set of positioning slings to be described in detail further below. As shown variously in FIGS. 1A-18C, for simplicity, a TF prosthetic socket will be identified by label 20 when it is being depicted or described as any of a structurally complete frame, any portion of a frame, a frame rigged with a single positional sling, or a frame rigged with two positional slings. TF prosthetic socket frame 20 may be understood as having four faces or sides (without reference to any particular structure): an anterior face A, a posterior face P, a lateral face L, and a medial face M. In identifying the four struts individually, the labeling code has two letters: the first letter refers to either anterior A or to posterior P. The second letter refers either to lateral L or to medial M. These anterior, posterior, lateral, and medial face labels (A, P, L, M) are used for spatial orientation in FIGS. 1A-14B)

As shown in FIG. 1K, TF prosthetic socket frame 20 includes a set of multiple longitudinal struts 22 that may be categorized as a pair of medial struts 22M and a pair of lateral struts 22L, according to their anatomical location with reference to a patient's residual limb when being worn by the patient. Prosthetic frame 20 thus includes four struts: posterior medial strut 22PM and anterior medial strut 22AM (collectively, struts 22M) and posterior lateral strut 22PL and anterior lateral strut 22AL (collectively, struts 22L). For clarity and simplicity part label 22 refers to any strut in general, and thus includes any particular strut (22AM, 22PM, 22AL, or 22PL).

Medial struts 22M may also be referred to as a first compressible unit, and lateral struts 22L may also be referred to a second compressible unit. This compressible terminology refers to an overall cross sectional area compressibility of prosthetic socket frame 20, wherein a first compressible unit 22M and a second compressible unit 22L can be drawn together by tensioning elements, described in detail below, to effect an adjustable control over the volume enclosed by TF prosthetic socket frame 20.

As shown in FIGS. 1A-1J, medial struts 22M, as a pair (22PM, 22AM), are connected or integral with lateral struts 22L, as a pair (22PL, 22AL) only at their distal ends, where they converge into a circumferentially complete, distal cup portion 23 of socket frame 20. Proximal to this site of distal convergence 23, medial struts 22M and lateral struts 22L have no integral connection. Struts 22M and 22L collectively define two intervening spaces (anterior and posterior) that can be referred to as a medial-lateral clefts or gaps 24. It is across these clefts 24 that socket compression may be adjusted by tensioning elements, as noted above.

Medial struts 22M include a posterior medial strut 22PM and an anterior medial strut 22AM. Medial struts 22PM and 22AM are connected in their proximal region by a medial struts bridge 26. Extending proximal to or above medial strut bridge 26, each strut 22PM and 22AM includes a peaked portion or ear 27. The most proximal point of each ear has an externally directed flare. Ear 27A, on top of anterior medial strut 22AM has a modest flare. Ear 27B on top of posterior medial strut 22PM has a more pronounced and extensive flare which is configured to engage the ischium of a patient, and generally functions as a prosthetic socket brim element that is not only configured to engage the ischium of the patient but also to bear a disproportionate amount of body weight and the force incurred by gait. Accordingly, posterior medial strut 22PM may also be referred to as an ischial strut. Both of ears 27A and 27B may serve as suspension sites for a lateral positioning sling 250, as described further below.

Embodiments of TF prosthetic socket frame 20 may be provided in a range of sizes and modified or varied configurations to accommodate the diversity of patient and residual limb sizes and configurations.

Anatomical and clinical aspects of a brim element associated with a proximal aspect of posterior medial strut 22PM as configured to engage the ischium of a patient, and the particular significance of a prosthetic socket strut that is adapted and configured to support an ischial support shelf is described in U.S. patent application Ser. No. 14/844,462 of Cespedes, et al., filed on Sep. 2, 2015, and is incorporated herein, in its entirety, by this reference.

Below, or distal to bridge 26, a medial strut window 29 is collectively defined by bridge 26, by facing longitudinal edges of medial struts 22PM and 22AM, and by a portion of the proximal edge of distal cup portion 23 of frame 20.

Lateral struts 22L include a posterior lateral strut 22PL and an anterior lateral strut 22AL. Lateral struts 22PL and 22AL are connected by a lateral struts bridge 31. Extending proximal to or above medial strut bridge 31, each strut 22PL and 22AL includes curved trochanteric extensions 32. Below, or distal to bridge 31, a lateral strut window 34 is collectively defined by bridge 31, by facing longitudinal edges of lateral struts 22PL and 22AL, and by a portion of the proximal edge of distal cup portion 23 of frame 20.

Details of embodiments of TF prosthetic socket frames are shown in FIGS. 1A-14B, and are discussed further below.

Embodiments of a transfemoral (TF) prosthetic socket frame 20, struts 20, in particular, as described herein, may be fabricated from any suitable material; typical materials include plastics, such as thermoset plastics and thermoplastics, which may further include fiber, such as carbon or glass fiber, by way of example.

In one approach, a TF prosthetic socket frame 20 may be fabricated by way of a thermoset plastic layup that results in a single-piece integral frame. However embodiments of the invention also include TF prosthetic frames formed from thermoplastic fiber composite materials, as assembled from modular components, and which may include adjustable connection features that allow assembly of prosthetic socket frames of varying configuration depending on the modular components selected from an inventory of components. The varying configurations can arise from several factors associated with modularity. In one instance, varying size and shape can arise from the selection of modular components that vary in size and/or shape. In another instance, varying size and shape can result from exercising adjustable options in the ways in which modular components can be assembled together.

In particular regard to embodiments of a TF prosthetic socket frame formed from thermoplastic fiber composite material, typically, the fiber component of the thermoplastic fiber composite is in a long or continuous form. In particular modular component embodiments, such as struts, the material may consist entirely of a thermoplastic-fiber composite. And in particular embodiments, the fiber of the thermoplastic fiber composite consists entirely of continuous fiber. By virtue of the use of thermoplastic (i.e., as in the thermoplastic fiber composite material), components fabricated therefrom can be thermally reformed. This aspect provides yet another approach to creating TF prosthetic socket frames that vary in shape.

The use of thermoplastic fiber composite material in the fabrication of prosthetic socket struts has been described in detail in co-owned U.S. patent application Ser. No. 14/213,788 (US 2014/0277584) of Hurley et al., as filed on Mar. 14, 2014, and which is incorporated herein, in its entirety. All description in the referenced application related to the thermoplastic fiber composite composition of struts is applicable to these presently described alternative embodiments of a TF prosthetic socket frame.

A further thermoplastic material suitable for use in fabricating struts for use in a TF prosthetic socket 20 is described in US Patent Publication No. US 2014/0256850 of Gerard et al, in which a thermoplastic fiber composite material that is formed from an in situ polymerization of methacrylic resins within a matrix of long fibers.

A distal base assembly 35 is disposed distal to distal cup portion 23 portion of TF prosthetic socket 20, and connected thereto. Aspects of distal base assembly 35 and its components (distal base plate 35A, rotational clamp 35B, and slidable offset adapter 35C) are shown in FIGS. 18A-18C, and described in further detail below.

"Suspension", as applied to prosthetic socket frame and slings embodiments provided herein, may be used in two senses. In one sense, "suspension" refers to the suspension of lateral sling 250 and medial sling 210 within prosthetic from 20 by way of suspension pockets disposed in the proximal portion of sling embodiments. In another sense, suspension refers to the suspension of prosthetic socket 20 on the host residual limb 1. In this latter sense, distal base assembly 35 may be configured in any of several ways to maintain or suspend prosthetic socket 20, as a whole, on the residual limb, including any of vacuum suspension, pin-lock suspension, or a lanyard based suspension mechanism.

In addition to prosthetic frame elements, such as struts, as described above, a prosthetic socket 20 may include a set of one or more positioning slings that are disposed and operate substantially within the frame (an intra frame positioning device), albeit anchored to features of the frame. In one embodiment of the invention, a prosthetic socket includes a set of positioning slings, a first sling and a second sling. In an example of this embodiment, a first sling is positioning medial sling 210, and a second sling is lateral positioning sling 250, as described in detail below. Embodiments of positioning slings may be provided in a range of sizes and modified configurations to accommodate the diversity of patient and residual limb sizes and configurations. TF positional slings 210 and 250 are shown as arranged frame embodiments and in isolation variously in FIGS. 4A-14B, and described in further detail in Section C ("Illustrated Embodiments) below. Flat patterns of TF positional slings 210 and 250 are shown in FIGS. 15A-17B, and also described in further detail below.

Accordingly, in addition to various structural elements, a prosthetic frame 20, as described above, prosthetic socket may include a set of positioning slings (medial sling 210 and lateral sling 250) that are rigged within and onto features of socket frame 20. Embodiments of a set or system of textile or fabric-based positioning slings support and position a residual limb of a patient within a TF prosthetic socket 20. Slings are configured to apply force (1) circumferentially around and (2) orthogonally against the longitudinal axis of a residual limb hosted therein. Thus, in one aspect, sling-driven force is centrally directed and compressive on the limb, but more significantly, each sling is also arranged and configured within a socket to deliver a net horizontal force vector (from the patient's perspective) within the anatomical coronal plane.

By way of brief introduction of fabric-based slings, as described in detail below, an embodiment of a set of slings includes a medial sling 210 and a lateral sling 250. Both slings are rigged at distal and proximal sites of attachment or suspension that maintain them, longitudinally, in a substantially vertical alignment within a prosthetic socket frame 20. Medial sling 210 is so named because the major portion of the residual limb contacting and force application portion of the fabric is on the medial side of the residual limb (and medial side of prosthetic socket 20); lateral sling 250 is so named because the major portion of the residual limb contacting and force application portion of the fabric is on the lateral side of the residual limb (and lateral side of prosthetic socket 20). When tensioned, medial sling 210, along with a residual limb hosted therein, is drawn away from the medial side of prosthetic socket 20 and toward its lateral side. When tensioned, lateral sling 250, along with a residual limb hosted therein, is drawn away from the lateral side of prosthetic socket 20 and toward its medial side. Thus, as described in detail below, slings 210 and 250 cooperate to position the residual limb within the prosthetic socket frame.

To summarize now some of the directional or vectored aspects of intra-socket position and force application:

Medial sling 210 is arranged so as to pull on the medial longitudinal side of a residual limb, pulling it laterally—it is anchored around a lateral structural feature of the hosting prosthetic socket, but in some embodiments, it may be free floating within the medial side of the host socket. Medial sling 210 may be understood as being "medial" in the sense that it is slung around the medial side of a residual limb hosted therein, which is generally disposed in a medial longitudinal sector of a hosting prosthetic socket frame.

Lateral sling 250 is arranged so as to pull on the lateral longitudinal side of a residual limb, pulling it medially—it is anchored around a medial structural feature of the hosting prosthetic socket, but in some embodiments, it may free floating within the lateral side of the host socket. Lateral sling 250 may be understood as being "lateral" in the sense that it is slung around the lateral side of a residual limb hosted therein, which is generally disposed in a lateral longitudinal sector of a hosting prosthetic socket frame.

Turning now to some biomechanical considerations regarding the relationships among a prosthetic socket, a residual limb hosted therein, and the residual bone within the residual limb. Distinguishing the residual bone from the residual limb as a whole calls attention to the fact that the bone represents a hard structural continuity through the limb that can act (or be acted upon) as a lever, something that soft tissue (primarily muscle) of limb cannot function as. The prosthetic socket has an attachment to the body and a general structural configuration that provides a default vertical orientation of the residual limb with respect to the upper body. That orientation applies broadly to the residual limb as a whole, but it applies less specifically to the residual bone within the residual limb. This gap between the orientation and the constraints of a prosthetic socket as imposed on the limb (in general) and to the residual bone (in particular) comes about, at least in part, because the bone has a freedom of movement within the general profile of the residual limb's muscle and other soft tissue. Further contributing to a freedom of movement of the residual bone within the residual limb is the condition that the residual limb is missing the normal constraints and functionality provided by intact distal attachments of muscle to bone structure.

Given the biomechanical context of a residual limb disconnected from the ground, a default or bias of the limb is for its distal end tends to abduct (to move outward, laterally) in the absence of applied stabilizing force(s), such as contact with the ground, or the full normal complement of limb musculature and sites of skeletal attachment. From the perspective of biomechanical factors located around the distal end of the limb (where there would normally be a knee), this abductive movement may be understood as a consequence of a varus moment. The prosthetic socket (particularly in conjunction with a distal prosthetic component that is stabilized by contact with the ground) does serve to constrain that abductive movement. But, as noted above, the residual bone within the limb is less constrained than the residual limb as a whole.

Embodiments of the present invention, accordingly, are directed toward constraining the residual limb in such a way that focuses particularly on leveraging the skeletal portion of the residual limb. More particularly, as described in detail below, embodiments of the invention are directed toward stabilizing the residual limb internally, within the prosthetic socket frame, by way of appropriately balancing opposing forces that act on the bone in its capacity as the longitudinal skeletal structure component of residual limb. In some embodiments of the invention, such opposing forces include lateral-ward and medial-ward horizontal forces within the anatomical coronal plane.

From the patient's perspective, the roles of the prosthetic socket frame can be understood to functionalize the residual limb by supporting it, orienting it, constraining it, and ultimately, allowing the patient to transfer his or her intent through the residual limb and into more distal prosthetic elements. Embodiments of positioning slings, as provided herein, take these attributes provided by the prosthetic socket frame as a baseline, and enhance each one of them. By operating from within the frame, slings bring about enhanced support of the residual limb, a more highly resolved and biomechanically appropriate orientation of the residual limb (the bone, in particular) with respect to the patient's upper body, and a more effective translation of the patient's intent into function.

Embodiments of positioning slings 210 and 250, as provided herein, are soft (fabric) structures that create a residual limb environment that plays out within the structural frame of a transfemoral (TF) prosthetic socket 20. Embodiments of slings, as provided herein, can deliver opposing forces within the anatomical coronal plane as determined by the configuration of their rigging within a socket. In the exemplary embodiments provided herein, such as slings 210 and 250, the structure and placement of slings defines their broad regions of influence, per proximal, distal, medial, and lateral coordinates. In another aspect, variable attributes of slings also may be configured to play out differentially within particular regions of their surface. For example, the fabric of slings may include distinct zones, as determined by selective construction and material selection, to be regions of stretch, non-stretch, biased stretch, and structural or strength reinforcement. When appropriately positioned within sling fabric, these regions can control force transfer for biomechanical control of the residual limb, pressure distribution for safety and comfort, shock absorption for safety and comfort, and strength for durability.

As an example of the invention and its various attributes and features, one particular embodiment of the invention will be described in some detail. Prosthetic socket slings may be incorporated into a wide variety of slings. For the purposes of depicting a set of slings, a particular socket embodiment, TF prosthetic socket 20, is used as a model prosthetic socket host for slings 210 and 250.

FIGS. 6A-14B show an embodiment of a TF prosthetic socket 20 with a set of two slings, medial sling 210 and lateral sling 250, that make use of structural features as vertically aligned anchors, such as longitudinal struts 22, but which exert forces on a residual limb being hosted by the socket from within the space circumscribed the four struts 22. More specifically, and with reference to compressive force and to laterally or medially directed forces, as applied to the residual limb by way to either medial sling 210 or lateral sling 250: the compressive force being applied by the slings is not driven by compression of struts 22. Compression exerted by either sling is driven by circumferential (centripetally directed) tensioning around the slings, independently of any compressive force that may be being applied by the struts 22. Struts 22 may, indeed, be exerting some level of compressive force on the residual limb; but the point being emphasized now is that any compressive force exerted by a positional sling is separate, independent, and in addition to any such strut driven compressive force. In contrast, laterally or medially directed forces, as applied by sling 210 or sling 250, do rely on particular struts 22 as vertical anchors.

Struts 22 of TF prosthetic socket frame 20 may be grouped in sets of medial struts and lateral struts, corresponding with anatomical references to residual limb 1. Medial struts include posterior medial strut 22PM and anterior medial strut 22AM. Lateral struts include posterior lateral strut 22PL and anterior medial strut 22AL.

Medial sling 210 is configured to include several functional sections: a medial sling residual limb wrapping or hosting portion 212, at least one medial sling proximal socket support attachment portions (typically but not necessarily configured as an inverted pocket) 214, and one or more medial sling wrapping extension tabs 222 with straps 224 and buckling attachments 226.

Medial sling 210 is configured and disposed within TF prosthetic socket frame 20 such that residual limb wrapping portion is vertically aligned along and centered around the medial side of a hosted residual limb 1 and internal to medial struts 22PM and 22AM. Wrapping extension tabs 222 are extended outward from either side of a generally proximal aspect of limb wrapping portion 212, and support straps 224, each strap 224 having have attachment components 226 (such as a buckle, or a Boa device, or any functional equivalent) secured to the end of each extension tab 224. When TF prosthetic socket 20 is hosting residual limb 1, wrapping extension tabs 222 extend around residual limb 1 and respective buckle components 226 meet along a lateral side of residual limb 1 (or along a lateral side of prosthetic socket 20). Wrapping extension tabs 222, the ends of straps 224 and strap-associated buckles 226 are arranged such that they extend externally around lateral struts 22PL and 22AL.

When TF prosthetic socket 20 is being worn by patient 1, the effects of buckling of buckle components 226 and tensioning by way of tensionable straps 224 include a compression around residual limb 1 and a net horizontally aligned pull in an anatomically lateral direction, away from the medial side (as defined by medial struts 22PM and 22AM) of TF prosthetic socket 20, and toward the lateral side of prosthetic socket (as defined by lateral struts 22PL and 22AL).

Lateral Sling 250 is configured to include functional sections: a lateral sling residual limb wrapping or hosting portion 252, at least one lateral sling proximal socket support attachment portion (typically but not necessarily configured as an inverted pocket) 265, a distal socket support attachment portion 260, and one or more wrapping extension tabs 256 with straps 257 and associated buckling attachments 258.

Lateral sling 250 is configured and disposed within TF prosthetic socket 20 such that residual limb wrapping portion 252 is vertically aligned along and centered around the medial side of a hosted residual limb 1 and internal to lateral struts 22PL and 22AL. As positioned at a generally distal position on wrapping portion 252, wrapping extension tabs 256 extend outward from each side of limb wrapping portion 252, and support straps 257, each strap 257 having have buckle components 258 secured its respective the end, and effectively, at the end of each extension tab 257. A strap 260 is positioned at a generally distal position on wrapping portion 252; it hosts a strap 261 that includes a buckle 262 at each end.

When TF prosthetic socket 20 is hosting residual limb 1, generally distal wrapping extension tabs 256 of lateral sling 250 extend around residual limb 1, and respective buckle components 258 meet along a medial side of residual limb 1 (or along a medial side of prosthetic socket 20). Wrapping extension tabs 256, the ends of straps 257, and strap-associated buckles 258 are arranged such that they extend externally around medial struts 22PM and 22AM. Similarly, when prosthetic socket 20 is hosting residual limb 1, generally proximal strap-associated buckles 262 at ends of straps 261 also meet along the medial side of residual limb 1 (or along a medial side of prosthetic socket 20).

When TF prosthetic socket 20 is being worn by patient 1, the effects of (a) buckling of buckle components 258 and tensioning by way of tensionable straps 257 and (b) buckling or buckle components 262 and tensioning by way of straps 261, collectively include a compression around residual limb 1 and a net horizontally aligned pull in an anatomically medial direction, away from the lateral side (as defined by medial struts 22PL and 22AL) of prosthetic socket 20, and toward the medial side of prosthetic socket 1 (as defined by medial struts 22PM and 22AM).

As shown in FIG. 1, straps 256 and strap 261 of lateral sling 250 occupy relatively distal and proximal positions within socket 1, or with respect to residual limb 1 as it's hosted in TF prosthetic socket 1. Straps 224 of medial sling 210 occupy a central vertical position, between the distal and proximal positions of straps 256 and 261, respectively. The tensioning of these various straps creates a class 1 lever system that provides a leverage controlling mechanism applicable to the residual limb, particularly controlling the femur, as it is the femur that ultimately provides resistance to horizontally impinging forces.

The horizontal, lateral-ward vectors created by tensioning of straps 224 of extension tabs 222 of medial sling 210 acts as a fulcrum of the class 1 lever. The combined effects of tensioning proximal straps 261 and distal straps 257 of lateral sling 250 act as two medial-ward vector forces on either side of the fulcrum provided by tensioning straps 224.

To summarize now some of the directional aspects of intra-socket position and force application: Medial sling 210 is arranged so as to pull on the medial longitudinal side of a residual limb, pulling it laterally—it is anchored around a lateral structural feature of the hosting prosthetic socket, but is free floating within the medial side of the host socket. And lateral sling 250 is arranged so as to pull on the lateral longitudinal side of a residual limb, pulling it medially—it is anchored around a medial structural feature of the hosting prosthetic socket, but is free floating within the lateral side of the host socket.

The forms of thermoset plastic-based embodiments of the transfemoral (TF) prosthetic socket frames are fabricated by way of plastic lamination procedure; the final form of these prosthetic sockets are determined by trim lines that define what portion of a lamination layup is included in the final form, and what portion is waste to be removed. Prosthetic frames are fabricated by way of a thermoset plastic lamination procedure.

Illustrated Embodiments

The description now turns to aspects and features of embodiments of the invention as depicted in each of the accompanying FIGS. 1A-18C, described in order.

FIGS. 1A-1H show various views of an embodiment of a transfemoral (TF) prosthetic socket frame 20, as provided herein. As depicted in figures herein, a left residual limb (i.e., a left thigh) is used as the example throughout, and thus, accordingly, a left TF prosthetic socket 20 is also depicted through out the figures. FIGS. 1A-1D show side views of an embodiment of a transfemoral prosthetic socket frame 20, including a medial view (FIG. 1A), a posterior view (FIG. 1B), an anterior view (FIG. 1C), and a lateral view (FIG. 1D). FIG. 1E shows a top view of an embodiment of a transfemoral (TF) prosthetic socket frame 20, consistent with FIGS. 1A-1D. FIG. 1B also shows slots 25 for a tensioning strap (not shown) that, in some embodiments, connects adjacent struts and allows a tensioning that creates a medially directed force vector on the proximal aspect of lateral struts, as described further below, in context of FIG. 7B.

FIGS. 1B, 1C, 1F, and 1G all provide views of cleft 24 as defined by adjacent medial and lateral struts. More particularly, struts 22PM and 22AM define a cleft 24, and struts 22PL and 22PM define a cleft 24. These clefts 24 may be appreciated by contrasting to the structural relationship between adjacent medial struts 22PM and 22AM, which are connected by a proximal bridge 27, and by the structural relationship between adjacent lateral struts 22AL and 22PL, which are connected by a proximal bridge 31. By virtue of structural bridges 27 and 31, the bridged struts, respectively, are substantially incompressible toward each other. A functional significance of clefts 24 is that the neighboring struts that define the clefts provide a site for compression of the cross sectional area of the socket cavity. These sites of compression are described elsewhere, and indeed are sites of compression as facilitated by adjustable connecting or tensioning straps 25S, operating through proximal slots 25 in adjacent struts.

Figure 1I:
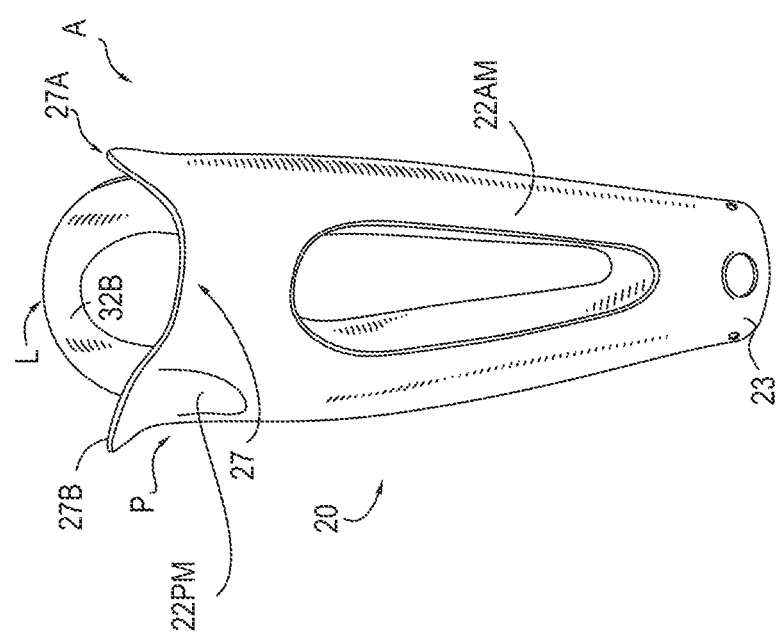

In the prosthetic socket frame 20 embodiment shown in FIGS. 1A-1H (as well as other figures herein) proximal trochanteric extensions 32 of lateral struts 22AL and 22PL are shown as crescent shaped elements converging toward each other. In an alternative embodiment, such proximal trochanteric extensions are conjoined, and may accordingly be referred to as a trochanteric bridge. Accordingly, FIGS. 1I-1H show medial and lateral views, respectively, of an alternative embodiment of a transfemoral (TF) prosthetic socket frame, one in which trochanteric extensions of lateral struts are proximally conjoined as trochanteric bridge 32B.

FIG. 1K is a schematic top view of an embodiment of a TF prosthetic socket frame that clarifies strut positioning with respect to anterior-posterior and lateral-medial reference terminology, and is intended to depict dynamics of circumferential compression of the central prosthetic socket cavity. A reference XY axis is shown centrally disposed among struts 22AM, 22PM, 22AL, and 22PL. Each of these four struts is disposed within a 90° sector, as shown. Struts 22AM and 22PM may be regarded as a pair of medial struts 22M. Struts 22AL and 22PL may be regarded as a pair of lateral struts 22L. Each of strut pairs 22M and 22L, respectively, are held apart by a structural bridge that prevents them from being compressible toward each other. However, strut pairs 22M and 22L, as pairs, are compressible in that they can be drawn closer together by an intra-frame constraining or tensioning mechanism (not shown) that can compress the space defined by the four struts in a medial-lateral manner (see FIG. 12).

FIGS. 2A-2F provide various anterior cross sectional and transparent views of prosthetic socket 20 with a particular focus on horizontal force vectors that are applied to a hosted residual limb by positional slings, medial sling 210 and lateral sling 250.

Figure 2C:
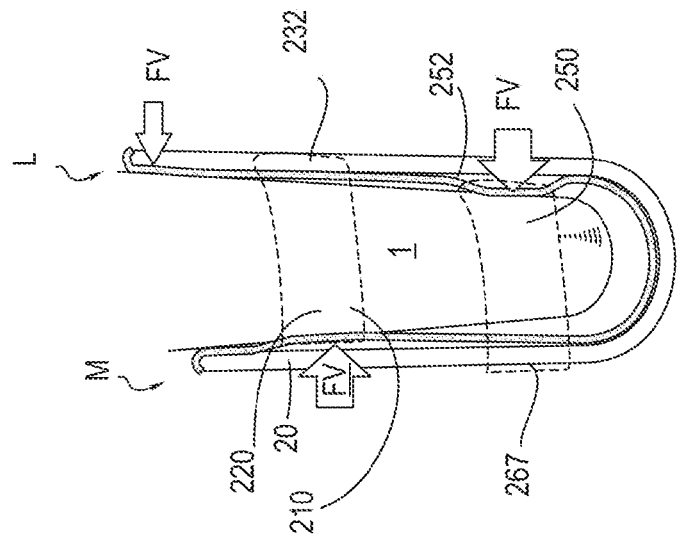
FIG. 2C is a schematic view of a residual limb being subjected to horizontal force vectors, as applied by an embodiment of a TF prosthetic socket frame, rigged with lateral and medial slings, showing only the tensioning features associated with lateral and medial slings that produce the horizontal vectors.
Figure 2B:
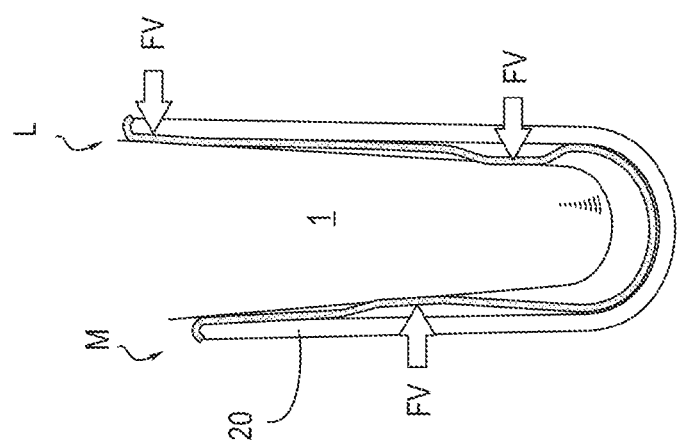
FIG. 2B is a schematic view of a residual limb being subjected to horizontal force vectors, as can be applied by an embodiment (not shown) of a TF prosthetic socket frame rigged with lateral and medial slings.
Figure 2A:
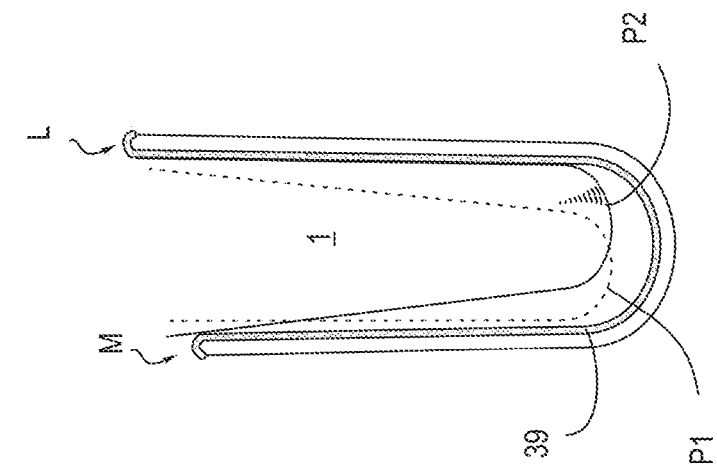
FIG. 2A is a cross sectional view of a residual limb, in a liner, disposed within a prior art TF prosthetic socket, not having the advantage of positional slings.

FIGS. 2A-2C compare the disposition of a residual limb within a prior art transfemoral (TF) prosthetic socket (FIG. 2A) vs. the disposition of a residual limb 1 within an embodiment of a transfemoral (TF) prosthetic socket frame 20 (FIGS. 2B-2C). In FIGS. 2A-2C, prior art prosthetic socket frame and TF prosthetic socket frame 20 are both represented schematically; the focus is on horizontal forces that impinge on a residual limb 1 as a patient stands or ambulates, and counteracting force vectors FV that can be applied to the residual limb 1 to stabilize it within a TF prosthetic socket 20. FIG. 2A shows cross sectional view of a residual limb 1 (within in a prosthetic socket liner) disposed within a prior art TF prosthetic socket, not having the benefit of positional slings. Without positional slings, residual limb 1 has a tendency to move within the socket from a first position P1 to a second position P2 as a consequence of forces that impinge on residual limb.

FIG. 2B shows a schematic view of a residual limb 1 being subjected to horizontal force vectors (indicated by arrows FV), as can be applied by an embodiment of a TF prosthetic socket, as seen in detail in figures that follow. The scope of the invention includes any arrangement or set of features than can create and control such a set of vectors within a prosthetic socket frame. For example, such forces could be implemented by controlled inflation and deflation of air or liquid bladders. In embodiments of the invention that are described and depicted herein, such forces are driven by various embodiments of intra-frame positional slings. The arrangement of the three force vectors arrows FV can be seen to form a 3-point lever stabilizing system that can be very effective at controlling medial-lateral movement of a residual limb enclosed by such a system.

FIG. 2C shows a schematic view of a residual limb 1 being subjected to horizontal force vectors FV (and as indicated by arrows), as applied by embodiments of a lateral sling 250 and a medial sling 210 that are rigged within an embodiment of a TF prosthetic socket frame 20 (only the tensioning features associated with lateral and medial slings that produce the horizontal vectors FV are shown). In this basically cross-sectional view, lateral sling 250 is represented by dotted lines that outline an arm of the sling. Medial sling 210 is similarly represented by dotted lines that outline a tensioning arm of the sling.

For orientation and to reiterate a convention of terminology used herein, a medial positioning sling is one that exerts pressure on the medial size of a residual limb. This means that it is anchored on the lateral side of a prosthetic socket, and pulls the residual limb in a lateral direction. A lateral positioning sling is one that exerts pressure on the lateral size of a residual limb. This means that it is anchored on the medial side of a prosthetic socket, and pulls the residual limb in a medial direction.

Lateral sling 250 is anchored at a site 267 on a medial side of TF prosthetic socket frame 20. Medial sling 210 is anchored at a site 232 on a lateral side of TF prosthetic socket frame 20. By tensioning actions of these slings, a horizontal vector FV is activated on a medial side of prosthetic socket frame 20, and a horizontal FV on a distal aspect of prosthetic socket frame 20 is activated.

Several tensioning mechanisms are involved in activating a medially directed force vector FV on a proximal aspect of prosthetic socket frame 20. By the combination of these three force vectors FV, it can be seen in FIG. 2C that a 3-point lever stabilizing system is enabled that can counteract the cumulative effect of forces visited upon residual limb 1 that can create effects such as those seen in the prior art prosthetic socket (FIG. 2A).

In yet another aspect, the proximal (medially-directed) force vector FV on the lateral side of TF prosthetic socket 20 is mediated independently of positional slings by two contributory mechanisms. For example, an intra-strut tensioning strap, as shown in FIG. 1B and FIG. 7B is a driver of such force. The proximal, medially directed force vector FV is shown in FIGS. 2B, 2C, 2E, and 2F involves tensioning action provided by an intra-strut tensionable strap 25S that engages proximally disposed slots 25 in adjacent anterior and posterior struts (e.g., see anterior struts 22AM and 22AL in FIG. 1B. An analogous slot and strap arrangement is disposed in adjacent posterior struts 22PM and 22PL (not shown).

Figure 2F:
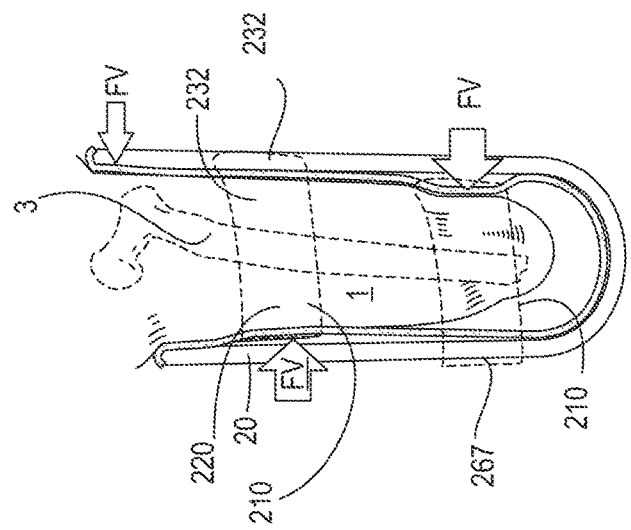
FIG. 2F is a schematic view of a residual limb being subjected to horizontal force vectors, as applied by an embodiment of a TF prosthetic socket frame, rigged with lateral and medial slings, showing only the tensioning features associated with lateral and medial slings that produce the horizontal vectors.
Figure 2E:
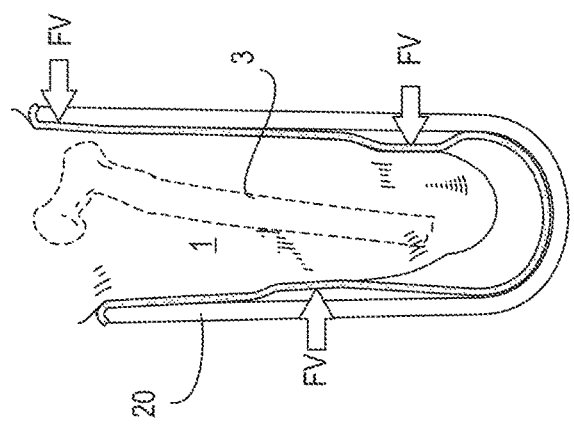
FIG. 2E is a schematic view of a residual limb being subjected to horizontal force vectors, as can be applied by an embodiment (not shown) of a TF prosthetic socket frame rigged with lateral and medial slings.
Figure 2D:
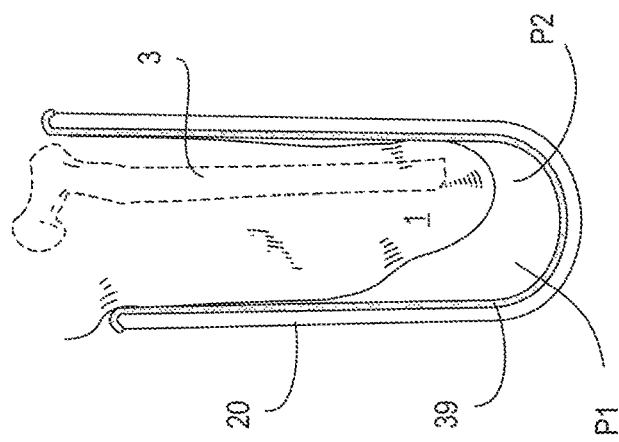
FIG. 2D is a cross sectional view of a residual limb, in a liner, disposed within a prior art TF prosthetic socket, not having the advantage of positional slings.

The views provided by FIGS. 2D-2F are generally the same as those of FIGS. 2A-2C except that the residual limb is rendered transparently to particularly focus on the positional effects on the femur within the residual limb. These views emphasize that the residual femur 3 is actually the main target of force vectors FV applied to the residual limb 1 (i.e., the primary target is not the residual limb as a whole). This follows from the fact that the main mass of the residual limb (muscle, fat, connective tissue) is compliant and can absorb pressure by way of changing shape. In contrast, bone is non-complaint, and absorbs pressure or force by movement or shifting position, not by changing shape. This contrast in response to force vectors FV is shown schematically FIGS. 2D-2F, where, in response to the combined and balanced forces provided by the three illustrated force vectors FV, the residual femur shifts from a default generally abducted position (the distal end of the residual femur is directed laterally) to a biomechanically appropriate adductive position (the distal end of the residual femur is directed more medially).

Figure 3B:
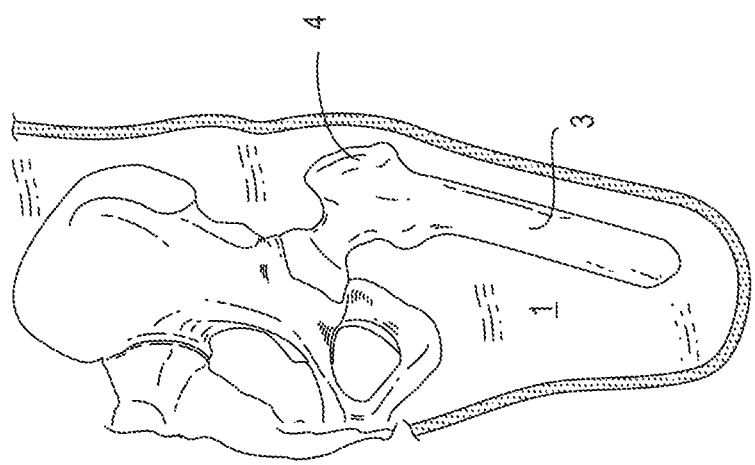
FIG. 3B shows the transparent anterior face view of a residual thigh as in FIG. 3A, the residual thigh being disposed in an embodiment of a TF prosthetic socket frame shown in cross-section, according to one embodiment.
Figure 3A:
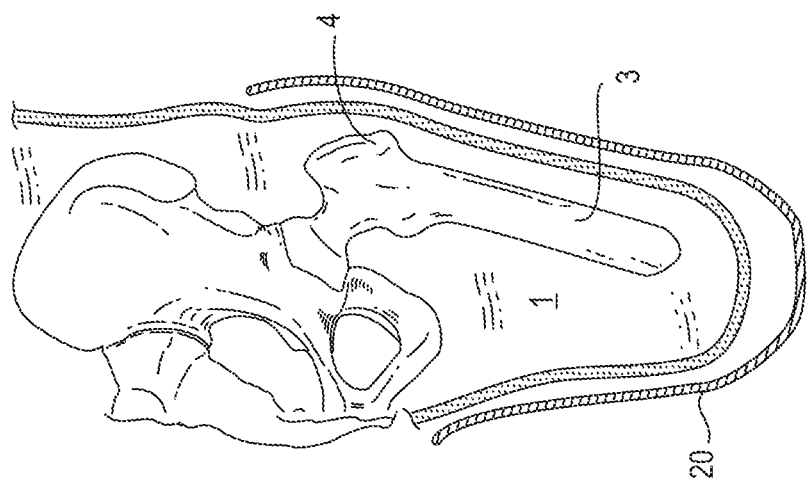
FIG. 3A shows a transparent anterior face view of a residual thigh, focusing particularly on the residual femur and its greater trochanter, the femur having an amputation site at its distal end.

FIGS. 3A-3B show, respectively, (FIG. 3A) a transparent view of a residual limb 1, showing, in particular, the residual femur 3 and greater trochanter 4 of residual thigh 1 that has an amputated distal end, and (FIG. 3B) a coronal plane cross sectional view of a prosthetic socket frame 20 hosting the residual limb 1. These views of the residual thigh 1 are the schematic basis for figures that depict a residual limb hosted in a TF prosthetic socket frame 20 that is rigged variously with medial (210) and lateral (250) slings, such as FIGS. 4A-7B and FIGS. 11A-12C.

FIGS. 4A-5D show various views of a transfemoral (TF) prosthetic socket frame 20, with particular attention to the effect that tensioning mechanisms of both medial 210 and lateral 250 positional slings have on the disposition of a residual thigh 1 (also showing greater trochanter 4) hosted therein. By way of orientation with regard to terminology used herein, a medial positioning sling 210 is one that exerts horizontal force on the medial side of a residual limb; a lateral positioning sling 250 is one that exerts horizontal force on the lateral side of a residual limb.

FIGS. 4A-4D all relate to the intra-frame forces exerted on the residual limb by medial positioning sling 210. In typical embodiments of the invention, both medial positioning sling 210 and lateral positioning 250 sling are at work, but FIGS. 4A-4D and present description focus on medial positional sling by itself. FIGS. 4A and 4C show views of a residual thigh as in FIG. 3B, further showing a tensioning arm portion of medial sling 210 which is part of a more complete circumferential tensioning mechanism 220. FIG. 4B and FIG. 4D show top views, respectively of FIG. 4A and FIG. 4C (absent the residual limb).

A tensioning mechanism 220 refers to the totality of any aspect of a structural element or series of elements that establishes a structural continuity through a medial sling 210 that, when tensioned, creates an inwardly directed pressure and a net horizontal force in a lateral direction on the sling within prosthetic socket frame 20. Medial sling 220 is anchored on an anchoring site 232 around an external aspect of lateral struts 22L. For reference the proximal portion 32 of lateral strut of prosthetic socket 20 is labeled.

The difference between the view of FIGS. 4A and 4C is that prosthetic socket 20 in FIG. 4A is un-tensioned by positional sling 210, whereas in FIG. 4C medial positional sling 210 is tensioned. The tension manifests as a laterally directed force vector FV, and it further manifested an increase in the distance between the residual limb and the medial side of the socket; note that D1 in FIG. 4A is small, whereas D1' has increased in FIG. 4C. FIGS. 4B and 4D show these same relationships in top view.

FIGS. 5A-5D all relate to the intra-frame forces exerted on the residual limb 1 by lateral positioning sling 250, as seen in side views (FIGS. 5A and 5C) and top views (FIGS. 5B and 5C). In typical embodiments of the invention, both medial positioning sling 210 and lateral positioning 250 sling are at work, but FIGS. 5A-5D and present description focus on lateral positioning sling 250 by itself. FIGS. 5A and 5C show views of a residual thigh as in FIG. 3B, further showing a tensioning arm portion of lateral sling 250 which is part of a more complete circumferential tensioning mechanism 220. FIG. 5B and FIG. 5D show top views, respectively of FIG. 5A and FIG. 5C (absent the residual limb).

FIG. 5A shows a view of a residual thigh 1, further showing a tensioning arm portion 255 lateral sling 250 that, when tensioned, crates an inwardly directed pressure and net horizontal force in a medial direction on the sling within prosthetic socket frame 20. Lateral sling 250 is anchored on a medial anchoring site 267 of the hosting TF prosthetic socket frame 20, more particularly around an external aspect of medial struts 22M.

The difference between the view of FIGS. 5A and 5C is that prosthetic socket 20 in FIG. 5A is un-tensioned by lateral positioning sling 250, whereas in FIG. 5C lateral positional sling 250 is tensioned. The tension manifests as a medially directed force vector FV, and it further manifested an increase in the distance between the residual limb and the lateral side of the socket; note that D3 in FIG. 5A is small, whereas D3' has increased in FIG. 5C. FIGS. 5B and 5D show these same relationships in top view.

Figure 6B:
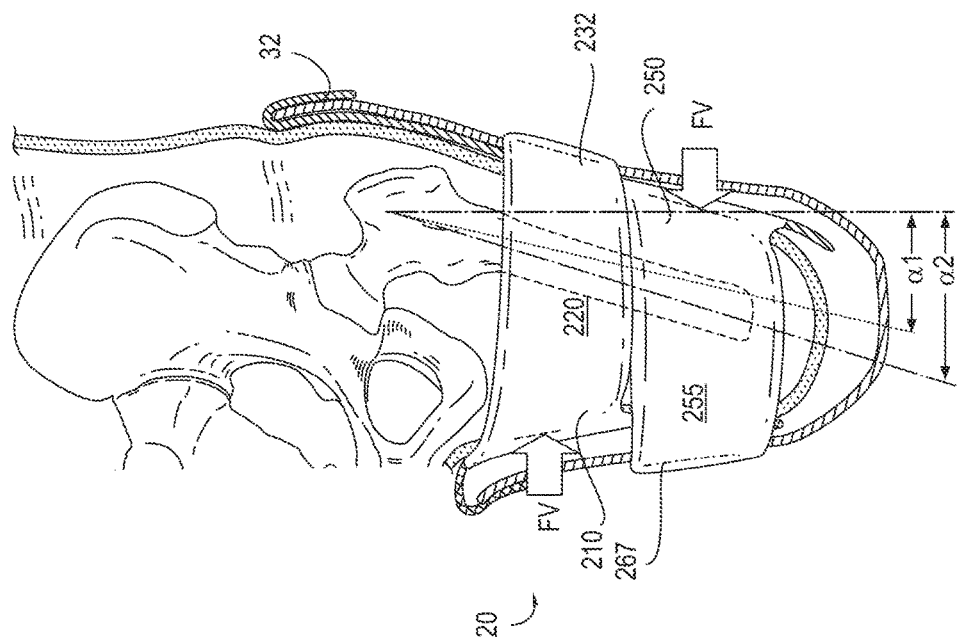
FIG. 6B is a cross-sectional view of a residual thigh hosted in a TF prosthetic socket embodiment as in FIG. 6A, the tensioning mechanisms of both the medial and lateral slings now in a tensioned state.
Figure 6A:
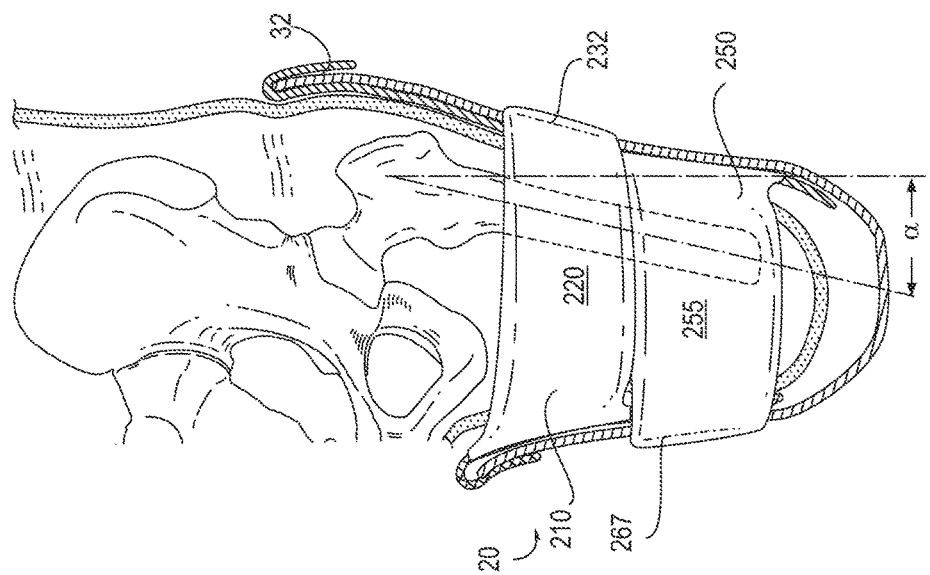
FIG. 6A is a cross-sectional view of a residual thigh hosted in a TF prosthetic socket embodiment as in FIG. 3B, further showing a tensioning system element of both a medial sling anchored on a lateral anchoring site of the hosting TF prosthetic socket frame and a lateral sling anchored on a medial anchoring site of the hosting TF prosthetic socket frame, both tensioning mechanisms in an un-tensioned state.

FIGS. 6A-6B show views of an embodiment of a transfemoral (TF) prosthetic socket 20 with tensioning systems for both medial sling and lateral positioning slings, focusing particularly on their respective anchoring points on the prosthetic socket frame, and providing a transparent view of the anatomy within the socket. FIG. 6A shows a view of a residual thigh 1 hosted in a TF prosthetic socket embodiment 20 (as in FIG. 3B) further showing a tensioning system element of both a medial sling 210 anchored on a lateral anchoring site 232 of the hosting TF prosthetic socket frame 20 and a lateral sling 250 anchored on a medial anchoring site 267 of the hosting TF prosthetic socket frame 20, both tensioning mechanisms being in an un-tensioned state. In general, sling-anchoring sites 232 and 267 entail an excursion at least a portion of the otherwise internal sling (within the socket frame) around an external aspect of a frame feature such as a strut. In alternative embodiments, the anchoring sites may not need the external excursion, but are associated with an internal site associated with a frame. FIG. 6B shows a residual thigh 1 hosted in a TF prosthetic socket embodiment as in FIG. 6A, the tensioning mechanisms of both the medial and lateral slings now in a tensioned state.

Force vector arrows FV emphasize the horizontal directionality of forces exerted by medial positioning sling 210 and lateral positioning sling 250, respectively. As shown, force vector arrow FV on the lateral side of lateral sling 250 and the force vector arrow FV on the medial side of medial sling 210 (FIGS. 14A-14B) are opposing forces that cooperate in stabilizing and biomechanically optimizing the disposition of the residual limb within prosthetic socket frame 20. Further noting the change in angle from a vertical line of the residual limb between the position shown in FIG. 6A, where the residual limb is disposed at an angle α1 from the vertical, and the greater, more adductive angle α2 from the vertical, as seen in FIG. 6B.

FIGS. 7A-7D show external anterior side views of an embodiment of a transfemoral (TF) prosthetic socket 20, focusing in particular on the externally visible portions of the tensioning systems of both the medial and lateral slings. The externality of the view also shows the struts in manner similar to the views provided by FIGS. 1A-1J. Positioning slings 210 and 250 are stippled to create a gray color, and stand out against the white structural surfaces of prosthetic socket 20, a motif used in various figures that follow.

FIGS. 7A-7B show tension arm portions of each sling (tensioning arm 220 of medial sling 210 and tensioning arm 255 of lateral sling 250) and introduce a tensioning strap 25S, which is further shown in FIGS. 7C-7D. FIG. 7A depicts only the externally visible aspects of prosthetic socket 20 (including medial sling 210, and lateral sling 250 as seen variously before, in FIGS. 4A-6B. Only small portions of the main bodies of slings 210 and 250 are visible because the main bodies are internal to the struts. Tensioning mechanism or member 220 of medial sling 210 can be seen to be secured at anchoring site 232, which involves tensioning member 220 wrapping around an external aspect of anterior lateral strut 22AL. Tensioning mechanism or member 255 of lateral sling 250 can be seen to be secured at anchoring site 267, which involves tensioning member 255 wrapping around an external aspect of anterior medial strut 22AM.

FIG. 7B shows an embodiment of a TF prosthetic socket similar to that of FIG. 7A that further includes a tensioning strap 25S which connects adjacent lateral and medial struts: strap 25S is inserted through slots 25 in the proximal portion of adjacent lateral and medial struts. Another strap 25S (not shown) may be disposed on the posterior aspect of socket 20. Straps 25S, as threaded through slots 25, are adjustable and contribute to constraining or limiting the extent to which lateral struts 22AL-22PL and medial struts 22AM-22PM separate from each other. Although these straps are adjustable and are capable of providing tension, in typical usage, this level of constraint or adjustment is a high level, relatively low resolutions adjustment that commonly remains fixed in daily usage, i.e., likely not to be changed during the day, but remaining fixed according to the personal preference of the user.

Straps 25S, while connecting neighboring anterior and posterior struts, actually exert a centripetal force from a fully circumferential disposition in that neighboring lateral struts 22PL-22AL are connected by a bridge 31 and neighboring medial struts 22PM-22AM are connected by a bridge 26. Accordingly, an embodiment of the arrangement represented by straps 25S includes a fully circumferential tensioning mechanism. Further, as described above, the constraining or tensioned force provided by this arrangement of straps 25S contributes to a medially directed FV on the proximal portion of lateral struts 22AL-22PL on a hosted residual limb, thereby contributing to a 3-point stabilization of the residual limb as shown in FIGS. 2B-2C and 2E-2F.

FIGS. 7C-7D shows an anterior view of an embodiment of a TF prosthetic socket frame 20 (without showing medial or lateral slings) showing only the constraining strap 25S disposed between neighboring lateral 22L and medial 22M struts. FIG. 7C shows the struts positioned relatively wide apart across an intervening cleft 24; FIG. 7D neighboring lateral 22PL-22AL and medial struts 22PM-22AM are positioned relatively close together across an intervening cleft 24. The extent to which neighboring lateral and medial struts are spaced apart is reflected in the total circumference, cross sectional area, or volume that prosthetic frame 20 encloses. The distance between neighboring lateral and medial struts thus creates a sizing adjustment that a user can adjust to his or her personal preference. It is anticipated that, in practice, these constraint adjustments will be stable throughout daily use; i.e., it is anticipated that these constraint adjustments will typically not be required during the course of a day, although a user may adjust this constraint to accommodate residual limb volume or preference changes over a longer time frame. In practice and in contrast, it is anticipated that users will make tensioning adjustments of positioning slings 210 and/or 250 with some frequency during each day.

Figure 8F:
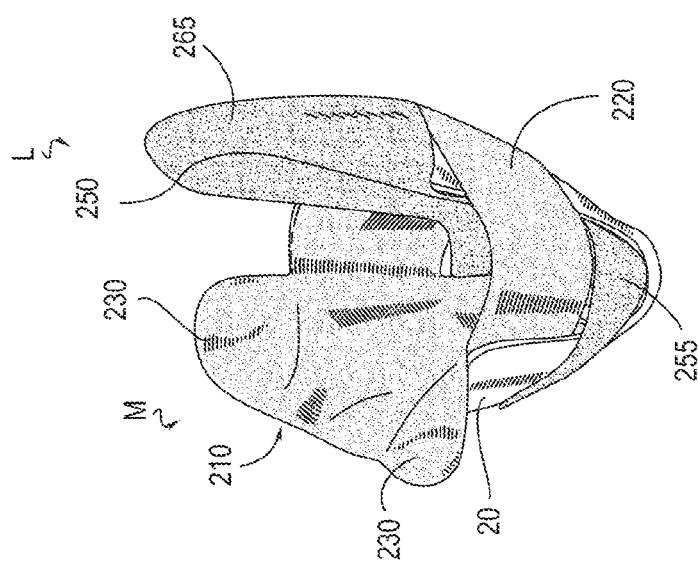
FIG. 8F shows the medial sling of FIG. 8B and the lateral sling of FIG. 8D both rigged into the TF prosthetic socket of FIG. 8A, according to one embodiment.

FIGS. 8A-8F focus on the disposition of lateral sling 250 and medial sling 210 as they are rigged in a prosthetic socket frame 20, making use of perspective views. FIGS. 8A-8C show, respectively, anterior views of a transfemoral (TF) prosthetic socket frame in isolation, a lateral sling 250 in isolation, and a lateral sling 250 rigged into TF prosthetic socket frame 20.

In detail, FIG. 8A shows an anterior view of an embodiment of a TF prosthetic socket frame 20, with a medial side M and a lateral side L. FIG. 8B shows an anterior view of an embodiment of a lateral sling 250 in isolation, as seen in an orientation like that of the TF prosthetic socket of FIG. 8A. FIG. 8C shows and anterior view of the lateral sling 250 of FIG. 8B rigged into the TF prosthetic socket of FIG. 8A.

With regard to the rigging arrangement by which lateral sling 250 suspends within prosthetic socket frame 20, trochanteric extensions 32 on lateral struts 22PL and 22AL on the lateral side L of prosthetic socket frame 20 are shown in FIG. 8A. A distal socket frame suspension site or pocket 265 is shown in FIG. 8B. FIG. 8C shows now suspension pocket 265 is arranged over trochanteric extensions 32, thus suspending lateral sling 250 within prosthetic socket 20. Suspension pocket 265, particularly the external portion thereof functions as a cover for the prosthetic socket frame.

In comparing the configuration of internal aspect of suspension suspension pocket portion 265 of lateral sling 250, it can be seen that in FIG. 8B internal face of pocket 265 is in repose (265R) across the internal aspect of lateral strut 27AL (strut PL is not visible), while in FIG. 8C, the internal face of suspension pocket 265 has been drawn taut (265T) across internal aspect of lateral struts. This taut configuration contributes to a medially directed force vector FV at the proximal aspect of lateral struts, as seen in FIGS. 2B, 2C, 2E, and 2F. This site of force application is the proximal most site of a 3-point leveraging system that provides lateral-medial stability of the residual limb within the prosthetic socket cavity.

Another aspect of embodiments of the invention that provide for medially directed support or pressure is provided by a pad or shim pocket 271 that can be inserted into a shim pocket 270 on an internal aspect of the proximal portion of lateral sling 250, as shown in FIGS. 9G-9M, and as described in that context below.

Figure 8E:
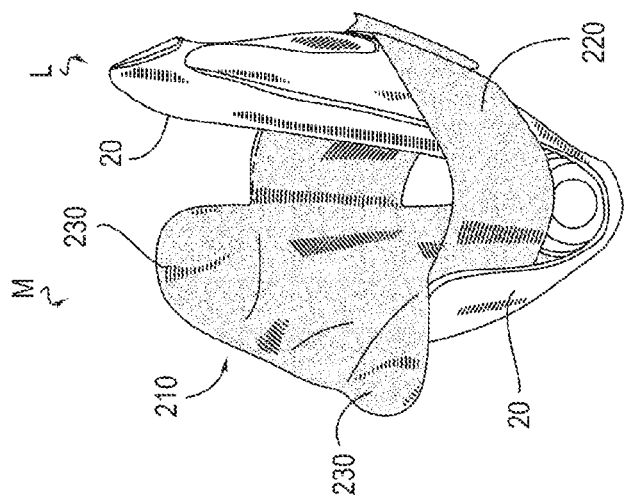
FIG. 8E shows the lateral sling of FIG. 8D rigged into the TF prosthetic socket of FIG. 8A, according to one embodiment.
Figure 8D:
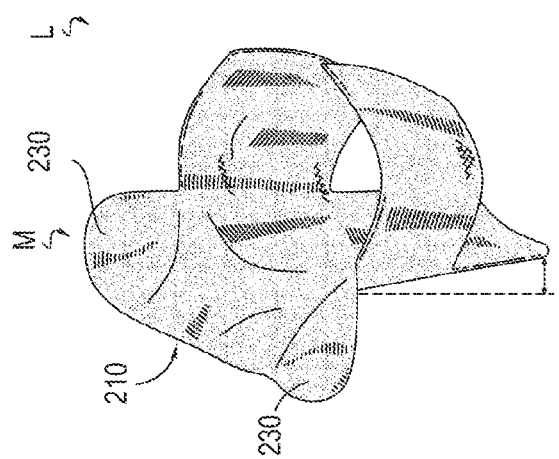
FIG. 8D shows an embodiment of a medial sling as seen in an orientation like that of the TF prosthetic socket of FIG. 8A.

FIGS. 8D-8E focus on a medial positioning sling 210 (rather than the lateral positioning sling 250 focus of FIGS. 8A-8C). FIG. 8D shows a medial sling 210, in isolation, in an arrangement and orientation congruous with the orientation of transfemoral (TF) socket frame 20 (FIG. 8A). FIG. 8E shows the lateral sling 250 of FIG. 8D rigged into the TF prosthetic socket 20. FIG. 8F shows the medial sling 210 of FIG. 8B and the lateral sling 250 of FIG. 8D both rigged into the TF prosthetic socket 20.

Turning now in more detail to the rigging arrangement by which medial sling 210 suspends within prosthetic socket frame 20, and referring back to FIG. 8A, which shows proximal flared portions of medial struts 22AM and 22PM. The proximal portion of strut 22AM has a flared portion 27A, and the proximal portion of strut 22PM has a flared portion 27B that may be adapted to form an ischium-supporting shelf. FIG. 8D shows two proximal prosthetic socket frame suspension pockets 230 of medial sling 210. FIG. 8E shows suspension pockets 230 arranged over flared portions 27A and 27B of medial struts 22AM and 22PM (refer to FIG. 8A). Suspension pocket 214, particularly the external portion thereof, functions as a cover for the prosthetic socket frame.

FIG. 8F shows both medial sling 210 and lateral sling 250 rigged over their respective suspension sites of prosthetic socket frame 20. The top perspective view provided by FIG. 8F corresponds to the side view provided by FIG. 7A.

FIGS. 9A-10B focus on embodiments of the invention by way of longitudinal cross sectional (sagittal plane) views that focus on depicting the effects that the tensioning of lateral positioning sling 250 and medial positioning sling 210 have on the positioning of these slings within the prosthetic socket 20, without the complication of depicting anatomy of the hosted residual limb.

Figure 9B:
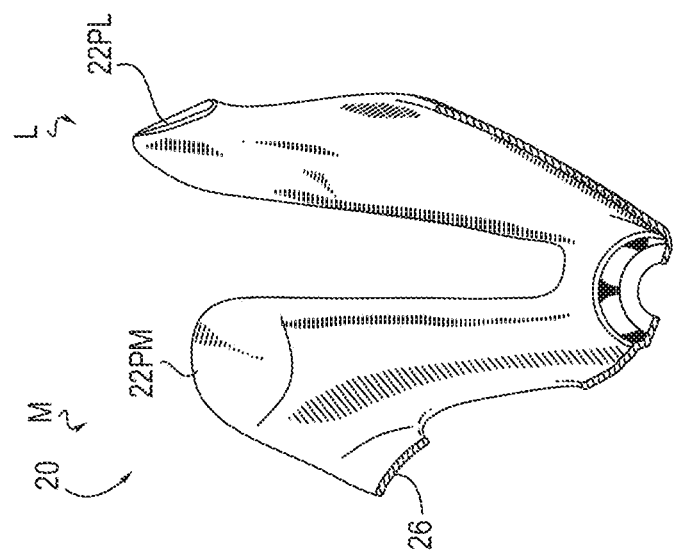
FIG. 9B is a sagittal plane cross-sectional cutaway view of the TF prosthetic socket frame of FIG. 9A.
Figure 9A:
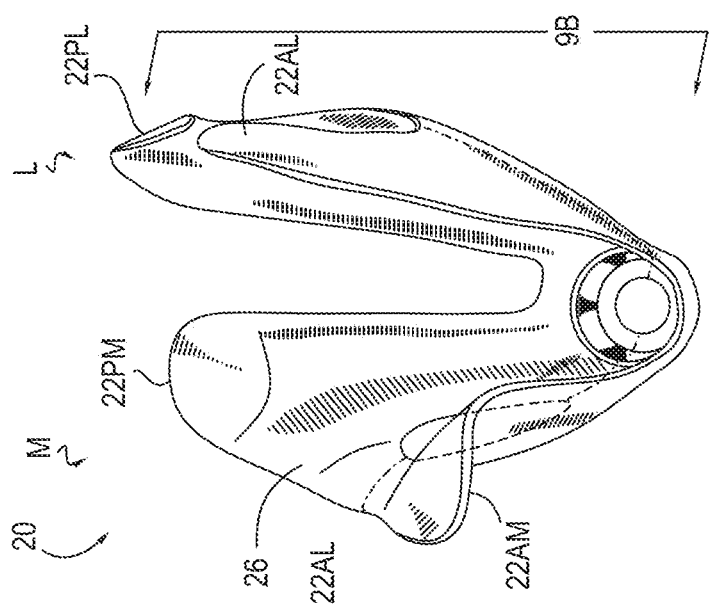
FIG. 9A is a partially transparent medial perspective view of an embodiment of a TF prosthetic socket frame.

FIG. 9A shows a partially transparent anterior perspective view (medial side M on the left, lateral side L on the right) of an embodiment of a TF prosthetic socket frame 20. FIG. 9B shows a sagittal plane cross sectional cutaway view of the TF prosthetic socket frame 20 of FIG. 9A. FIGS. 9A-9B are provided for general orientation in understanding FIGS. 9C-10B.

Figure 9E:
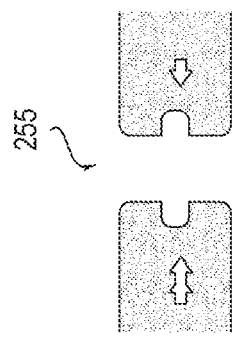
FIG. 9E is a schematic depiction of a connection mechanism for a lateral sling tensioning mechanism, showing the connection mechanism in an un-tensioned state, according to one embodiment.
Figure 9F:
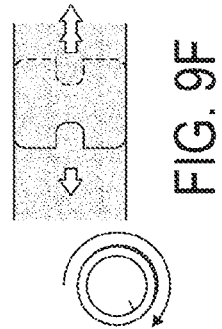
FIG. 9F is a schematic depiction of a connection mechanism for a lateral sling tensioning mechanism, showing the connection mechanism in a tensioned state, according to one embodiment.
Figure 9D:
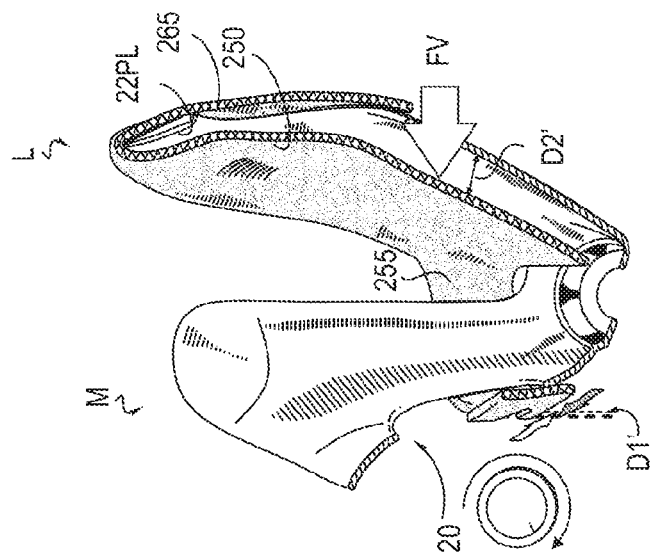
FIG. 9D shows an embodiment of a TF prosthetic socket frame with a lateral sling rigged therein (as in FIG. 9C), but with the sling being in a tensioned state.
Figure 9C:
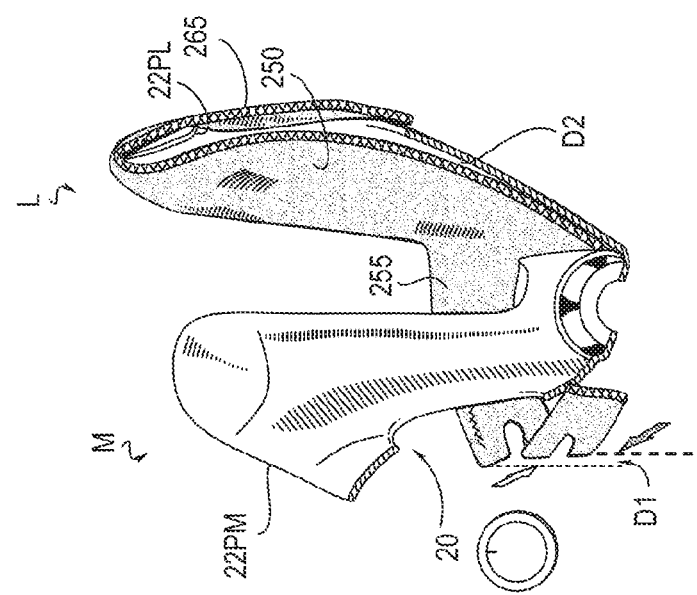
FIG. 9C shows a sagittal plane cross-sectional cutaway view of the TF prosthetic socket frame like that of FIG. 9B, further including a cross-sectional cutaway view of a lateral sling rigged within the socket frame, the sling being in an un-tensioned state, according to one embodiment.

FIG. 9C shows a sagittal plane cross sectional cutaway view of the TF prosthetic socket frame 20 like that of FIG. 9B, but further including a cross sectional cutaway view of a lateral sling 250 rigged within the socket frame 20, the sling being in an un-tensioned state. Posterior medial strut PM (without an attached sling) is on the left, and posterior lateral strut PL is on the right. A distal suspension pocket 265 of lateral sling 250 is arranged over strut 22PL.

FIG. 9D shows a view of an embodiment of a TF prosthetic socket frame 20 with a lateral sling 250 rigged therein (as in FIG. 9C), but with the sling being in a tensioned state. Notably, by way of applied tension (the pulling of tensioning strap 255, and manifesting as medially directed force vector arrow FV), an internal aspect of lateral sling 250 is being pulled medially. Note in FIG. 9C, a very small distance D2, which, in FIG. 9D has been increased to larger distance D2'.

FIG. 9E is a schematic depiction of a connection mechanism for a sling tensioning mechanism, showing the connection mechanism in an un-tensioned state. FIG. 9F is a schematic depiction of a connection mechanism for a sling tensioning mechanism, showing the connection mechanism in a tensioned state. The un-tensioned state of tensioning strap 255, shown in FIG. 9E is also reflected in FIG. 9C, where D1 indicates a relative distance between the ends of tensioning straps 255. The tensioned state of tensioning strap 255, shown in FIG. 9F is also reflected in FIG. 9C, where D1' indicates a relative distance between the ends of tensioning straps 255, wherein D1>D1'. This same relationship is also indicated by the dial icons of FIGS. 9C, 9D, 9F. More generally, the concept is that by tensioning or shortening or circumferentially tightening a tensionable mechanism, lateral sling 250 mediates a medially driven force.

FIGS. 9G-9M show various views of a shim pocket 270 disposed on the internal aspect of the proximal pocket portion 265 of a lateral sling 250; a shim or pad 271 (FIGS. 9K-9M) may be inserted into this pocket to increase the tension or pressure the trochanteric or proximal portion of the lateral side of the prosthetic frame exerts in a medial direction, against a residual limb hosted therein. Shims or pads 271 have a generally oval and flattened shape. Shims or pads 271 may include articles of varying durometer and varying size, and accordingly, allow the patient to optimize the fit of prosthetic socket to his or her personal preference.

FIG. 9G shows an embodiment of a TF prosthetic socket frame with a lateral positioning sling 250 rigged therein, the lateral sling having a pad or shim insertion pocket 270 on the internal aspect of its proximal portion. FIG. 9H shows a cutaway view of the proximal half of a TF prosthetic socket frame, showing, in particular, the position of the pad or shim insertion pocket with respect to the frame, as shown in FIG. 9G. FIG. 9I shows a ghosted view of a complete TF prosthetic socket frame 20, showing, in particular, the position of the pad or shim insertion pocket with respect to the frame, as shown in FIG. 9G.

Figure 9M:
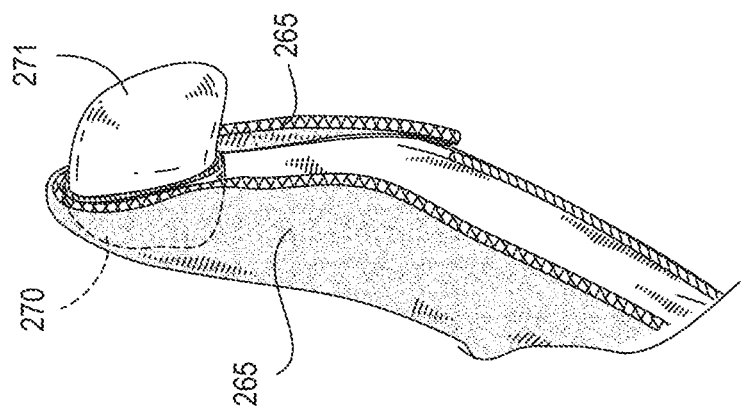
FIG. 9M shows a pad or shim being slipped into a side opening of an insertion pocket, as shown in FIG. 9J.
Figure 9K:
FIG. 9K is a side perspective view of an oval-shaped pad or shim suitable for insertion into the insertion pocket, as shown in FIG. 9J.
Figure 9L:
FIG. 9L is a narrow end side view of the oval-shaped pad or shim of FIG. 9K.
Figure 9J:
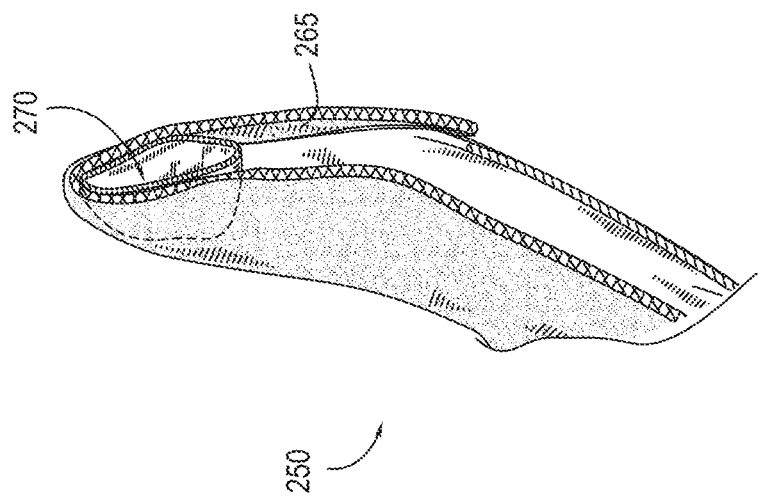
FIG. 9J shows a cross sectional view distal support attachment portion of a lateral sling, showing, in particular, the position of the pad or shim insertion pocket with respect to the sling, as shown in FIG. 9G.

FIG. 9J shows a cross sectional view distal support attachment portion of a lateral sling 250, showing, in particular, the position of the pad or shim insertion pocket with respect to the sling, as shown in FIG. 9G. FIG. 9K is a side perspective view of a generally oval-shaped pad or shim suitable for insertion into the insertion pocket, as shown in FIG. 9J. FIG. 9L is a narrow end side view of a of a generally oval-shaped pad or shim suitable for insertion into the insertion pocket, as shown in FIG. 9J. FIG. 9M shows a pad or shim being slipped into a side opening of an insertion pocket, as shown in FIG. 9J.

Figure 10A:
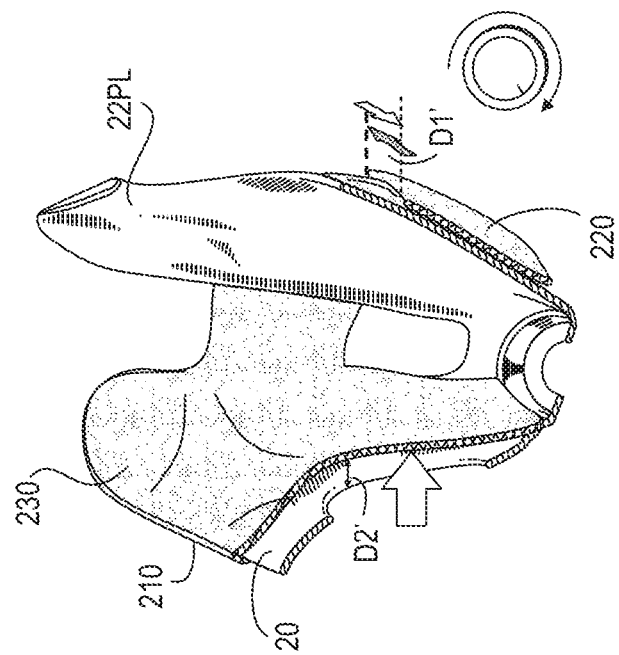
FIG. 10A shows a sagittal plane cross-sectional cutaway view of the TF prosthetic socket frame like that of FIG. 9B, further including a cross sectional cutaway view of a medial sling rigged within the socket frame, the sling being in an un-tensioned state.
Figure 10B:
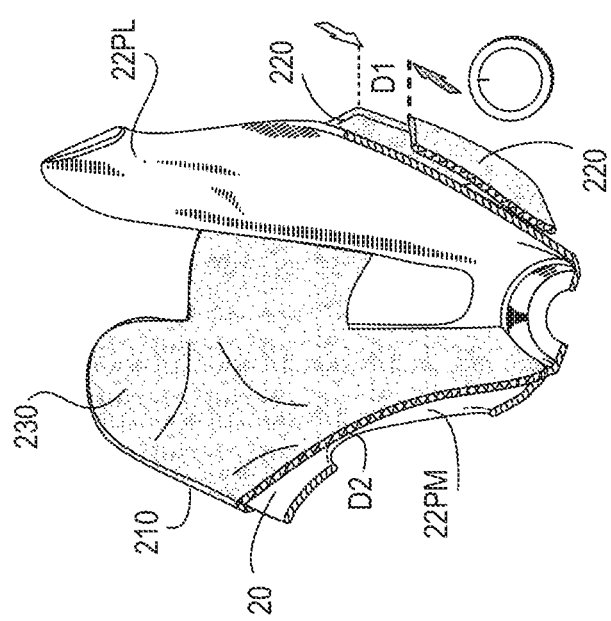
FIG. 10B shows a sagittal plane cross sectional cutaway view of the TF prosthetic socket frame like that of FIG. 9B, further including a cross sectional cutaway view of a medial sling rigged within the socket frame, the sling being in a tensioned state.

FIGS. 10A-10B are substantially parallel to views provided in FIGS. 9C-9D, but focus on medial positioning sling 210 (rather than lateral positioning sling 250). FIG. 10A shows a sagittal plane cross sectional cutaway view of the transfemoral (TF) prosthetic socket frame 20 analogous to FIG. 9B, further including a cross sectional cutaway view of a medial sling 210 rigged within the socket frame, the sling being in an un-tensioned state. Medial side M of prosthetic socket 20 is on the left; lateral side L is on the right. Posterior lateral strut 22PL (without an attached sling) is on the right, and posterior medial strut 22PM is on the left.

FIG. 10B shows a sagittal plane cross sectional cutaway view of the TF prosthetic socket frame 20 (like that of FIG. 9B) further including a cross sectional cutaway view of a medial sling 210 rigged within the socket frame, the sling being in a tensioned state. A proximal suspension pocket 230 of medial sling 210 is arranged over strut 22PM. (There are actually two such proximal suspension pockets 230; the other one, unseen because of the cutaway view, is arranged over strut 22AM.)

Notably, by way of applied tension (the pulling of tensioning strap 220, and manifesting as laterally directed force vector arrow FV), an internal aspect of medial sling 210 is being pulled laterally. Note in FIG. 10A, a very small distance D1, which, in FIG. 9D has been increased to larger distance D1'. The dial icons of FIGS. 10A-10B also refer to an un-tensioned state (FIG. 10A) and a tensioned state (FIG. 10B). The un-tensioned state of tensioning strap 220, shown in FIG. 10A is also reflected in the relatively large distance D1 indicated between the ends of tensioning straps 220. The tensioned state of tensioning strap 220 as shown in FIG. 10B is also reflected as relatively lengthened distance D1' between the ends of tensioning straps 220. More generally, the concept is that by tensioning or shortening or circumferentially tightening a tensionable mechanism, lateral sling 210 mediates a laterally driven or directed force.

Noting in particular that force vector arrow FV on the lateral side of lateral sling 250 (FIG. 9D) and the force vector arrow FV on the medial side of medial sling 210 (FIG. 10B) are opposing forces that cooperate in stabilizing and biomechanically optimizing the disposition of the residual limb within prosthetic socket frame 20.

FIGS. 11A-11C and FIGS. 12A-12C continue the depiction of aspects of the dynamics of positioning slings 210 and 250, respectively, using cutaway views to focus particularly on the effects of sling tensioning on the residual limb being hosted within TF prosthetic socket 20.

Figure 11C:
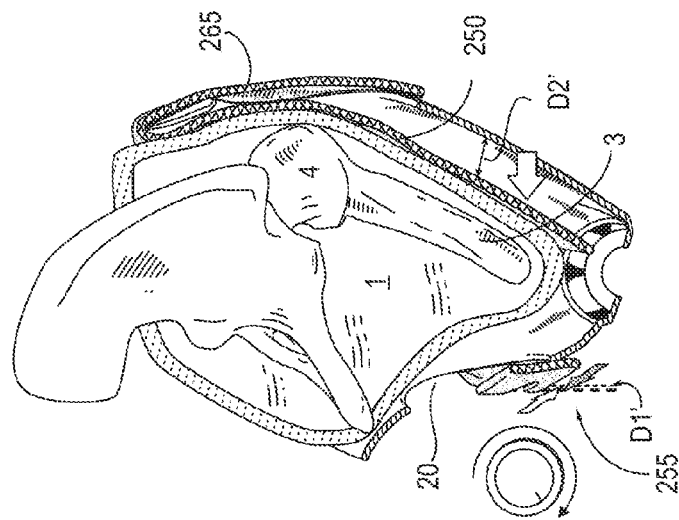
FIG. 11C shows a view of an embodiment of a TF socket containing a residual limb therein (as in FIG. 11A), further showing a lateral sling embodiment rigged therein, the sling in a tensioned state.
Figure 11B:
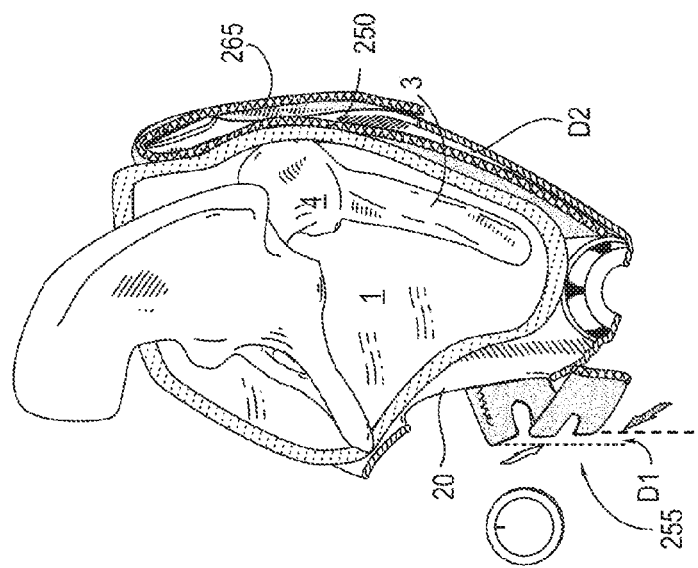
FIG. 11B shows an anterior view of an embodiment of a TF prosthetic socket containing a residual limb therein (as in FIG. 11A), further showing a lateral sling embodiment rigged therein, the sling in an un-tensioned state.
Figure 11A:
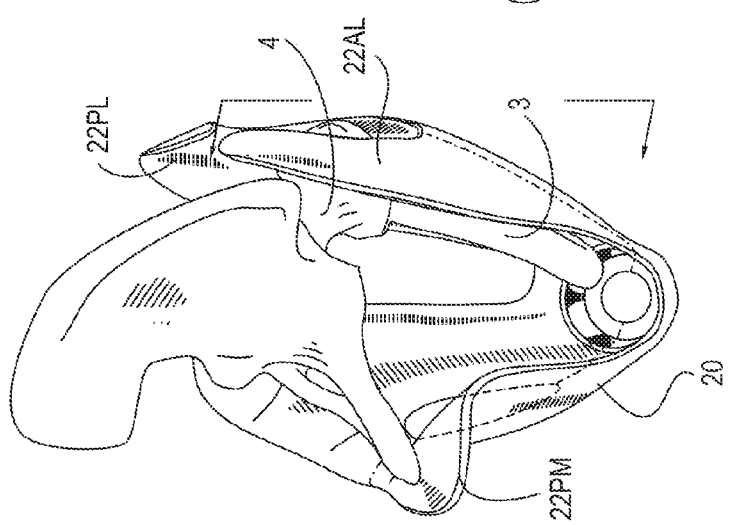
FIG. 11A shows an anterior view of an embodiment of a TF prosthetic socket frame, further transparently showing the femur and pelvic skeletal anatomy hosted therein.

FIGS. 11A-11C focus on the disposition of a residual limb 1 within a prosthetic socket frame and the effect thereon of tensioning a tensioning mechanism of a lateral sling 250. FIG. 11A shows an anterior open view (not cutaway, as are FIGS. 11B-11C) of an embodiment of a transfemoral (TF) prosthetic socket frame 20, further transparently showing residual femur 3 and the surrounding pelvic skeletal anatomy hosted therein.

FIG. 11B shows an anterior cutaway view of an embodiment of a TF prosthetic socket containing a residual limb 1 therein (as in FIG. 11A), further showing a lateral positioning sling 250 embodiment rigged therein, the sling in an un-tensioned state. FIG. 11C shows an anterior view of an embodiment of a TF socket containing a residual limb 1 therein (as in FIG. 11A), further showing lateral sling 250 rigged therein, the sling in a tensioned state. As lateral sling 250 is tensioned by way of tensioning arm portions 255, a force vector arrow FV is created on the lateral side of the sling, drawing it, and the hosted residual limb 1 medially. This medially-directed pull is reflected in distance D2', which is greater than distance D2 as seen in FIG. 11B.

Similarly, distance D1 between the ends of tensioning straps 255 as seen in FIG. 11B is greater than distance D1', as seen in FIG. 11C. This same un-tensioned vs. tensioned state is also reflected in the dial icons of FIGS. 11A-11B, to the left of each main figure. More generally, the concept is that by tensioning or shortening or circumferentially tightening a tensionable mechanism, lateral sling 250 mediates a medially driven force.

Figure 12C:
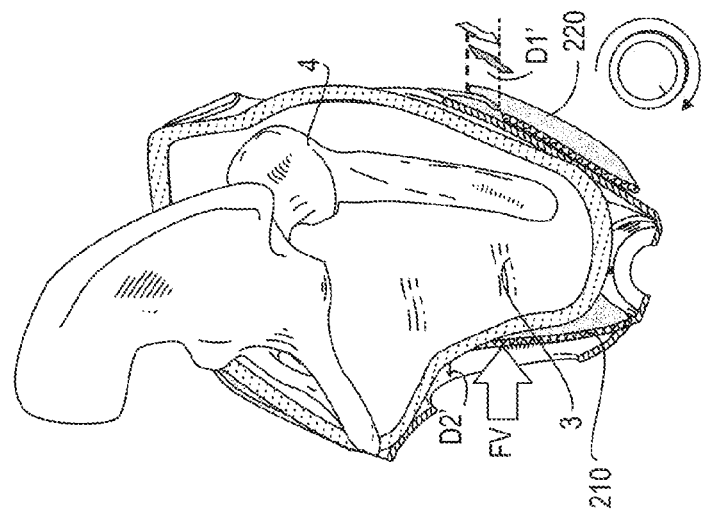
FIG. 12C shows an anterior view of an embodiment of a TF prosthetic socket containing a residual limb therein (as in FIG. 12A), further showing a medial sling embodiment rigged therein, the sling in a tensioned state.
Figure 12B:
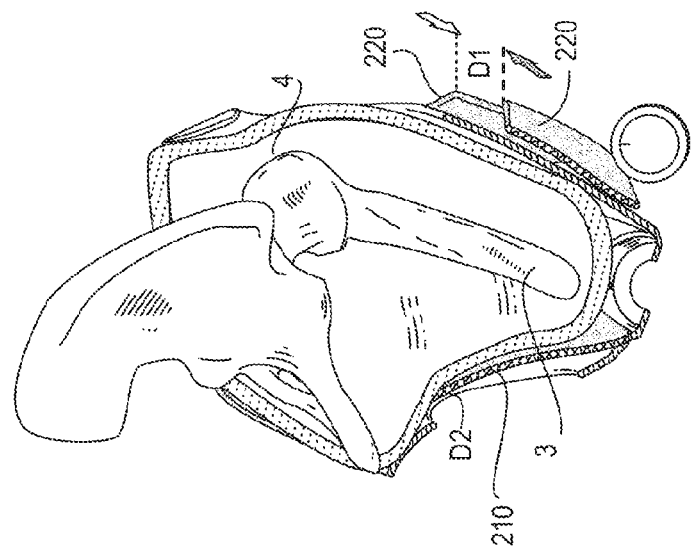
FIG. 12B shows an anterior view of an embodiment of a TF prosthetic socket containing a residual limb therein (as in FIG. 12A), further showing a medial sling embodiment rigged therein, the sling in an un-tensioned state.
Figure 12A:
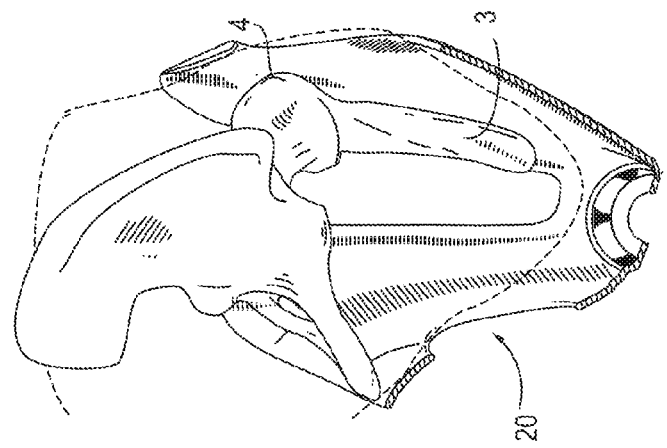
FIG. 12A shows an anterior view of an embodiment of a TF prosthetic socket frame, further transparently showing the femur and pelvic skeletal anatomy hosted therein.

FIGS. 12A-12C focus on the disposition of a residual limb 1 within a prosthetic socket frame 20 and the effect thereon of tensioning a tensioning mechanism of a medial sling 210. FIG. 12A shows an anterior open view (not cutaway, as are FIGS. 12B-12C) of an embodiment of a transfemoral (TF) prosthetic socket frame 20 (not showing a sling), and further transparently showing the femur 3 and pelvic skeletal anatomy hosted therein.

FIG. 12B shows an anterior cutaway view of an embodiment of a TF prosthetic socket hosting a residual limb 1 therein (as in FIG. 12A), further showing a medial positioning sling 210 embodiment rigged therein, the sling in an un-tensioned state. FIG. 12C shows an anterior view of an embodiment of a TF socket containing a residual limb 1 therein (as in FIG. 12A), further showing a medial sling 210 embodiment rigged therein, the sling in a tensioned state.

As medial sling 210 is tensioned by way of tensioning arm portions 220, a force vector arrow FV is created on the medial side of the sling, drawing the hosted residual femur 3 laterally. This laterally-directed pull is reflected in distance D2' (FIG. 12C), which is greater than the distance D2, as seen in FIG. 12B.

Similarly, distance D1 between the ends of tensioning arm portions 220 as seen in FIG. 12B is greater than distance D1', as seen in FIG. 12C. This same un-tensioned vs. tensioned state is also reflected in the dial icons of FIGS. 12A-12B, to the left of each main figure. More generally, the concept is that by tensioning or shortening or circumferentially tightening a tensionable mechanism, medial sling 210 mediates a laterally driven force.

FIGS. 13A-13B and FIGS. 14A-14B show, respectively, lateral positioning sling 250 and medial positioning sling 210, each sling in isolation (i.e., no socket frame elements, no residual limb), in order to focus and expand on various positioning sling dynamics, as described above in context of FIGS. 11A-12C.

Figure 13B:
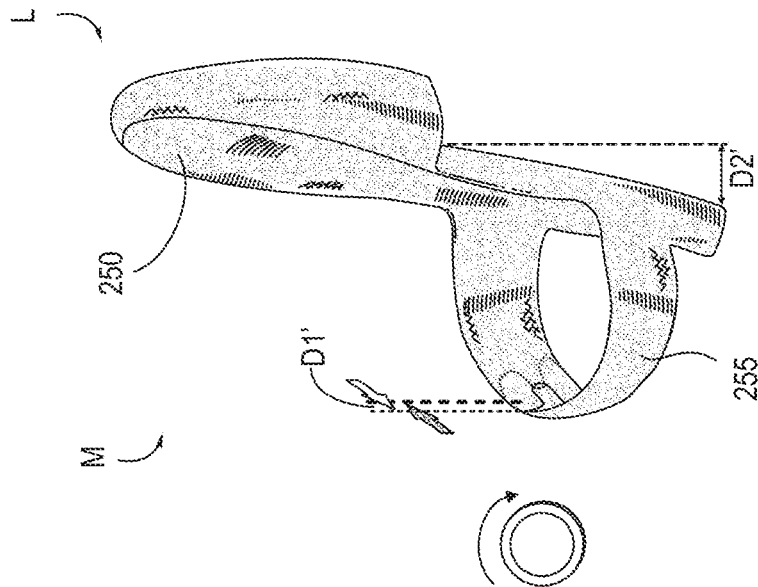
FIG. 13B shows an embodiment of a lateral sling for a TF prosthetic socket in isolation, in a tensioned state.
Figure 13A:
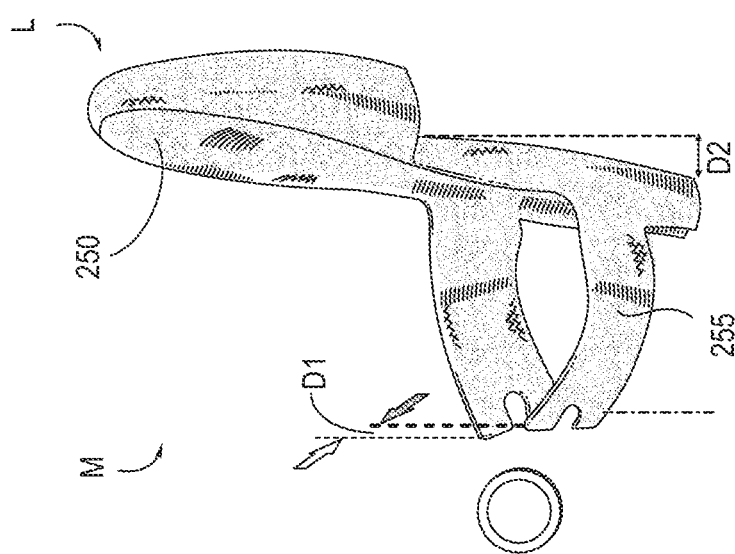
FIG. 13A shows an embodiment of a lateral sling for a TF prosthetic socket in isolation, in an un-tensioned state.

FIGS. 13A-13B show a lateral positioning sling 250 for a TF prosthetic socket frame 20 in an un-tensioned and a tensioned state, respectively, without the visual complication of showing the prosthetic socket frame itself, or a residual limb 1 hosted therein. FIG. 13A shows lateral sling 250 for a TF prosthetic socket in an un-tensioned state; FIG. 13B shows lateral sling 250 in a tensioned state. In the un-tensioned state (FIG. 13A), distance D1 between the two ends of tensioning straps 255 is relatively large compared to distance D1' as seen in FIG. 13B. And in the un-tensioned state (FIG. 13A), distance D2 between external aspect of lateral sling 250 and an internal aspect of lateral side of prosthetic socket frame 20 (not shown) is relatively small as compared to larger distance D2' as seen FIG. 13B. These various changes in distance are also reflected in the medially directed force vector FV shown (FIG. 11C) at the lateral side of sling 250 which contributes to stabilizing and biomechanically optimizing the disposition of residual limb 1 within prosthetic socket frame 20.

Figure 14B:
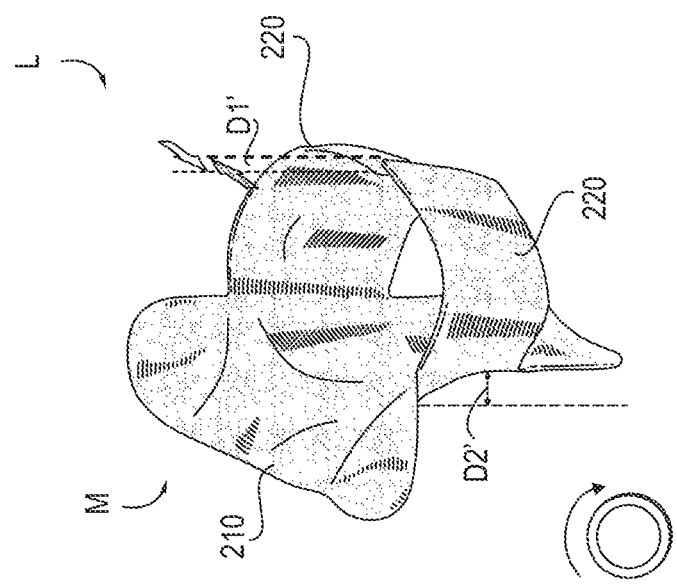
FIG. 14B shows an embodiment of a lateral medial sling for a TF prosthetic socket in isolation, in a tensioned state.
Figure 14A:
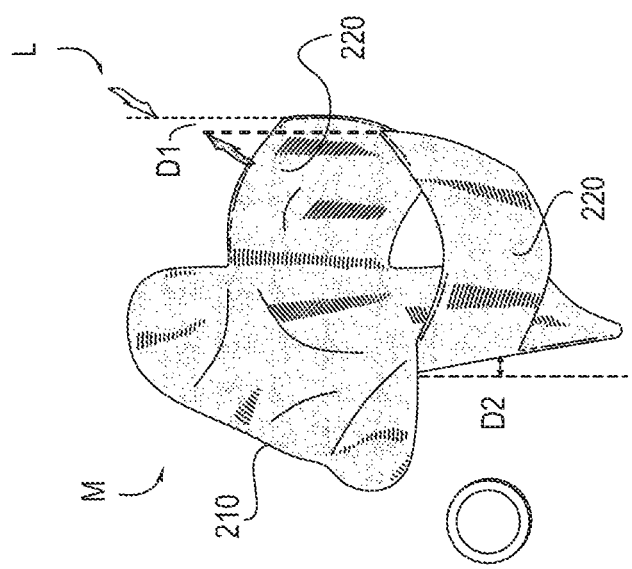
FIG. 14A shows an embodiment of a lateral medial sling for a TF prosthetic socket in isolation, in an un-tensioned state.

FIGS. 14A-14B show medial positioning sling 210 for a TF prosthetic socket frame 20 in an un-tensioned and a tensioned state, respectively, without the visual complication of showing the prosthetic socket frame itself. FIG. 14A shows a medial sling 220 for a TF prosthetic socket, in isolation, in an un-tensioned state; FIG. 14B shows a medial sling 220 in a tensioned state. In the un-tensioned state (FIG. 14A), distance D1 between the two ends of tensioning straps 220 is relatively large compared to distance D1' as seen in FIG. 14B. And in the un-tensioned state (FIG. 14A), distance D2 between external aspect of sling 210 and an internal aspect of medial side of prosthetic socket frame 20 (not shown) is relatively small compared to distance D2' as seen FIG. 14B. These various changes in distance are also reflected in the laterally directed force vector FV shown at the medial side of sling 210 (FIG. 12C) which contributes to stabilizing and biomechanically optimizing the disposition of residual limb 1 within prosthetic socket frame 20.

Noting, in particular, that the tensioning dynamics of lateral positioning sling 250 (FIGS. 13A-13B) and medical positioning sling 210 (FIGS. 14A-14B), as depicted also in FIGS. 11A-11B and FIGS. 12A-12B, respectively in the form of force vector FV arrows are opposing forces that cooperate in stabilizing and biomechanically optimizing the disposition of the residual limb within prosthetic socket frame 20.

FIGS. 15A-16B show various views of embodiments of flat patterns for medial sling 210FP and lateral sling 250FP suitable for a TF prosthetic socket frame. The "FP" addendum to sling labels 210 and 250 is to call attention to the flat configuration of a sling as shown, which is different than 3-dimensionally arranged configurations depicted in other figures. In another aspect, FIGS. 15A-16B may serve as representations of patterns for slings to be followed when fabricating slings (i.e., not the slings per se.) These are typically integral patterns, a single fabric unit, even though they may be assembled from multiple pieces.

Medial sling pattern 210FP and lateral sling 250FP include a variety of fabrics that vary with respect to degrees of elasticity or ability to stretch (among other attributes). For example, some fabric material 241 is substantially non-elastic, and does not stretch. Some fabric material 242 has minimal stretch. Some fabric material 243 has a biased stretch in that it is elastic along one axis and is substantially inelastic along the orthogonal axis. Such a stretch along one axis is also referred to as a 2-way stretch in the textile arts. As oriented within flat patterns and as oriented when a sling is arranged within a prosthetic socket frame, at least in some areas of the flat pattern, stretch is typically allowed along the X-axis, or horizontally, and stretch is typically disallowed along the Y-axis, or vertically. Some fabric material 244 has 360-degree elastic properties, as aligned on both X- and Y-axes (horizontally and vertically). Such stretch can also be referred to as a 4-way stretch in the textile arts.

Figure 15A:
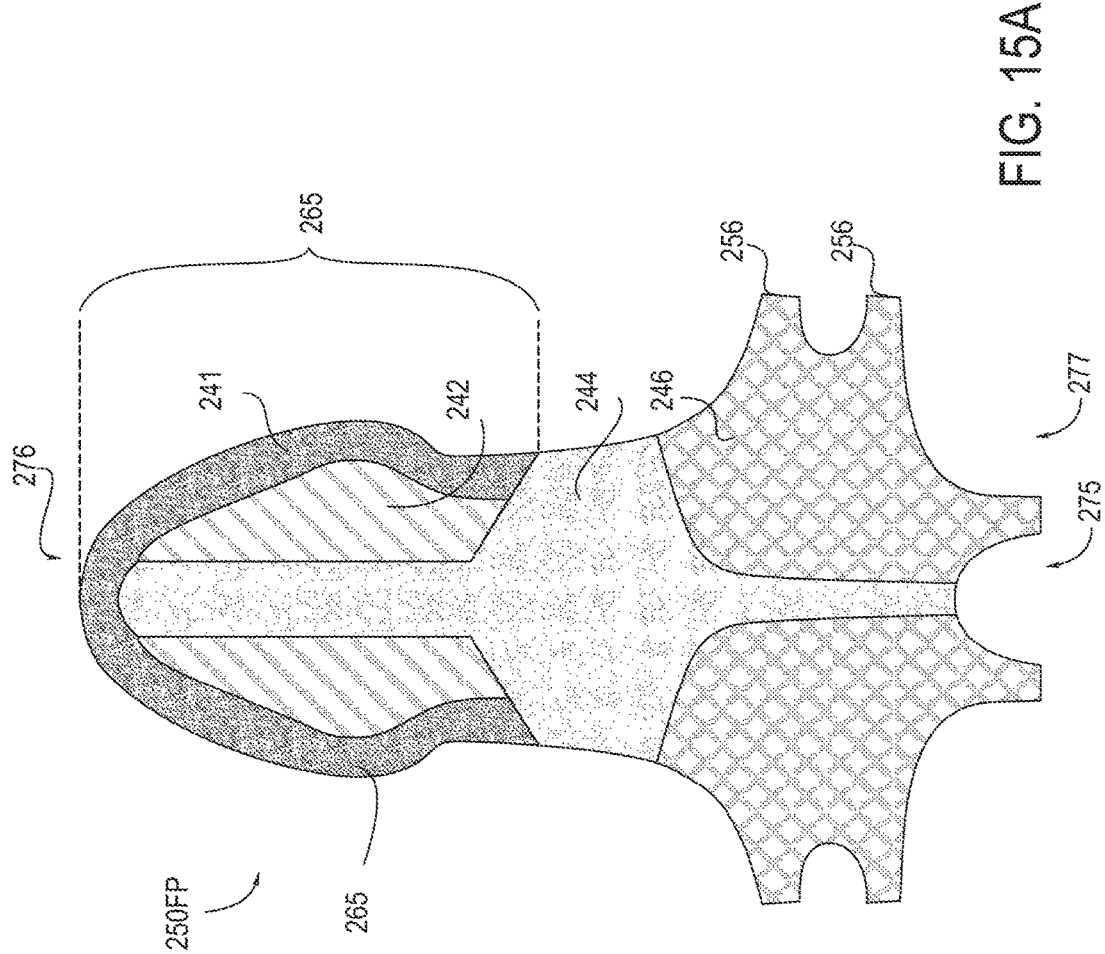
FIG. 15A shows an external view of an embodiment of flat pattern for a lateral sling (tensioning straps not shown)

FIGS. 15A-15C show various views of a flat pattern 250FP for a lateral positioning sling 250. FIG. 15A shows an internal view of an embodiment of flat pattern for a lateral sling 250FP; FIG. 15B shows an internal view of an embodiment of flat pattern for a lateral sling as in FIG. 15A, but further showing a shim pocket 270 on the internal surface of the proximal portion of the pattern, as well as a shim 271 that is insertable into the pocket.

FIG. 15C shows an external view of an embodiment of a flat pattern for a lateral sling; the only portion of sling 250 that is visible in such a view is that proximal suspension pocket 265 and extension tabs 256, a component of a circumferential tensioning system 255, of positioning sling 250 as seen in in FIGS. 5A-5D and elsewhere. Dotted lines represent the distal portion of flat pattern 250FP positioned within a prosthetic socket, and not visible in an external view.

Lateral positioning sling flat pattern 250FP is oriented with proximal end 276 at the top and distal end 277 at the bottom. Distal attachment sites 275 are for connecting to a socket structure at located at the distal end of a socket cavity, as may be appropriate in some embodiments. In other embodiments, flat pattern 250FP and flat pattern 210FP (see FIGS. 16A-16B) maybe be conjoined, as shown in FIGS. 17A-17B.

Substantially non-elastic material 241 may be disposed around the periphery of the proximal portion of sling flat pattern 250FP; this is visible in each of FIGS. 15A-15C. This portion of sling 250, when arranged within a prosthetic socket frame, acts as a suspension pocket 265. Suspension pocket 265 includes what are originally two pieces: the major portion of flat pattern 250FP and an external piece 265Ext, as seen in FIG. 15C. The proximal portions of 250FO and 265Ext are connected together to form the distally open suspension pocket 265. Suspension pocket 265 is configured to fit over trochanteric extension portion 32 of prosthetic socket frame 20, as seen, for example, in FIGS. 8B-8C.

Minimal stretch fabric 242 can be seen within the proximal portion of lateral sling flat pattern 250FP or the internal aspect of proximal support pocket 265. The minimally stretchable fabric 242 allows some stretch for conformability, but with sufficient structural integrity to permit force transfer from the fabric onto the trochanteric portion of a hosted residual limb.

Biased elastic (2-way stretch) fabric 243 can be seen in the distal portion of lateral sling flat pattern 250FP. In this portion of sling 250, the stretch is designed to be minimal horizontally so as to allow creation of sufficient circumferential tension when a tensioning mechanism is applied through this region. 360-degree elastic (4-way stretch) fabric 244 can be seen in central horizontal and vertical aspects of sling flat pattern 250FP.

Figure 16A:
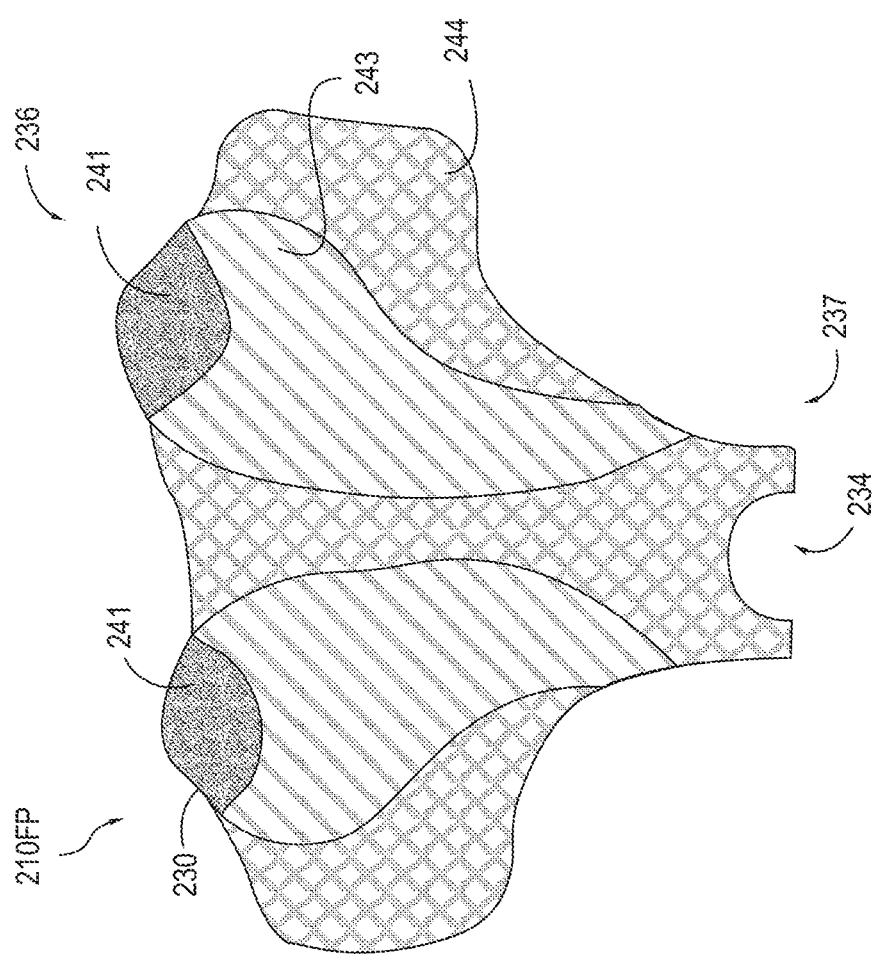
FIG. 16A shows an external view of an embodiment of a flat pattern for a medial sling.
Figure 17A:
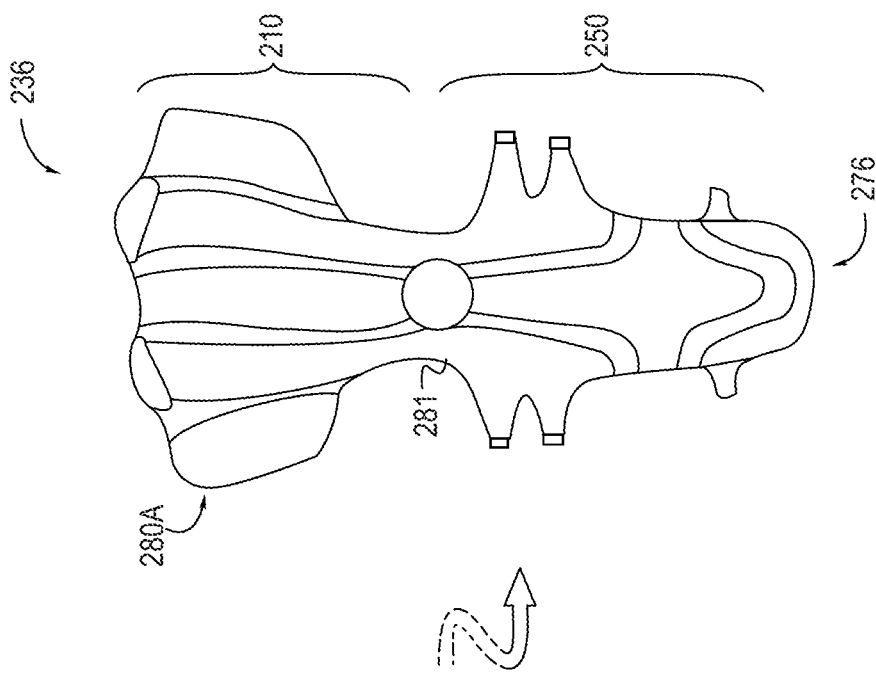
FIG. 17A shows a cylindrical residual limb (left panel of FIG. 17A) and a conjoined (medial plus lateral) sling flat pattern accordingly configured to accommodate the cylindrical limb (right panel of FIG. 17A)

FIGS. 16A-16B show views of a flat pattern 210FP for a medial positioning sling 210 as depicted and described elsewhere. FIG. 16A shows an external view of an embodiment of a flat pattern 210FP for a medial sling 210. FIG. 16B shows an external view of an embodiment of the flat pattern for a medial sling as in FIG. 16A, but further showing a horizontally disposed tensioning element or tab 222, a component of circumferential tensioning system 220 for medial positioning sling 210, as described elsewhere.

Medial positioning sling flat pattern 210FP is oriented with proximal end 236 at the top and distal end 237 at the bottom. Distal attachment sites 234 are for connected to a socket structure at located at the distal end of a socket cavity, as may be appropriate in some embodiments. In other embodiments, flat pattern 250FP and flat pattern 210FP (see FIGS. 16A-16B) maybe be conjoined, as shown in FIGS. 17A-17B.

Substantially non-elastic material 241 can be seen around the periphery of the two regions of proximal portion of sling 210FP. These portions of sling 210, when arranged within a prosthetic socket frame, form suspension pockets 230. Suspension pockets 230 include what are originally two pieces: the major portion of flat pattern 210FP and an external piece (not shown). The proximal portions of 210FO and the external pieces are connected together to form the distally open suspension pockets 230. Suspension pockets 230 are configured to fit over proximal ends 27A-27B of medial struts 22PM and 22AM, as in FIGS. 8D-8F.

Minimal stretch fabric 242 can be seen extending distally from suspension pockets 230. 360-degree elastic (4-way stretch) fabric 244 can be seen form the bulk of the medial, anterior, and posterior regions of medial flat pattern 210FP.

As described above, flat patterns for slings may be custom-fitted to residual limbs of varying size and shape by way of algorithms that translate a 3-dimensional profile into a 2-dimensional flat pattern. Further, while embodiments of medial sling flat pattern 210FP and lateral sling 250FP have been shown in FIGS. 15A-16B as separate flat patterns, such separate patterns can be conjoined at their respective distal ends to create an integrated positioning sling flat pattern 280A. Conjoining may occur either by joining originally separate flat patterns, or by fabricating a single integrated flat pattern that includes a lateral sling portion 250 (bottom) and a medial sling portion 210 (top) to form a conjoined flat pattern 280A (or 280B. A central portion 281 of flat pattern 280A represents the mating of conjoining of the distal ends of each individual flat pattern. Fabricating a conjoined flat pattern may occur by fabricating the individual patterns individually, and then joining them, or the fabrication may occur by fabricating a pattern that is fully integrated from the outset.

Accordingly, FIG. 17A shows a cylindrical residual limb 1A and a conjoined (medial plus lateral) sling flat pattern 280A configured to accommodate the cylindrical limb 1A. FIGS. 17A-17B also depict a method by which a flat pattern can be custom fabricated to fit a particular individual. Any suitable scanning method of residual limb 1A can be used to modify a flat pattern template. As shown in FIG. 17A, a relatively thin residual limb can generate a relatively thing sling flat pattern 280A. As shown in FIG. 17B, a relatively large residual limb can generate a relatively large sling flat pattern 280B.

By way of methods described in U.S. patent application Ser. No. 14/731,163 (filed Jun. 4, 2015 and incorporated herein by this reference) that create a digital profile (e.g., by scanning or photogrammetry) of a residual limb and processing that digital profile to yield a conforming flat pattern 280. Similarly, FIG. 17B shows a conical residual limb 1B and a conjoined (medial plus lateral) sling flat pattern 280B configured to accommodate the conical limb 1B. By this approach, based on a modifiable model flat pattern, such flat pattern can be used to generate flat patterns such as 280A (for a conical residual limb) and 280B (for a conical residual limb).

FIGS. 17A-17B show proximal end 236 of medial sling flat pattern portion 210 at the top of the pattern and proximal end 276 of lateral sling flat pattern portion 250 at the bottom of the pattern. Conjoinment site 281 between portions 210 and 250 and a site of distal attachment 234 to the host prosthetic socket are both shown in the center of patterns 280A and 280B.

Medial and Lateral slings (exemplified by medial sling 210 and lateral sling 250) as shown particularly in flat pattern depictions of FIGS. 16A-17B, are modular in character, by several criteria. For example, slings may be fabricated in a range of sizes and shapes, and yet, in spite of such variation in form, are consistent in terms of their connectability, compatibility, and ability to fit within a given prosthetic socket (e.g., transfemoral prosthetic socket frame 20). Such a range of sizes and shapes can be held in an inventory, or, alternatively, can be fabricated on demand, from a virtual inventory.

Further still, medial and lateral slings (210, 250) are assembled from component fabric pieces that also may be fabricated in a range of sizes and shapes, maintaining their compatibility with other component pieces such that a full sling can be fabricated therefrom. And, as with fully assembled slings, such a range of sling component piece sizes and shapes can be held in an inventory, or, alternatively, can be fabricated on demand, from a virtual inventory.

Further, although medial and lateral slings (210, 250) are depicted in the context of a particular prosthetic socket frame (transfemoral prosthetic socket frame 20), embodiments of the invention include devices with appropriate design alternations to fit other types of prosthetic socket devices, including devices configured for both transfemoral residual limbs, knee disarticulation residual limbs, and transtibial residual limbs. Further, other prosthetic socket devices include those configured for upper level residual limbs, of any level. Further still, embodiments of the invention include related orthopedic devices, such as braces, and such as socket-engagement portions of larger devices, such as exoskeletons.

In another aspect of the invention, based on preceding description of the modular character of fabric slings, prosthetic sling kits are provided. Such kits may include, by way of example, a fully fabricated sling with associated enabling components, such as fasteners and tensioning mechanisms. Kits may also include component pieces. Component pieces may be provided in variations, such as variations in fabrics. Kits may also include multiple assembled sling units or sufficient number of components to assemble a plurality of fully assembled sling units. And, as noted above, kits of assembled units or component pieces may be configured to be appropriate for any suitable prosthetic socket frame, or any suitable related orthopedic device.

FIGS. 18A-18C show a distal base assembly suitable for application to a transfemoral (TF) prosthetic socket frame as provided herein. FIG. 18A shows a bottom perspective view of a distal base 35. FIG. 18B shows a bottom face view of a distal base in an extended offset alignment position. FIG. 18C shows a bottom face view of a distal base in a neutral alignment position. Three main distal base assembly components are shown in FIGS. 18A-18C, including a distal base plate 35A (the most proximal component), a distal base rotational clamp 35B, and a slidable offset adapter 35C (the most distal component).

Distal base portion 35A of this distal base assembly may be laminated into the distal most aspect of a TF prosthetic frame 20. The function of a distal base assembly is to functionally connect a TF socket frame 20 to more distal prosthetic components and to provide an alignment capability such that distal components are aligned with the prosthetic socket assembly in a manner biomechanically appropriate for the patient. A rotational clamp 35B embodiment is rotatable with respect to the distal base (which is fixed within the socket), thus providing a rotational aspect of alignment within an arc of up to about 45 degrees. A distal sliding adapter 35C is mounted within the rotational base clamp, and provides an ability to offset (typically a posterior offset) the central longitudinal axis of distal components from a default central position with respect to the prosthetic socket frame.

Aspects and features of an alignable distal base appropriate for TF prosthetic socket frame, similar in various ways to the distal base assembly provided herein, have been described in U.S. Pat. No. 9,468,542 of Williams and Hurley entitled "Alignable coupling assembly for connecting two prosthetic limb components", as filed on May 4, 2015, which is incorporated into this present application by this reference thereto.

Some aspects and features of a distal base assembly, including a distal funnel structure that anchors distal portions of positioning slings that are appropriate for rigging within a TF prosthetic socket frame are described in a U.S. Provisional Patent Applications No. 62/237,232 of Hurley et al., filed on Oct. 5, 2015, and No. 62/259,855 of Hurley et al., filed on Nov. 25, 2015, both of which are entitled "An integrated multi-material, multi-layer prosthetic socket liner garment", which are incorporated into this present application by this reference thereto.

Any one or more features of any embodiment described herein may be combined with any one or more other features of any other embodiment, without departing from the scope of the invention. Further, the invention is not limited to the embodiments that are described or depicted herein for purposes of exemplification, but is to be defined only by a fair reading of claims appended to the patent application, including the full range of equivalency to which each element thereof is entitled. Further, while some theoretical considerations have been offered to provide an understanding of the technology (e.g., the effectiveness of a positioning slings in improving biomechanical control of the residual limb by acting on the residual bone as a lever), the claims are not bound by such theory.

The invention claimed is:

1. A sling system for a transfemoral prosthetic socket, the sling system comprising:
a medial sling; and
a lateral sling, wherein the medial sling and the lateral sling each comprise:
a fabric body comprising a residual limb interfacing portion adapted to be disposed within a prosthetic socket frame;
one or more proximal suspension portions adapted to suspend from a proximal aspect of a prosthetic socket frame; and
a tensioning system;
wherein, when disposed within a prosthetic socket frame, each sling is arranged as a longitudinally aligned tube comprising an open proximal end and a closed distal end,
wherein the medial sling comprises a lateral side comprising the one or more proximal suspension portions and a medial side comprising the residual limb interfacing portion of the medial sling, and wherein, when the tensioning system is tensioned, the medial sling is pulled toward the lateral side of the prosthetic socket frame, and
wherein the lateral sling comprises a medial side comprising the one or more proximal suspension portions and a lateral side comprising the residual limb interfacing portion of the medial sling, and wherein, when the tensioning system is tensioned, the lateral sling is pulled toward the medial side of the prosthetic socket frame,
wherein the medial sling and the lateral sling are cooperatively operable to balance laterally directed and medially directed forces to support the residual limb centrally within the prosthetic socket frame, and
wherein the lateral sling is tensionable toward the medial side of the prosthetic socket at two longitudinally positioned sites, a proximal site and a distal site, and wherein the medial sling is tensionable toward the lateral side of the prosthetic socket at a longitudinally central site, between the proximal and distal sites of the lateral sling.

2. The sling system of claim 1, wherein the tensioning system of the medial sling and the tensioning system of the lateral sling are operable independently of each other.

3. The sling system of claim 1, wherein the two longitudinally positioned tensioning sites of the lateral sling and the longitudinally central site of the medial sling comprise a three-point residual limb stabilizing arrangement within the prosthetic socket frame.

\* \* \* \* \*